(12) United States Patent
Sato et al.

(10) Patent No.: US 7,678,810 B2
(45) Date of Patent: Mar. 16, 2010

(54) THIAZOLE DERIVATIVE

(75) Inventors: Masakazu Sato, Tokyo (JP); Yuko Matsunaga, Tokyo (JP); Hajime Asanuma, Tokyo (JP); Hideaki Amada, Tokyo (JP); Takeshi Koami, Tokyo (JP); Tetsuo Takayama, Tokyo (JP); Tetsuya Yabuuchi, Tokyo (JP); Fumiyasu Shiozawa, Tokyo (JP); Hironori Katakai, Tokyo (JP); Hiroki Umemiya, Tokyo (JP); Akiko Ikeda, Tokyo (JP)

(73) Assignee: Taisho Pharmaceutical Co., Ltd, Tokyo (JP)

( * ) Notice: Subject to any disclaimer, the term of this patent is extended or adjusted under 35 U.S.C. 154(b) by 676 days.

(21) Appl. No.: 10/591,614

(22) PCT Filed: Mar. 4, 2005

(86) PCT No.: PCT/JP2005/003755

§ 371 (c)(1),
(2), (4) Date: Sep. 5, 2006

(87) PCT Pub. No.: WO2005/085241

PCT Pub. Date: Sep. 15, 2005

(65) Prior Publication Data

US 2007/0154428 A1   Jul. 5, 2007

(30) Foreign Application Priority Data

Jun. 5, 2004 (JP) ............... 2004-062321
Nov. 29, 2004 (JP) ............... 2004-344307

(51) Int. Cl.
*A61K 31/4439* (2006.01)
*C07D 277/62* (2006.01)
*C07D 317/48* (2006.01)

(52) U.S. Cl. .................. 514/301; 548/165; 549/445

(58) Field of Classification Search ........... 514/301, 514/302; 548/165; 549/445
See application file for complete search history.

(56) References Cited

U.S. PATENT DOCUMENTS 6,770,663 B2   8/2004   Wagle et al.

FOREIGN PATENT DOCUMENTS

| JP | 7-112975 A | 5/1995 |
|---|---|---|
| JP | 2001-163861 A | 6/2001 |
| JP | 2003-524010 A | 8/2003 |
| WO | WO 96/03387 A1 | 2/1996 |
| WO | WO 99/03837 A1 | 1/1999 |
| WO | WO 00/61576 A1 | 10/2000 |
| WO | WO 01/44203 A1 | 6/2001 |
| WO | WO 01/62756 A1 | 8/2001 |
| WO | WO 01/72737 A1 | 10/2001 |
| WO | WO 01/85723 A1 | 11/2001 |
| WO | WO 02/40468 A | 5/2002 |
| WO | WO 02/076494 A2 | 10/2002 |
| WO | WO 03/042207 A1 | 5/2003 |
| WO | WO 03/062215 A1 | 7/2003 |
| WO | WO 03/080592 A1 | 10/2003 |
| WO | WO 03/087304 A2 | 10/2003 |
| WO | WO 2004/005264 A2 | 1/2004 |

OTHER PUBLICATIONS

Tsutomu Soma et al., <<Analysis of Apoptotic Cell Death in Human Hair Follicles In Vivo and In Vitro , The Journal of Investigative Dermatology Inc., Apoptosis in Human Hair, vol. 111, No. 6, pp. 948-954, (Dec. 1998)>>.
Kerstin Foitzik et al., "Control of murine hair follicle regression (catagen) by TGF-β1 in vivo", The FASEB Journal, vol. 14, pp. 752-760, (Apr. 2000).

*Primary Examiner*—Taofiq A Solola
(74) *Attorney, Agent, or Firm*—Sughrue Mion, PLLC

(57) ABSTRACT

A thiazolylimidazole derivative represented by the formula

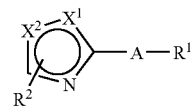

or a pharmaceutically acceptable salt thereof, and an ALK5 inhibitor, an therapeutic agent for alopecia or a hair growth agent having the above as an active ingredient,
wherein:
$X^1$ and $X^2$ are different from each other and represent a sulfur atom or a carbon atom; $R^1$ represents a phenyl group; a substituted phenyl group; a phenyl group condensed with a hetero aromatic ring; a pyridyl group; or a pyridyl group condensed with a hetero aromatic ring; $R^2$ represents a hydrogen atom, a halogen atom, an alkyl group having 1 to 6 carbon atoms, an alkyl group having 1 to 6 carbon atoms substituted with 1 to 5 halogen atoms, an alkoxy group having 1 to 6 carbon atoms, an alkanoyl group having 1 to 5 carbon atoms, or a hydroxyalkyl group having 1 to 6 carbon atoms, A represents a group which is represented by the formula.

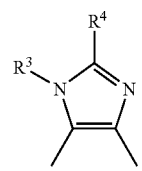

The present invention provides an inhibitory substance against ALK5 which is a TGF-β type I receptor and provides a hair growth stimulant or a hair growth agent based on its novel activities.

8 Claims, 1 Drawing Sheet

THIAZOLE DERIVATIVE

TECHNICAL FIELD

The present invention relates to a compound having an inhibitory action on activin receptor-like kinase 5 (ALK5) which is a TGF-β type I receptor. The present invention also relates to a hair follicle cell growth accelerator, a hair growth stimulant, and a hair growth agent, each of which contains a functional inhibitor of ALK5 as an active ingredient.

BACKGROUND ART

Transforming growth factory (TGF-β), as well as activin, BMP and the like, is a molecular entity belonging to a TGF-β superfamily. There are two distinct signaling receptors for TGF-β (type I and type II), both of which have serine/threonine kinase regions in their respective cells. Upon combining the TGF-β with the receptor, the type I receptor is phosphorylated by the type II receptor and thus activated, so that the signal is transferred to a nucleus via a Smad2/3 pathway or a TAB1/TAK1 pathway.

It has been apparent that the TGF-β has quite a lot of physiological actions, and as one of such actions, it has been well known that the TGF-β has a property of accumulating extracellular matrix in tissues through production stimulation and decomposition suppression of proteins which constitute the extracellular matrix (Massague, Ann Rev Cell Biol 6, 597-641 (1990)). Thus, continuous hyperproduction of TGF-β and activation of signal transduction system may lead to various fibrosing diseases. In the case of kidney, for example, TGF-β has been shown to be deeply involved in fibrosis or glomerulonephritis in renal disease such as glomerulonephritis or diabetic nephropathy (Okuda et al., J Clin Invest 86, 453-462 (1990), Border et al., Nature 346, 371-374 (1990)), and in the case of liver, TGF-β has been shown to facilitate production of extracellular matrix in the nonparenchymal cells and then contribute to the onset of hepatic fibrosis and liver cirrhosis (Barnard et al., Biochim Biophys Acta 1032, 79-87 (1990)). In addition, one of the causes of such intractable diseases as pulmonary fibrosis or proliferative vitreoretinopathy accompanied by substantial fibrosis is accumulation of extracellular matrix due to hyper function of TGF-β.

An inhibitor of ALK5 has been reported to suppress the accumulation of extracellular matrix induced by TGF-β by way of blocking TGF-β/Smad signals (Grygielko et al., ASN 2002 F-FC022), so that this inhibitor is considered to be useful as pharmaceutical products for treatment or prevention of various diseases associated with fibrosis of kidney, liver or lung, etc.

On the other hand, TGF-β is known to exhibit significant growth inhibitory action against various cells such as epithelial cells, vascular endothelial cells, hematocytes, or lymphocytes (Soma et al., J Invest Dermatol 111, 948-954 (1998)). As for hair follicles, it has been reported that TGF-β hyperexpression induces growth suppression/apoptosis in the hair follicle cells and then a hair cycle is shifted from anagen to telogen, and thus it has become apparent that TGF-β is deeply involved in progression of alopecia (Foitzik et al., FASEB J 14, 752-760 (2000)).

However, research has not fully shown that which signaling pathway from the TGF-β receptor primarily contributes to the growth suppression/apoptosis in the hair follicle cells, and thus prevention/treatment effect of alopecia which is based on blockade of TGF-β/Smad signals caused by the ALK5 inhibitor has not yet been reported.

Although substances having inhibitory action on activin receptor-like kinase 5 (ALK5) which is a TGF-β type I receptor are described in WO00/61576A, WO01/72737A, WO01/62756A, WO02/40468A, WO03/87304A and the like, a thiozolylimidazole compound according to the present invention has not been shown.

Further, although an imidazole compound having a similar structure to that of a compound according to the present invention is well known from WO99/03837A, WO96/03387A, WO03/62215A, WO01/85723A, WO01/44203A, JP2001163861A, JP07112975A, U.S. Pat. No. 6,770,663, WO04/005264A and the like, the inhibitory action of these compounds against activin receptor-like kinase 5 (ALK5) has not yet been reported.

DISCLOSURE OF THE INVENTION

It is an object of the present invention to provide a hair growth stimulant or a hair growth agent, which is based on the provision of an inhibitory substance against ALK5 which is a TGF-β type I receptor and the novel action thereof.

As a result of conducting various investigations in order to solve the problems, the present inventors have found that the ALK5 inhibitor inhibits the growth suppression of hair follicle cells due to TGF-β, and then also found that a certain kind of novel compound group inhibits the ALK5, and further have found an intermediate for producing the above described compound group to achieved the above-titled present invention.

That is, the present invention is a thiazole derivative represented by formula (I)

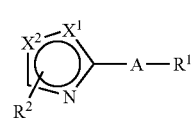

(I)

or a pharmaceutically acceptable salt thereof, wherein:

$X^1$ and $X^2$ are different from each other and represent a sulfur atom or a carbon atom;

$R^1$ represents a phenyl group;

a phenyl group substituted with 1 to 5 members selected from the group consisting of halogen atoms, alkyl groups having 1 to 6 carbon atoms, alkoxy groups having 1 to 6 carbon atoms, a hydroxy group, phenylalkoxy groups having 7 to 12 carbon atoms, and alkylamino groups having 1 to 6 carbon atoms;

a phenyl group condensed with a 5 to 7 membered hetero aromatic or non-aromatic ring having at least one hetero atom selected from the group consisting of N, O, and S;

a pyridyl group;

a quinolyl group;

an isoquinolyl group; or a pyridyl group condensed with a 5 to 7 membered hetero aromatic ring having at least one hetero atom selected from the group consisting of N, O, and S;

$R^2$ represents a hydrogen atom, a halogen atom, an alkyl group having 1 to 6 carbon atoms, an alkyl group having 1 to 6 carbon atoms substituted with 1 to 5 halogen atoms, an alkoxy group having 1 to 6 carbon atoms, an alkanoyl group having 1 to 6 carbon atoms, or a hydroxyalkyl group having 1 to 5 carbon atoms; and A represents a group which is represented by the formula

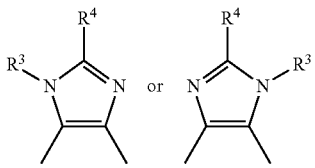

wherein:

R³ represents a hydrogen atom;
a hydroxy group;
an alkyl group having 1 to 6 carbon atoms;
a phenylalkyl group having 7 to 12 carbon atoms; or
a phenylalkyl group having 7 to 12 carbon atoms, substituted with a hydroxy group, an alkoxy group having 1 to 6 carbon atoms, an alkoxy group having 1 to 6 carbon atoms substituted with an alkoxy group having 1 to 6 carbon atoms, or an alkoxy group having 1 to 6 carbon atoms substituted with an alkylamino group having 1 to 6 carbon atoms, R⁴ represents a phenyl group;
a phenyl group substituted with 1 to 5 members selected from the group consisting of halogen atoms, alkyl groups having 1 to 6 carbon atoms, alkoxy groups having 1 to 6 carbon atoms, a carbamoyl group, and a cyano group;
a hydrogen atom;
an alkyl group having 1 to 12 carbon atoms;
an alkenyl group having 2 to 12 carbon atoms;
a cycloalkyl group having 3 to 7 carbon atoms;
an alkyl group having 1 to 12 carbon atoms substituted by an alkoxy group having 1 to 6 carbon atoms, a hydroxy group, an alkoxyphenylalkoxy group having 8 to 12 carbon atoms, a phthalimidoyl group, a toluenesulfonyloxy group, or a morpholino group;
an alkyl group having 1 to 6 carbon atoms substituted with 1 to 5 halogen atoms;
a cycloalkyl group having 3 to 9 carbon atoms substituted with an oxo group;
a tetrahydropyranyl group;
a 4-piperidinyl group;
a piperidinyl group substituted with an alkyl group having 1 to 6 carbon atoms or a t-butoxycarbonyl group;
a cyclohexanespiro-2'-(1,3-dioxoranyl) group;
a pyrrolidin-2-one-5-yl group;
a group represented by the formula —Y¹—Z¹—NR⁵—Z²—Y²—R⁶,
wherein:
Y¹ and Y² are the same or different from each other and represent a single bond or an alkylene group having 1 to 12 carbon atoms;
R⁵ represents a hydrogen atom or an alkyl group having 1 to 12 carbon atoms;
Z¹ and Z² are the same or different from each other and represent a single bond;
an alkylene group having 1 to 7 carbon atoms;
—CO—;
—CO₂—;
—SO₂—; or
—OCO—, and
R⁶ represents
a cycloalkyl group having 3 to 7 carbon atoms;
an alkyl group having 1 to 6 carbon atoms substituted with 1 to 3 halogen atoms;
an alkenyl group having 2 to 6 carbon atoms;
an alkynyl group having 2 to 6 carbon atoms;
an amino group;
an amino group substituted with 1 to 2 groups selected from the group consisting of an alkyl group having 1 to 6 carbon atoms, a cycloalkyl group having 3 to 7 carbon atoms, and a t-butoxycarbonyl group;
a piperidino group;
a piperidinyl group;
a piperidinyl group substituted with an alkyl group having 1 to 6 carbon atoms;
a pyrrolidinyl group;
a piperazinyl group;
a piperazinyl group substituted with an alkyl group having 1 to 6 carbon atoms;
a morpholino group;
a hydroxy group;
an alkoxy group having 1 to 6 carbon atoms;
an alkoxy group having 1 to 6 carbon atoms substituted by a hydroxy group or an alkoxy group having 1 to 6 carbon atoms;
an oxetan-2-yl group;
a tetrahydrofuranyl group;
a tetrahydropyranyl group;
a hydrogen atom;
a phenyl group;
a phenyl group substituted with an alkoxy group having 1 to 4 carbon atoms; or
a group that forms a ring when linked to the nitrogen atom of the above formula; or
a group represented by the formula —Y³—CO—R⁴¹,
wherein:
Y³ represents a single bond or an alkylene group having 1 to 7 carbon atoms,
R⁴¹ represents
a hydroxy group;
an alkoxy group having 1 to 6 carbon atoms;
a piperidino group;
a piperazin-1-yl group substituted by an alkyl group having 1 to 6 carbon atoms, a morpholinoalkyl group having 5 to 10 carbon atoms, or an alkylaminoalkyl group having 2 to 14 carbon atoms; or
a morpholino group.

Another embodiment of the present invention is an ALK5 inhibitor which contains the above described thiazolylimidazole derivative or a pharmaceutically acceptable salt thereof as an active ingredient.

In addition, another embodiment of the present invention is a hair growth agent which contains, as an active ingredient, a substance for inhibiting a function of ALK5 being involved in signal transduction of TGF-β, and thus the present invention provides a completely new concept in which an action mechanism is different from that of the conventional hair growth agent.

Further, another embodiment of the present invention is an intermediate for producing a compound represented by the formula (I), in which a portion corresponding to A of the above described formula (I) represents groups as described below,

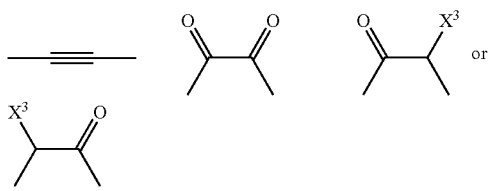

wherein $X^3$ represents a hydrogen atom or a halogen atom.

Preferable compounds of formula (I) according to the present invention includes a compound in which $R^2$ is a hydrogen atom, a halogen atom, an alkyl group having 1 to 6 carbon atoms, or an alkyl group having 1 to 6 carbon atoms substituted with 1 to 5 halogen atoms, more preferably a compound in which $R^2$ is an alkyl group having 1 to 6 carbon atoms or a trifluoromethyl group and yet more preferably a compound in which $R^2$ is a methyl group, or a trifluoromethyl group.

The compounds wherein $R^1$ is a phenyl group condensed with a 5 to 7 membered hetero aromatic or non-aromatic ring containing at least one hetero atom selected from the group consisting of N, O, and S are preferable. The compounds wherein $X^1$ is a sulfur atom and $X^2$ is a carbon atom are also preferable.

Although the term "a hair growth agent" as used herein means a pharmaceutical product or a quasi drug which is used for the purpose of induction of hair growth, stimulation of hair growth, or prevention of alopecia, this term is required to be taken in the broad sense and should not be used exclusively in any sense. When a hair growth agent according to the present invention is used as a pharmaceutical product, this is applicable to amelioration or prevention of alopecia areata or male pattern alopecia for example, but application of the hair growth agent according to the present invention is not limited thereto.

The present invention shows that the substance, which inhibits the function of ALK5, acts as an ameliorating agent or a prophylactic drug against hypofunction of hair follicle cells.

The substance which inhibits the function of ALK5 is a substance which suppresses phosphorylation of Samd2 and Smad3 when a signal is transmitted from a TGF-β receptor, and for example, illustrative compounds are described in claims 1 to 6 of the present invention. Since the above described action mechanism can completely inhibit the growth suppression effect of TGF-β against the hair follicle cells which are also hair keratin production cells, it is expected that this substance is effective for symptoms that have not been ameliorated or prevented by the conventional hair growth agent.

In addition, it is also expected that this substance produces a synergic effect in combination with other hair growth stimulants or hair growth agents having other efficacy.

Although the hair growth agent according to the present invention can be administered in different dosage amounts and in different dosage forms depending on natures of substances, it is preferable that this substance is externally applied or orally administered because of its necessity of continuous administration. Not all of such dosage amounts can be expressed in numerical values uniformly. However, as for compounds 1 to 202 and 228 to 249, it may be necessary to administer about 0.0001 to 10 wt % thereof, preferably 0.001 to 5 wt % thereof, and more preferably 0.001 to 1 wt % thereof as a lotion, an ointment, or a gel for external application, or alternatively, it may be necessary to administer about 1 to 100 mg/kg of such compound as a powdered drug or a capsule for oral administration. The above described formulations can be obtained by using common formulation techniques.

A dosage form of the hair growth agent according to the present invention is not specifically limited to a certain form, but in the case of an external preparation, a hair growth agent containing an ALK5 inhibitor such as any of compounds 1 to 202 and 228 to 249 as an active ingredient is preferably provided as a water soluble composition. Generally, in order to produce such a water soluble composition, various additives (humectants, thickeners, preservatives, antioxidants, flavors, and colorants etc.) used for manufacturing medicines, quasi drugs, or cosmetics can be used. The hair growth agent according to the present invention can be provided as a hair trimming composition such as a hair drug, hair oil, hair mousse, or gel, a hair washing composition such as a shampoo or rinse, or alternatively an ointment for example.

When a hair growth agent according to the present invention is provided as a liquid drug, an ALK5 inhibitor such as any of compounds 1 to 202 and 228 to 249 is adequately combined with purified water, a suitable buffer solution such as a phosphate buffer, a physiological saline solution such as saline, a Ringer's solution or a Lock solution, ethanol, glycerin, and a commonly used surfactant in order to prepare the drug in the form of a sterilized aqueous solution, non-aqueous solution, suspension, liposome, or emulsion. This preparation is topically administered as a liquid preparation for scalp. In this case, the liquid preparation may be directly applied onto the scalp or may be applied by using an injection nozzle for spraying.

When a hair growth agent according to the present invention is provided as a semisolid preparation, an ALK5 inhibitor such as any of compounds 1 to 202 and 228 to 249 can be admixed with fat, fatty oil, lanoline, Vaseline, paraffin, wax, ointment, resin, plastic, glycols, higher alcohol, glycerin, water, emulsifiers, suspending agents or the like, and then topically administered as an external medicine such ointment or cream.

When a hair growth agent according to the present invention is provided as a solid preparation, an ALK5 inhibitor such as any of compounds 1 to 202 and 228 to 249 can be mixed appropriately with a suitable additive to prepare an external medicine such as a powdered drug or a dust formulation, or alternatively, the inhibitor can be dissolved or suspended in a solvent if required in order to prepare a solid formulation for the scalp application.

Further, in the case of oral administration, an ALK5 inhibitor such as any of compounds 1 to 202 and 228 to 249 can be blended with a pharmaceutically acceptable carrier (excipients, binders, disintegrants, flavoring substances, aromatizing agents, and emulsifiers, etc.), diluent, solubilizing agent or the like, and thus obtained pharmaceutical product is preferably provided as a tablet, capsule, granule, powdered drug, syrup, suspension, solution or the like which can be prepared in accordance with the common technique.

In the present invention, a halogen atom is a fluorine atom, a chlorine atom, a bromine atom, or an iodine atom.

An alkyl group having 1 to 6 carbon atoms means a linear or branched chain saturated alkyl group having 1 to 6 carbon atoms, and includes for example a methyl group, an ethyl group, a n-propyl group, an isopropyl group, a n-butyl group, an isobutyl group, a tert-butyl group, a sec-butyl group, a n-pentyl group, an isopentyl group, a neopentyl group, a tert-pentyl group, and a n-hexyl group.

An alkoxy group having 1 to 6 carbon atoms means a linear or branched chain alkyloxy group having 1 to 6 carbon atoms, and includes for example a methoxy group, an ethoxy group, a propoxy group, an isopropoxy group, a butoxy group, an isobutoxy group, a sec-butoxy group, a tert-butoxy group, a pentyloxy group, and a hexyloxy group.

A phenylalkoxy group of 7 to 12 carbon atoms means a phenylalkoxy group having 7 to 12 carbon atoms, and includes for example a benzyloxy group and a phenethyloxy group.

An alkylamino group having 1 to 6 carbon atoms means a linear or branched chain mono- or di-alkylamino group having 1 to 6 carbon atoms, and includes for example a methylamino group, an ethylamino group, and a N,N-dimethylamino group.

A phenyl group condensed with a 5 to 7 membered hetero aromatic or non-aromatic ring having at least one hetero atom selected from the group consisting of N, O, and S includes, for example, a benzothiazolyl group, a benzoxazolyl group, and a benzo(1,3)dioxolyl group.

A pyridyl group condensed with a 5 to 7 membered hetero aromatic ring having at least one hetero atom selected from the group consisting of N, O, and S includes, for example, a pyrazolopyridyl group, an imidazopyridyl group, and a triazolopyridyl group.

An alkanoyl group having 1 to 6 carbon atoms means a linear or branched chain alkanoyl group having 1 to 6 carbon atoms, and includes for example a formyl group, an acetyl group, a propionyl group, a butyryl group, an isobutyryl group, a valeryl group, a hexanoyl group, and a pivaloyl group.

A hydroxyalkyl group having 1 to 5 carbon atoms means a linear or branched chain hydroxyalkyl group having 1 to 5 carbon atoms, and includes for example a hydroxymethyl group, a 1-hydroxyethyl group, and a 2-hydroxyethyl group.

A phenylalkyl group of 7 to 12 carbon atoms means a phenylalkyl group having 7 to 12 carbon atoms, and includes for example a benzyl group and a phenethyl group.

An alkyl group having 1 to 12 carbon atoms means a linear or branched chain saturated alkyl group having 1 to 12 carbon atoms, and includes for example a methyl group, an ethyl group, a n-propyl group, an isopropyl group, a n-butyl group, an isobutyl group, a tert-butyl group, a sec-butyl group, a n-pentyl group, an isopentyl group, a neopentyl group, a tert-pentyl group, a 1-ethyl-propyl group, a n-hexyl group, and a n-dodecyl group.

An alkenyl group having 2 to 12 carbon atoms means a linear or branched chain alkenyl group having 2 to 12 carbon atoms, and includes for example a vinyl group, a 1-propenyl group, an allyl group, an isopropenyl group, a butenyl group, an isobutylenyl group, a hexenyl group, and a dodecenyl group.

A cycloalkyl group of 3 to 7 carbon atoms means a cycloalkyl group having 3 to 7 carbon atoms, and includes for example a cyclopropyl group, a cyclobutyl group, a cyclopentyl group, and a cyclohexyl group.

An alkoxyphenylalkoxy group having 8 to 12 carbon atoms means a phenylalkoxy group having 8 to 12 carbon atoms in which a benzene ring is substituted with an alkoxy group, and includes for example a 4-methoxybenzyloxy group and a 4-methoxyphenethyloxy group.

A cycloalkyl group having 3 to 9 carbon atoms substituted with an oxo group means on a cycloalkyl group having 3 to 9 carbon atoms substituted with an oxo group on the ring, and includes for example an 4-oxocyclohexyl group.

A tetrahydropyranyl group includes for example a 2-tetrahydropyranyl group, a 3-tetrahydropyranyl group, and an 4-tetrahydropyranyl group.

An alkylene group having 1 to 12 carbon atoms means a linear or branched chain alkylene group having 1 to 12 carbon atoms, and includes for example a methylene group, an ethylene group, a trimethylene group, a tetramethylene group, a pentamethylene group, a hexamethylene group, and a dodecamethylene group.

An alkylene group having 1 to 7 carbon atoms means a linear or branched chain alkylene group having 1 to 7 carbon atoms, and includes for example a methylene group, an ethylene group, a trimethylene group, a tetramethylene group, a pentamethylene group, a hexamethylene group, and a heptamethylen group.

An alkenyl group having 2 to 6 carbon atoms means a linear or branched chain alkenyl group having 2 to 6 carbon atoms, and includes for example a vinyl group, a 1-propenyl group, an allyl group, an isopropenyl group, a butenyl group, an isobutylenyl group, and a hexenyl group.

An alkynyl group having 2 to 6 carbon atoms means a linear or branched chain alkynyl group having 2 to 6 carbon atoms, and includes for example an ethynyl group, a 1-propynyl group, and a 2-propynyl group.

A piperidinyl group includes for example a 2-piperidinyl group, a 3-piperidinyl group, and a 4-piperidinyl group.

A pyrrolidinyl group includes for example a 2-pyrrolidinyl group, a 3-pyrrolidinyl group, and a 4-pyrrolidinyl group.

A piperazinyl group includes for example a 2-piperazinyl group and a 3-piperazinyl group.

A tetrahydrofuranyl group includes for example a 2-tetrahydrofuranyl group and a 3-tetrahydrofuranyl group.

A phenyl group substituted by an alkoxy group having 1 to 4 carbon atoms includes for example a 4-methoxyphenyl group.

A morpholinoalkyl group having 5 to 10 carbon atoms means a linear or branched chain alkyl group having 1 to 6 carbon atoms substituted with a morpholino group, and includes for example a morpholinomethyl group, a 1-morpholinoethyl group, and a 2-morpholino ethyl group.

An alkylaminoalkyl group having 2 to 14 carbon atoms means a linear or branched chain alkyl group having 1 to 6 carbon atoms substituted with a linear or branched chain mono- or di-alkylamino group having 1 to 4 carbon atoms, and includes for example an N-methylaminomethyl group, an N-ethylaminomethyl group, an N,N-dimethylaminomethyl group, and an N,N-dimethylaminoethyl group.

An alkyl group having 1 to 6 carbon atoms substituted with 1 to 5 halogen atoms means a linear or branched chain alkyl group having 1 to 6 carbon atoms substituted with 1 to 5 halogen atoms, and include for example a chloromethyl group, a trifluoromethyl group, and a pentafluoroethyl group.

In addition, the pharmaceutically acceptable salt is a salt with alkali metal, alkaline earth metal, ammonium, alkylammonium or the like, or alternatively a salt with an inorganic acid or an organic acid. Examples of the above described salt include a sodium salt, potassium salt, calcium salt, ammonium salt, aluminum salt, triethylammonium salt, acetate, propionate, butyrate, formate, trifluoroacetate, maleate, tartrate, citrate, stearate, succinate, ethylsuccinate, lactobionate, gluconate, glucoheptonate, benzoate, methanesulfonate, ethanesulfonate, 2-hydroxyethanesulfonate, benzenesulfonate, para-toluenesulfonate, laurylsulfate, malate, aspartate, glutamate, adipate, salt with cysteine, salt with N-acetylcysteine, hydrochloride, hydrobromide, phosphate, sulfate, hydroiodide, nicotinate, oxalate, picrate, thiocyanate, undecanoate, salt with acrylic polymer, and salt with carboxyvinyl polymer.

BEST MODE FOR CARRYING OUT THE INVENTION

Figure 1:
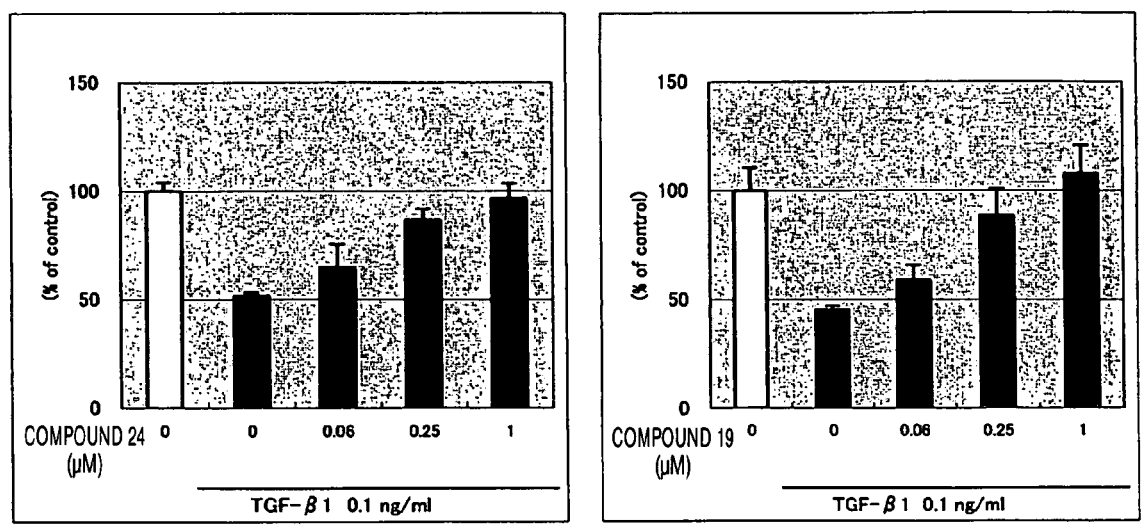
FIG. 1 shows two graphs measuring the number of living cells when TGF-β1 was solely administered and when TGF-β1 and the compound of the present invention were simultaneously administered. The number of living cells at 72 hours in the absence of adding TGF-β1 is taken as 100%.

A compound according to the present invention can be synthesized by a method as described below, for example. That is, a coupling reaction of a compound represented by formula (a)

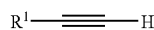 (a)

(wherein R¹ has the same definition as above.) with a compound represented by formula (b)

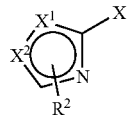 (b)

(wherein X¹, X², and R² have the same definitions as above, and X represents a halogen atom.) can be carried out in a solvent in the presence of a catalyst such as tetrakis(triphenylphosphine)palladium and a base to synthesize a compound of the present invention represented by formula (c)

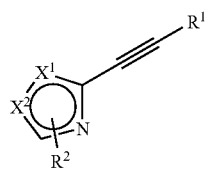 (c)

(wherein X¹, X², R¹, and R² have the same definitions as above.).

In addition, the resultant compound (c) can be oxidized, for example, by a method in which the compound (c) is exposed to palladium(II) chloride in dimethyl sulfoxide or by a method in which the compound (c) is exposed to potassium permanganate in an acetone-buffer solution to synthesize a compound of the present invention represented by formula (d)

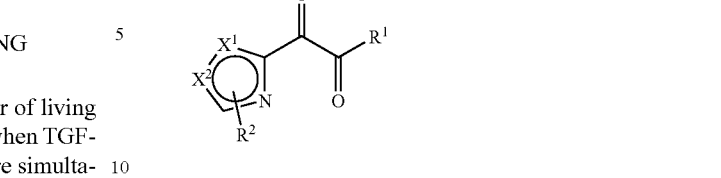 (d)

(wherein X¹, X², R¹, and R² have the same definitions as above.).

In addition, a reaction of a compound represented by formula (e)

R⁴—CHO (e)

(wherein R⁴ has the same definition as above.) with ammonium acetate can be carried out in a solvent to synthesize a compound of the present invention represented by formula (f)

(f)

(wherein X¹, X¹, R¹, R², and R⁴ have the same definitions as above.).

Alternatively, a compound according to the present invention can also be synthesized by a following method for example. That is, a reaction of a compound represented by formula (g)

(g)

(n = 1, 2, 3)

(wherein R³ has the same definition as above.) with the above described formula (d) and ammonium acetate can be carried out in a solvent to synthesize a compound of the present invention represented by formula (f)

(f)

(wherein X¹, X², R¹, R², and R⁴ have the same definitions as above.).

In addition, a compound according to the present invention can also be synthesized by a following method, for example. That is, a compound represented by formula (c)

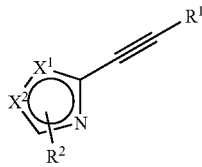
(c)

(wherein $X^1$, $X^2$, $R^1$, and $R^2$ have the same definitions as above.) can be hydrated by treatment with mercury (II) sulfate and sulfuric acid in a solvent for example, to synthesize a compound of the present invention represented by formula (h) or (i),

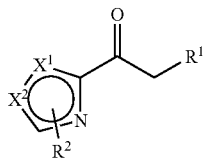
(h)

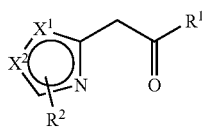
(i)

(wherein $X^1$, $X^2$, $R^1$, and $R^2$ have the same definitions as above.) or a mixture of the above described formula (h) and the above described formula (i). Further, the formula (h) or the formula (i) or the mixture of formulae (h) and (i) can be treated with sodium nitrite in an aqueous hydrochloric acid solution for example to obtain a compound represented by formula (j) or formula (k)

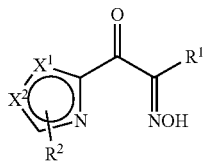
(j)

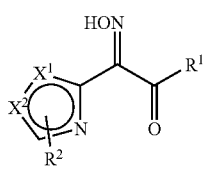
(k)

(wherein $X^1$, $X^2$, $R^1$, and $R^2$ have the same definitions as above.) or a mixture of the above described formula (j) and (k), and further, treated with a compound represented by formula (e)

R⁴—CHO (e)

(wherein $R^4$ has the same definition as above.) and ammonium acetate in a solvent. Then the resultant composition is then reduced with triethyl phosphite or the like optionally in a solvent to obtain a compound of the present invention represented by formula (f)

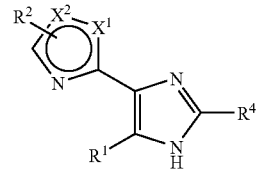
(f)

(wherein $X^1$, $X^2$, $R^1$, $R^2$, and $R^4$ have the same definitions as above.).

A compound according to the present invention can also be synthesized by a following method, for example. That is, using a method in which a compound represented by formula (l)

R¹—CH₂CO₂H (l)

(wherein $R^1$ has the same definition as above.) is reacted with N,O-dimethylhydroxylamine via acid halide in a solvent or condensed with N,O-dimethylhydroxylamine in the presence of a condensing agent such as 1-ethyl-3-(3-dimethylaminopropyl)-carbodiimide hydrochloride, a compound represented by formula (m)

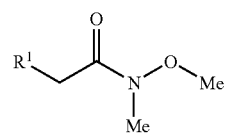
(m)

(wherein $R^1$ has the same definition as above.) can be obtained, and then a compound represented by formula (n)

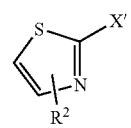
(n)

(wherein $R^2$ has the same definition as above, and X' represents a halogen atom or a hydrogen atom.) is reacted with a base such as n-butyllithium in a solvent. The resultant anion can be allowed to react with the above described formula (m) to synthesize a compound of the present invention represented by formula (o)

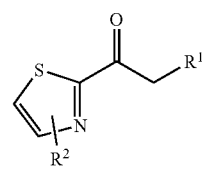
(o)

(wherein R¹ and R² have the same definitions as above.). Further, the formula (o) can be halogenated by copper (II) bromide in a solvent to synthesize a compound of the present invention represented by formula (p)

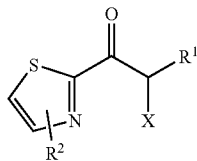
(p)

(wherein R¹ and R² have the same definitions as above, and X represents a halogen atom.). Subsequently, the compound represented by formula (p) is allowed to react with a compound represented by formula (q)

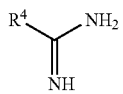
(q)

(wherein R⁴ has the same definition as above.) in a solvent to synthesize a compound of the present invention represented by formula (r)

(r)

(wherein R¹, R², and R⁴ have the same definitions as above.). In addition, the compound represented by formula (r) is allowed to react with a compound represented by formula (s)

R³—X"  (s)

(wherein R³ has the same definition as above, and X" represents a halogen atom.) in a solvent in the presence of a base such as sodium hydride, and then a compound of the present invention represented by formula (t) or formula (u)

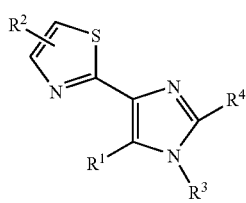
(t)

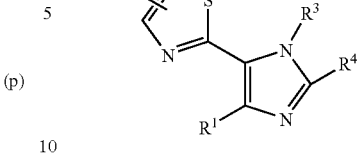
(u)

(wherein R¹, R², R³, and R⁴ have the same definitions as above.) or a mixture of the above described formulas (t) and (u) can be synthesized.

A compound according to the present invention can also be synthesized by interchange of R¹, R², R³, and R⁴ in the compounds of the present invention obtained by the above described methods.

Examples of the base used for the above described reactions are: salt of alkali metals such as sodium carbonate, potassium carbonate, sodium hydrogen carbonate, potassium hydrogen carbonate, sodium hydroxide, dimsyl sodium, sodium hydride, sodium amide, and tert-butyl potassium; amines such as triethylamine, diisopropylamine, pyrrolidine, and piperidine; sodium acetate, and potassium acetate. As the reaction solvent, a solvent which is inert during the course of the reaction can be used, and includes water; alcohols such as methanol, ethanol, isopropylalcohol, and tert-butylalcohol; ethers such as dioxane and tetrahydrofyran; dimethylformamide, dimethylsulfoxide, pyridine, methylene chloride, chloroform, acetone, and acetic acid.

EXAMPLES

The present invention will now be described in more detail with reference to Examples and Test Examples.

Example 1

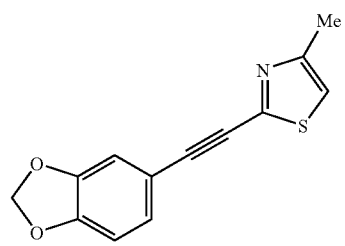

Synthesis of Compound 217

Triethylamine (25 ml), tetrakis(triphenylphosphine)palladium (642 mg), and 5-ethynyl-benzo(1,3)dioxole (1.79 g) were added to a solution of 2-iodo-4-methylthiazole (2.50 g) in acetonitrile (50 ml), and then the mixture was stirred for 4 hours under reflux condition. After the solvent was evaporated, the resultant residue was purified by silica gel flash column chromatography using a mixed solvent of ethyl acetate and chloroform and hexane to yield the title compound (2.38 g).

¹H-NMR (300 MHz, CDCl₃) δ ppm:

2.49 (3H, d, J=0.9 Hz), 6.01 (2H, s), 6.81 (1H, d, J=8.1 Hz), 6.91 (1H, d, J=0.9 Hz), 7.01 (1H, d, J=1.6 Hz), 7.13 (1H, dd, J=8.1, 1.6 Hz) mp: 111.5-112.0° C.

Example 2

Synthesis of Compound 203

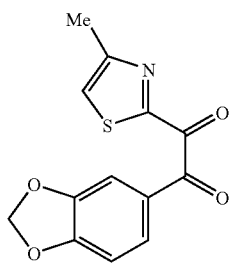

Palladium(II) chloride (139 mg) was added to a solution of Compound 217 (1.91 g) in dimethylsulfoxide (13 ml), and then the mixture was stirred for 3 hours at 125° C. This solution was diluted with ethyl acetate and then filtered, the resultant solution was washed with water and a brine successively. An organic layer was dried over anhydrous magnesium sulfate and then the solvent was evaporated. The resultant residue was purified by silica gel flash column chromatography using a mixed solvent of ethyl acetate and hexane to yield the title compound (960 mg).

¹H-NMR (300 MHz, CDCl₃) δ ppm 2.52 (3H, d, J=0.9 Hz), 6.09 (2H, s), 6.88 (1H, d, J=8.7 Hz), 7.40 (1H, d, J=0.9 Hz), 7.48-7.54 (2H, m) mp: 131.5-132.5° C.

Example 3

Synthesis of Compound 8

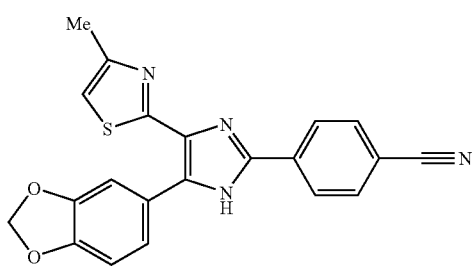

Ammonium acetate (1.50 g) was added to a solution of Compound 203 (893 mg) and 4-cyanobenzaldehyde (510 mg) in acetic acid (40 ml), and then the mixture was stirred for 4 hours under reflux condition. After the solvent was evaporated, the solution was neutralized with aqueous ammonia and extracted twice with chloroform. An organic layer was dried over anhydrous magnesium sulfate and then the solvent was evaporated. The resultant residue was purified by recrystallization from methanol and chloroform to yield the title compound (575 mg).

¹H NMR (300 MHz, DMSO-d6) δ ppm:

2.36 (3H, s), 6.10 (2H, s), 7.06 (1H, d, J=7.6 Hz), 7.20 (1H, s), 7.55 (1H, bd, J=7.6 Hz), 7.73 (1H, bs), 7.97 (2H, d, J=8.3 Hz), 8.26 (2H, d, J=8.3 Hz), 13.05 (1H, brs)

Example 4

Synthesis of Compound 9

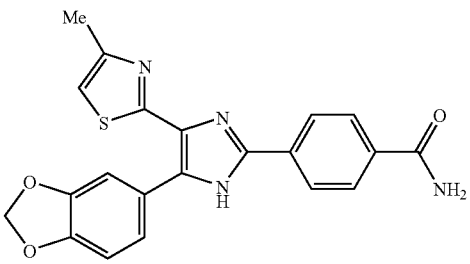

Potassium hydroxide (584 mg) was added to a solution of Compound 8 (575 mg) in tert-butanol (100 ml), and then the mixture was stirred overnight under reflux condition. After the solvent was evaporated, the solution was diluted with ethyl acetate and washed with water. An organic layer was dried over anhydrous magnesium sulfate and then the solvent was evaporated. The resultant residue was recrystallized from methanol to yield the title compound (556 mg).

¹H NMR (300 MHz, DMSO-d6) δ ppm:

2.36 (3H, s), 6.10 (2H, s), 7.05 (1H, d, J=8.1 Hz), 7.18 (1H, s), 7.42 (1H, brs), 7.58 (1H, bd, J=8.1 Hz), 7.75 (1H, bs), 7.94-8.08 (3H, m), 8.15 (2H, d, J=8.2 Hz), 12.87 (1H, brs) mp: 276.0-277.0° C.

Example 5

Synthesis of Compound 213

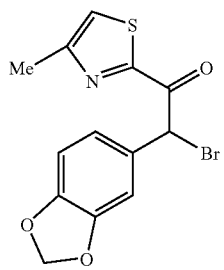

(1) Thionyl chloride (39.6 g) and a drop of dimethylformamide were added to a solution of benzo(1,3)dioxol-5-yl-acetic acid (30.0 g) in toluene (200 ml) and then the mixture was stirred for 2.5 hours at 60° C., after distilling out the solvent, to yield unpurified benzo(1,3)dioxol-5-yl-acetyl chloride. A solution of sodium hydroxide (20.0 g) in water (150 ml) was added to a solution of N,O-dimethylhydroxylamine hydrochloride (19.5 g) in toluene (200 ml) at 0° C., and further the unpurified benzo(1,3)dioxol-5-yl-acetyl chloride was added thereto, and then the mixture was stirred for 3 hours. The reaction mixture was extracted with toluene and dried over anhydrous magnesium sulfate, and from which the solvent was evaporated to yield unpurified 2-benzo(1,3)dioxol-5-yl-N-methoxy-N-methylacetoamide (35.4 g).

¹H NMR (200 MHz, CDCl₃) δ ppm:
3.19 (3H, s), 3.64 (3H, s), 3.67 (2H, s), 5.82 (2H, s), 6.71-6.83 (3H, m)

(2) A 2.6M solution of n-butylithium in hexane (34 ml) was dropped into a solution of 4-methylthiazole (8.0 g) of tetrahydrofuran (150 ml) at −70° C. and the mixture was stirred for 30 minutes. Further, a solution of 2-benzo(1,3)dioxol-5-yl-N-methoxy-N-methylacetamide (20.0 g) in tetrahydrofuran (20 ml) was dropped therein and the mixture was stirred for 1 hour. This solution, to which a saturated aqueous solution of ammonium chloride was added, was extracted with ethyl acetate, and after the organic layer was dried over anhydrous magnesium sulfate, the solvent was evaporated. The resultant residue was purified by silica gel flash column chromatography using a mixed solvent of ethyl acetate and hexane to yield 2-benzo(1,3)dioxol-5-yl-1-(4-methylthiazol-2-yl)ethanone (19.3 g).

¹H NMR (300 MHz, CDCl₃) δ ppm:
2.56 (3H, d, J=0.9 Hz), 4.34 (2H, s), 5.93 (2H, s), 6.76 (1H, d, J=7.8 Hz), 6.80 (1H, dd, J=7.8, 1.6 Hz), 6.86 (1H, d, J=1.6 Hz), 7.25 (1H, q, J=0.9 Hz)

(3) Copper (II) bromide (24.7 g) was added to a mixed solution of 2-benzo(1,3)dioxol-5-yl-1-(4-methylthiazol-2-yl)ethanone (19.3 g) in ethyl acetate (200 ml) and chloroform (200 ml), and the mixture was stirred for 3 hours under reflux condition. After filtration of the reaction mixture, the solvent was evaporated. The resultant residue was purified by silica gel flash column chromatography using a mixed solvent of ethyl acetate and chloroform to yield the title compound (8.96 g).

¹H NMR (300 MHz, CDCl₃) δ ppm:
2.54 (3H, d, J=0.9 Hz), 5.95-5.99 (2H, m), 6.75 (1H, d, J=8.1 Hz), 6.78 (1H, s), 7.09 (1H, dd, J=7.9, 1.9 Hz), 7.21 (1H, d, J=1.9 Hz), 7.32 (1H, q, J=0.9 Hz)

Example 6

Synthesis of Compound 20

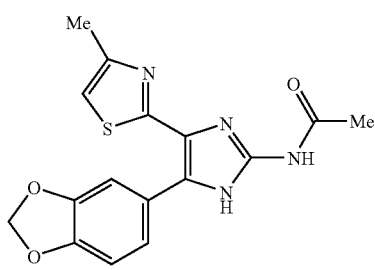

1-acetylguanidine (1.63 g) was added to a solution of Compound 213 (1.83 g) in acetonitrile (20 ml), and the mixture was stirred for 16 hours under reflux condition. After the solvent was evaporated, the solution was diluted with chloroform, and then washed with water and a brine successively. The organic layer was dried over anhydrous magnesium sulfate, and then the solvent was evaporated. The resultant residue was eluted with a mixed solvent of chloroform and hexane through the NH silica gel (Chromatorex, produced by Fuji Silysia Chemical LTD.) flash column chromatography. The residue from the eluate was recrystallized from a mixed solvent of ethyl acetate and hexane to yield the title compound (590 mg).

¹H NMR (300 MHz, DMSO-d6) δ ppm:
2.09 (3H, s), 2.34 (3H, d, J=0.9 Hz), 6.07 (2H, s), 6.98 (1H, d, J=8.2 Hz), 7.13 (1H, d, J=0.9 Hz), 7.45 (1H, dd, J=8.2, 1.7 Hz), 7.78 (1H, d, J=1.7 Hz), 11.28 (1H, bs), 11.76 (1H, bs) mp: 169.0-173.0° C.

Example 7

Synthesis of Compound 19

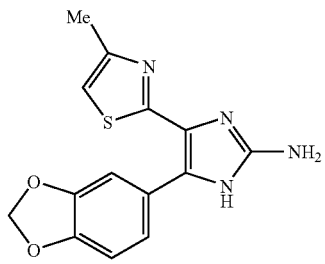

Concentrated sulfuric acid (0.58 ml) was added to a mixed solution of Compound 20 (578 mg) with methanol (10 ml) and water (10 ml), and the mixture was stirred for 3 hours under reflux condition. An aqueous solution of potassium hydroxide was added thereto in order to make this reaction solution alkaline, and then this solution was extracted three times with chloroform. After the organic layer was dried over anhydrous magnesium sulfate, the solvent was evaporated. The resultant residue was eluted with a mixed solvent of methanol and chloroform through the NH silica gel flash column chromatography. The residue from the eluate was recrystallized from a mixed solvent of chloroform and hexane to yield the title compound (260 mg)

¹H NMR (300 MHz, CDCl₃) δ ppm:
2.39 (3H, d, J=0.9 Hz), 6.00 (2H, s), 6.60 (1H, d, J=0.9 Hz), 6.84 (1H, d, J=7.9 Hz), 7.15 (1H, dd, J=7.9, 1.7 Hz), 7.19 (1H, d, J=1.7 Hz) mp: 205.5-208.0° C.

Example 8

Synthesis of Compound 21

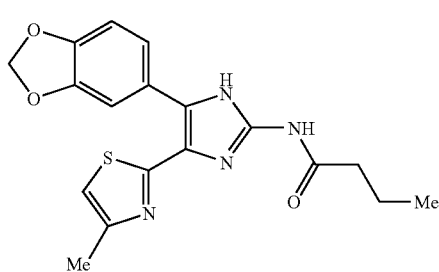

n-butylchloride (36 μl) was added to a solution of Compound 19 (70 mg) in pyridine (0.7 ml), and the mixture was stirred for 2.5 hours at room temperature. After the reaction mixture was diluted with ethyl acetate, this mixture was washed with a saturated aqueous solution of sodium hydrogen carbonate and a brine successively. The organic layer was dried over anhydrous magnesium sulfate, and then the solvent was evaporated. The resultant residue was purified by NH silica gel column chromatography using a chloroform solvent to yield the title compound (84 mg).

¹H NMR (300 MHz, DMSO-d6) δ ppm:
0.93 (3H, t J=7.3 Hz), 1.63 (2H, qt, J=7.3, 7.3 Hz), 2.28-2.41 (5H, m), 6.07 (2H, s), 6.98 (1H, d, J=8.1 Hz), 7.12 (1H, s), 7.46 (1H, brd, J=8.1 Hz), 7.79 (1H, brs), 11.25 (1H, brs), 11.78 (1H, brs)

Example 9

Synthesis of Compound 135

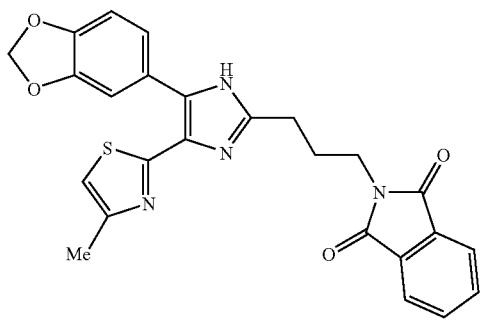

A solution of ammonium acetate (4.20 g) in methanol (55 ml) was added to a solution of Compound 203 (1.50 g) and 4-(1,3-dioxo-1,3-dihydroisoindol-2-yl)butylaldehyde (1.78 g) in tetrahydrofuran (55 ml), and the mixture was stirred for 2.5 hours under reflux condition. After the solvent was evaporated, the solution was diluted with chloroform and then washed with a saturated aqueous solution of sodium carbonate. The organic layer was dried over anhydrous magnesium sulfate, and then the solvent was evaporated. The resultant residue was purified by silica gel flash column chromatography using a mixed solvent of methanol and chloroform to yield the title compound (970 mg).

¹H NMR (300 MHz, DMSO-d6) δ ppm:
2.05-2.10 (2H, m), 2.32 (3H, d, J=0.8 Hz), 2.70 (2H, t, J=7.7 Hz), 3.70 (2H, t, J=6.8 Hz), 6.06 (2H, s), 6.98 (1H, d, J=8.2 Hz), 7.07 (1H, d, J=1.1 Hz), 7.46 (1H, dd, J=8.2, 1.9 Hz), 7.77-7.84 (5H, m), 12.19 (1H, s)

Example 10

Synthesis of Compound 29

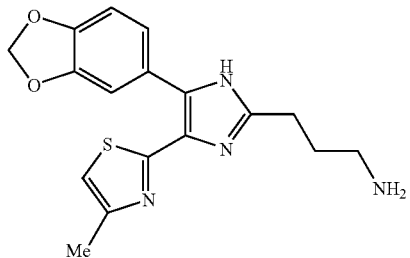

Hydrazine monohydrate (984 mg) was added to a solution of Compound 135 (928 mg) in ethanol (50 ml), and the mixture was stirred for 3 hours under reflux condition. After the solvent was evaporated, the resultant residue was purified by NH silica gel column chromatography using a mixed solvent of methanol and chloroform to yield the title compound (458 mg).

¹H NMR (200 MHz, CDCl₃) δ ppm:
1.90 (2H, tt, J=6.4, 6.4 Hz), 2.43 (3H, d, J=0.9 Hz), 2.84-3.01 (4H, m), 5.99 (2H, s), 6.69 (1H, d, J=0.9 Hz), 6.84 (1H, d, J=8.1 Hz), 7.26 (1H, dd J=8.1, 1.7 Hz), 7.38 (1H, d, J=1.7 Hz)

Example 11

Synthesis of Compound 30

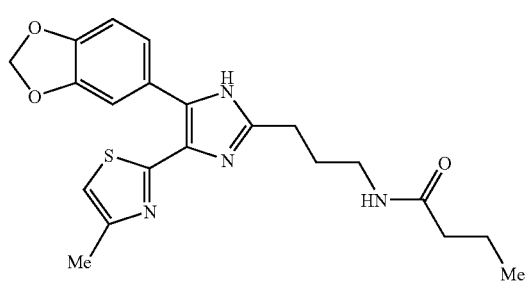

1-ethyl-3-(3-dimethylaminopropyl)-carbodiimide hydrochloride (54 mg) was added to a solution of Compound 29 (80 mg) and butyric acid (25 mg) and 1-hydroxybenzotriazole monohydrate (38 mg) in dimethylformamide (0.8 ml), and the mixture was stirred overnight at room temperature. The reaction mixture was diluted with ethyl acetate, and then washed with a saturated aqueous solution of sodium hydrogen carbonate and a brine successively. After the organic layer was dried over anhydrous magnesium sulfate, the solvent was evaporated. The resultant residue was eluted with a mixed solvent of methanol and chloroform through the NH silica gel column chromatography. The residue from the eluate was recrystallized from a mixed solvent of ethyl acetate and hexane to yield the title compound (18 mg).

¹H NMR (300 MHz, CDCl₃) δ ppm:
0.96 (3H, t, J=7.4 Hz), 1.69 (2H, qt, J=7.4, 7.4 Hz), 1.80-1.94 (2H, m), 2.22 (2H, t, J=7.4 Hz), 2.45 (3H, d, J=0.9 Hz), 2.79 (t, J=6.2 Hz), 3.40 (2H, td, J=6.2, 5.9 Hz), 5.99 (2H, s), 6.03 (1H, brs), 6.72 (1H, s), 6.87 (1H, d, J=8.1 Hz), 7.39 (1H, brd, J=8.1 Hz), 7.55 (1H, brs) mp: 134.0-139.0° C.

Example 12

Synthesis of Compound 31

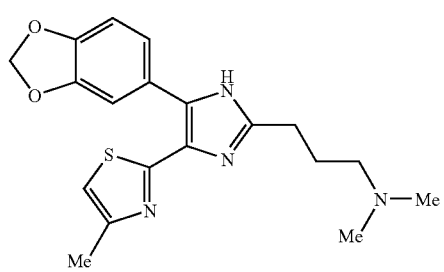

Compound 29 (100 mg) and acetic acid (51 μl) were added to a solution of formaldehyde (73 mg) in tetrahydrofuran (2 ml), and the mixture was stirred for 30 minutes at room temperature. This reaction mixture, to which sodium triacetoxyborohydride (248 mg) was added, was stirred for 16 hours. An aqueous solution of sodium hydrogen carbonate was added to the reaction mixture, and this mixture was extracted twice with ethyl acetate. After the combined organic layer was dried over anhydrous magnesium sulfate, the solvent was evaporated. The resultant residue was purified by NH silica gel column chromatography using a mixed solvent of methanol and chloroform to yield the title compound (74 mg).

$^1$H NMR (200 MHz, DMSO-d6) δ ppm:

1.82 (2H, tt, J=7.7, 6.9 Hz), 2.15 (6H, s), 2.28 (2H, t, J=6.9 Hz), 2.35 (3H, d, J=0.9 Hz), 2.66 (2H, t, J=7.7 Hz), 6.07 (2H, s), 6.99 (1H, d, J=8.1 Hz), 7.09 (1H, d, J=0.9 Hz), 7.46 (1H, brd, J=8.1 Hz), 7.75 (1H, brs), 12.33 (1H, brs)

Example 13

Synthesis of Compound 167

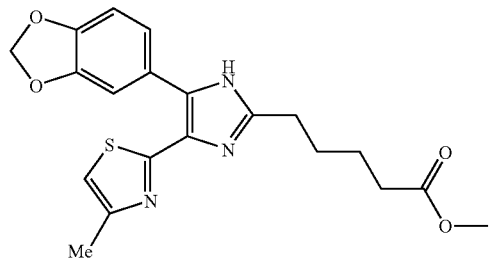

Ammonium acetate (4.20 g) was added to a mixed solution of Compound 203 (1.50 g) and methyl 6-oxohexanoate (1.38 g) with tetrahydrofuran (20 ml) and methanol (10 ml), and the mixture was stirred for 4 hours under reflux condition. After the solvent was evaporated, the solution was diluted with chloroform and washed with a saturated aqueous solution of sodium carbonate. After the organic layer was dried over anhydrous magnesium sulfate, the solvent was evaporated. The resultant residue was purified by silica gel flash column chromatography using a mixed solvent of methanol and chloroform to yield the title compound (797 mg).

$^1$H NMR (300 MHz, CDCl$_3$) δ ppm:

1.67-1.90 (4H, m), 2.39 (2H, t, J=6.9 Hz), 2.43 (3H, d, J=1.1 Hz), 2.81 (2H, t, J=7.2 Hz), 3.69 (3H, s), 6.00 (2H, s), 6.69 (1H, bs), 6.86 (1H, d, J=8.1 Hz), 7.17-7.37 (2H, m) mp: 158.0-159.0° C.

Example 14

Synthesis of Compound 41

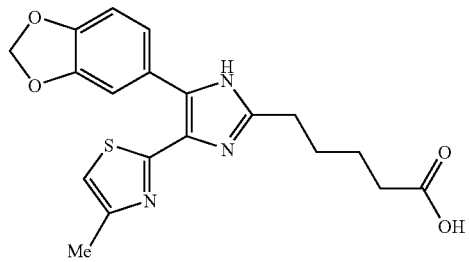

An aqueous solution (10 ml) of sodium hydroxide (227 mg) was added to a solution of Compound 167 (767 mg) in methanol (25 ml), and the mixture was stirred for 1 hour under reflux condition. This solution was neutralized with a 2N aqueous hydrochloric acid solution, and then extracted twice with chloroform. After the organic layer was dried over anhydrous magnesium sulfate, the solvent was evaporated to yield the title compound (790 mg).

$^1$H NMR (300 MHz, CDCl$_3$) δ ppm:

1.82 (2H, m), 2.05 (2H, m), 2.42 (3H, s), 2.53 (2H, t, J=6.8 Hz), 3.28 (2H, t, J=7.8 Hz), 6.03 (2H, s), 6.89 (1H, d, J=0.9 Hz), 6.89 (1H, d, J=8.1 Hz), 7.14 (1H, d, J=1.7 Hz), 7.20 (1H, dd, J=8.1, 1.7 Hz)

Example 15

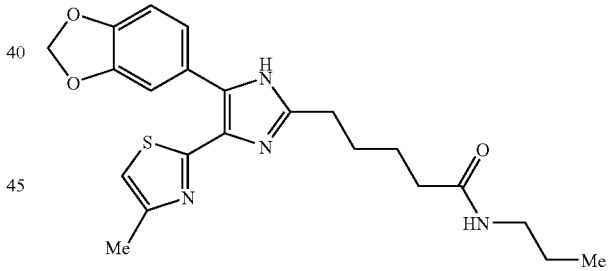

Synthesis of Compound 42

1-ethyl-3-(3-dimethylaminopropyl)-carbodiimide hydrochloride (69 mg) was added to a solution of Compound 41 (120 mg), n-propylamine (21 mg), and 1-hydroxybenzotriazole monohydrate (49 mg) in N,N-dimethylformamide (1.2 ml), and the mixture was stirred overnight at room temperature. The reaction mixture was diluted with ethyl acetate, and then washed with a saturated aqueous solution of sodium hydrogen carbonate and a brine successively. After the organic layer was dried over anhydrous magnesium sulfate, the solvent was evaporated. The resultant residue was purified by silica gel flash column chromatography using a mixed solvent of methanol and chloroform to yield the title compound (51 mg).

¹H NMR (300 MHz, CDCl₃) δ ppm:

0.91 (3H, t, J=7.3 Hz), 1.51 (2H, qt, J=7.3, 7.3 Hz), 1.69-1.91 (4H, m), 2.27 (2H, t, J=6.4 Hz), 2.44 (3H, d, J=0.9 Hz), 2.84 (2H, t, J=6.7 Hz), 3.21 (2H, td, J=7.3, 6.1 Hz), 5.76 (1H, brs), 6.00 (2H, s), 6.71 (1H, d, J=0.9 Hz), 6.86 (1H, d, J=8.1 Hz), 7.33 (1H, brd, J=8.1 Hz), 7.43 (1H, brs)

Example 16

Synthesis of Compound 45

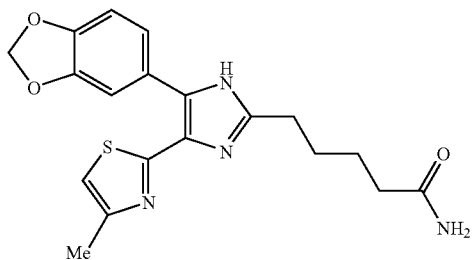

Thionyl chloride (0.3 ml) was added to a solution of Compound 41 (131 mg) in chloroform (1 ml), and the mixture was stirred for 2.5 hours under reflux condition. After the solvent was evaporated off the reaction mixture, a 28% aqueous ammonia was added thereto, and this mixture was extracted twice with chloroform. After the organic layer was dried over anhydrous magnesium sulfate, the solvent was evaporated. The resultant residue was purified by silica gel flash column chromatography using a mixed solvent of methanol and chloroform to yield the title compound (42 mg).

¹H NMR (300 MHz, DMSO-d6) δ ppm:

1.48-1.75 (4H, m), 2.09 (2H, t, J=7.2 Hz), 2.34 (3H, d, J=1.0 Hz), 2.64 (2H, t, J=7.5 Hz), 6.07 (2H, s), 6.72 (1H, bs), 6.99 (1H, d, J=8.2 Hz), 7.09 (1H, d, J=1.0 Hz), 7.26 (1H, bs), 7.50 (1H, dd, J=8.2, 1.7 Hz), 7.82 (1H, d, J=1.7 Hz), 12.21 (1H, brs)

Example 17

Synthesis of Compound 216

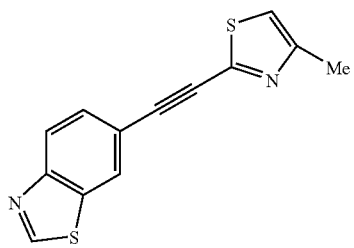

(1) Trimethylsilylacetylene (106 ml), copper (I) iodide (0.948 g), and bis(triphenylphosphine) palladium(II) dichloride (1.75 g) were added to 6-bromobenzothiazole (53.3 g) in triethylamine (260 ml), and the mixture was stirred for 2.5 hours at 80° C. After the solvent was evaporated, the resultant residue was loaded on a short column (silica gel; hexane:ethyl acetate=2:1) for elution. The residue from the eluate was recrystallized from a mixed solvent of hexane-ethyl acetate, and consequently, 6-trimethylsilanylethynylbenzothiazole (20.0 g) was obtained as a colorless powder (mp: 104.5-105.0° C.). By repeated subjecting the filtrate to recrystallization repeated (n-hexhane-ethyl acetate), secondary crystals (12.1 g), tertiary crystals (9.68 g), and quaternary crystals (4.61 g) were obtained as a colorless powder.

¹H NMR (300 MHz, CDCl₃) δ ppm:

0.27 (9H, s), 7.60 (1H, dd, J=8.5, 1.6 Hz), 8.05 (1H, dd, J=8.5, 0.6 Hz), 8.09 (1H, dd, J=1.6, 0.6 Hz), 9.03 (1H, s)

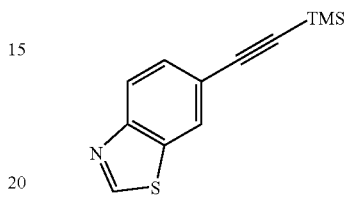

(2) Potassium carbonate (29.7 g) was added to a solution of 6-trimethylsilanylethynylbenzothiazol (45.1 g) in methanol (600 ml), and the mixture was stirred for 1.5 hours at room temperature. The reaction solution was filtered, and then the resultant was washed with methanol and ethyl acetate successively. The filtrate was concentrated, to which water was added, and then extracted with ethyl acetate. The organic layer, which was washed with a brine, was dried over anhydrous magnesium sulfate. After the solvent was evaporated, the residue was purified by silica gel column chromatography (hexane:ethyl acetate=4:1→1:1) to yield 6-ethynylbenzothiazole (30.0 g) as a light yellow solid (mp: 47.5-49.0° C.).

¹H NMR (300 MHz, CDCl₃) δ ppm:

3.16 (1H, s), 7.63 (1H, dd, J=8.4, 1.6 Hz), 8.08 (1H, dd, J=8.5, 0.6 Hz), 8.11 (1H, d, J=1.4 Hz), 9.04 (1H, s)

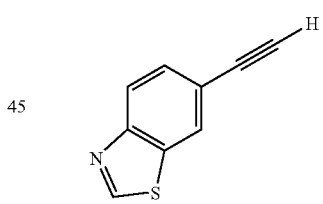

(3) Triethylamine (280 ml) and tetrakis(triphenylphosphine)palladium (6.8 g) were added to a solution of 6-ethynylbenzothiazole (29.5 g) and 2-iodo-4-methylthiazole (45.9 g) in acetonitrile (600 ml) under nitrogen atmosphere. This solution was heated under reflux for 5 hours under nitrogen atmosphere. After the solvent was evaporated, the residue was purified by silica gel column chromatography (hexane:ethyl acetate=2:1→1:1) to yield the title compound (41.2 g) as a light yellow powder (mp: 116.0-117.0° C.).

¹H NMR (200 MHz, CDCl₃) δ ppm:

2.51 (3H, d, J=0.9 Hz), 6.96 (1H, d, J=0.9 Hz), 7.71 (1H, dd, J=8.4, 1.8 Hz), 8.12 (1H, d, J=7.9 Hz), 8.20 (1H, d, J=1.8 Hz), 9.07 (1H, s)

Example 18

Synthesis of Compound 204

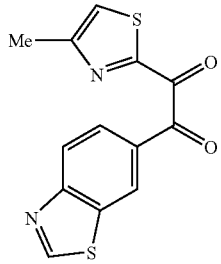

Potassium permanganate (49.3 g) was added to a mixed solution of Compound 216 (40.0 g) acetone (3.0 l)-buffer* (1.8 l), and the mixture was stirred for 30 minutes at room temperature. The reaction solution was cooled on ice, and after sodium nitrite (20.7 g) was added thereto slowly, 10% sulfuric acid (210 ml) was dropped therein. After this solution was stirred for 30 minutes while cooling in ice, the supernatant was extracted with chloroform and the aqueous layer was further extracted with chloroform. The combined organic layer was washed with a saturated aqueous solution of sodium hydrogen carbonate, and then dried over anhydrous magnesium sulfate. After the solvent was evaporated, the residue was purified by silica gel column chromatography (hexane:ethyl acetate=2:1→1:1) to yield the title compound (30.1 g) as a light yellow powder (mp: 134.5-135.5° C.).

buffer*: Sodium hydrogen carbonate (6.8 g) and anhydrous magnesium sulfate (68.0 g) were dissolved in water (3.0 l).

$^1$H NMR (300 MHz, CDCl$_3$) δ ppm:

2.51 (3H, d, J=0.8 Hz), 7.45 (1H, d, J=0.8 Hz), 8.16 (1H, dd, J=8.5, 1.7 Hz), 8.26 (1H, dd, J=8.5, 0.6 Hz), 8.64 (1H, dd, J=1.7, 0.6 Hz), 9.23 (1H, s)

Example 19

Synthesis of Compound 16

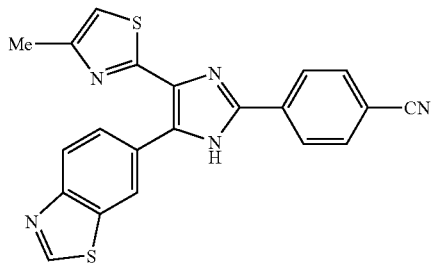

Ammonium acetate (321 mg) was added to a solution of Compound 204 (200 mg) and 4-cyanobenzaldehyde (109 mg) in acetic acid (8.0 ml), and the mixture was stirred for 2 hours under reflux condition and for 14 hours at room temperature. The reaction solution was charged with water and neutralized with 28% aqueous ammonia. This solution was extracted twice with chloroform, and after the organic layer was dried over anhydrous magnesium sulfate, the solvent was evaporated. The resultant residue was washed with chloroform, and crystals were filtered out to yield the title compound (138 mg) as a colorless powder (mp: 295.0-295.5° C.)

$^1$H NMR (300 MHz, DMSO-d6) δ ppm:

2.34 (3H, s), 7.24 (1H, s), 8.00 (2H, d, J=8.5 Hz), 8.10-8.37 (4H, m), 8.86 (1H, brs), 9.48 (1H, s), 13.33 (1H, brs)

Example 20

Synthesis of Compound 50

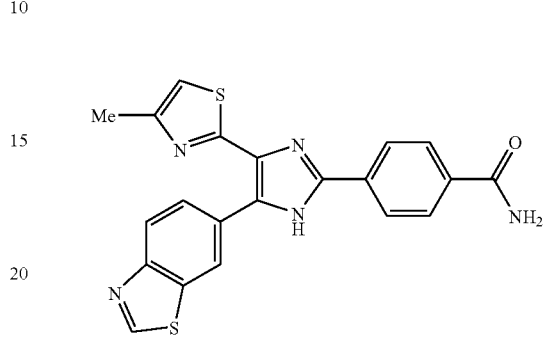

A hydrogen peroxide solution (1.56 ml) was added to a suspension of Compound 16 (130 mg) and potassium carbonate (148 mg) in dimethyl sulfoxide (5.2 ml), and the mixture was stirred for 1 hour at 100° C. This suspension was allowed to be cooled to room temperature, to which water was added, and then the precipitated crystals were filtered out. The crystals were purified by silica gel column chromatography (chloroform:methanol=100:0→90:10) and then recrystallized (chloroform-methanol-n-hexane) to yield the title compound (75.4 mg) as a light yellow powder (mp: >300° C.)

$^1$H NMR (300 MHz, DMSO-d6) δ ppm:

2.34 (3H, s), 7.22 (1H, s), 7.44 (1H, brs), 8.00-8.20 (7H, m), 8.87 (1H, brs), 9.47 (1H, s), 13.15 (1H, brs)

Example 21

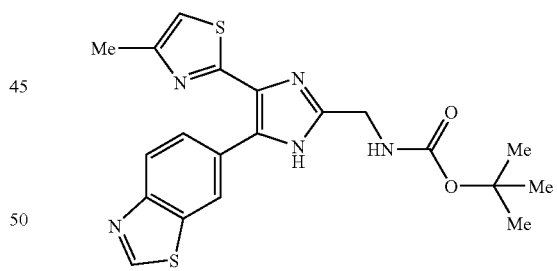

Synthesis of Compound 71

(1) A 1.02M solution of diisobutylalminium hydride in toluene (27 ml) was added dropwise to a solution of methyl tert-butoxycarbonylaminoacetate (2.00 g) in toluene (40 ml) at −70° C., and the mixture was stirred for 1 hour. The reaction solution, to which methanol (10 ml) was added at −70° C., was quenched and then left to room temperature. After the reaction solution was diluted with ethyl acetate, this solution was washed with a 1N aqueous hydrochloric acid solution. The organic layer was washed with a brine filtered through celite, dried over anhydrous magnesium sulfate, and then the solvent was evaporated. The residue was purified by silica gel column chromatography (hexane:ethyl acetate=60:40→30:70) to yield tert-butyl(2-oxoethyl)carbamate (895 mg) as a colorless oil.

¹H NMR (300 MHz, CDCl₃) δ ppm:

1.46 (9H, s), 4.05-4.11 (2H, m), 5.18 (1H, s), 9.66 (1H, s)

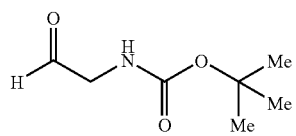

(2) A solution of ammonium acetate (811 mg) in methanol (5.0 ml) was added to a solution of Compound 204 (300 mg) and tert-butyl(2-oxoethyl)carbamate (294 mg) in tetrahydrofuran (10 ml), and the mixture was stirred for 2 hours at room temperature. The reaction solution to which a saturated aqueous solution of sodium hydrogen carbonate was added was neutralized, and then extracted twice with ethyl acetate. After the organic layer was dried over anhydrous magnesium sulfate, the solvent was evaporated. The residue was purified by silica gel column chromatography (hexane:ethyl acetate=40:60→20:80) to yield the title compound (291 mg) as a light yellow amorphous.

¹H NMR (300 MHz, CDCl₃) δ ppm:

1.49 (9H, s), 2.44 (3H, d, J=0.9 Hz), 4.43 (2H, d, J=6.1 Hz), 5.29 (1H, brs), 6.76 (1H, s), 7.86 (1H, dd, J=8.5, 1.8 Hz), 8.18 (1H, d, J=8.4 Hz), 8.55 (1H, brs), 9.04 (1H, s)

Example 22

Synthesis of Compound 70

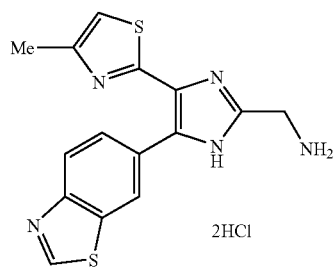

4N hydrochloric acid/dioxane (1.0 ml) was added to a solution of Compound 71 (100 mg) in chloroform (10 ml), and the mixture was stirred for 1.5 hours at room temperature. The solvent was evaporated and then the residue was recrystallized (methanol-diethylether) to yield the title compound (80 mg) as a light brown powder (mp: 229.0-233.0° C.).

¹H NMR (300 MHz, DMSO-d6) δ ppm:

2.37 (3H, d, J=0.9 Hz), 4.16-4.25 (2H, m), 7.22 (1H, d, J=0.9 Hz), 8.08 (1H, dd, J=8.6, 1.8 Hz), 8.18 (1H, d, J=8.5 Hz), 8.60 (3H, br), 8.90 (1H, d, J=0.9 Hz), 9.47 (1H, s)

Example 23

Synthesis of Compound 72

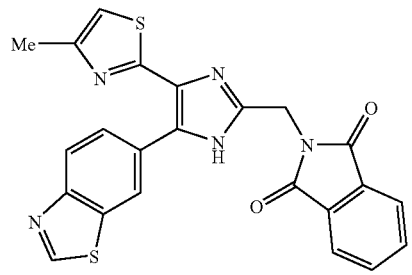

A solution of ammonium acetate (5.40 g) in methanol (50 ml) was added to a solution of Compound 204 (2.00 g) and (1,3-dioxo-1,3-dihydroindol-2-yl) acetaldehyde (2.00 g) in tetrahydrofuran (70 ml), and the mixture was stirred for 3.5 hours at room temperature. The reaction solution to which a saturated aqueous solution of sodium hydrogen carbonate was added was neutralized, and then extracted three times with ethyl acetate. The organic layer was dried over anhydrous magnesium sulfate and the solvent was evaporated off. The residue was purified by silica gel column chromatography three times with (hexane:ethyl acetate=40:60→20:80), (chloroform:methanol=95:5), and (chloroform:ethyl acetate=35:65) to yield the title compound (1.90 g) as a light yellow powder (mp: 250.5-255.0° C.)

¹H NMR (300 MHz, CDCl₃) δ ppm:

2.44 (3H, d, J=0.8 Hz), 5.08 (2H, s), 6.74 (1H, brs), 7.71-7.94 (6H, m), 8.16 (1H, d, J=8.5 Hz), 9.03 (1H, s)

Example 24

Synthesis of Compound 105

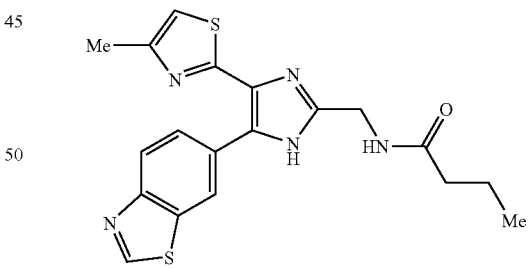

(1) Hydrazine monohydrate (2.12 g) was added to a suspension of Compound 72 (1.88 g) in ethanol (45 ml), and the mixture was stirred for 24 hours at room temperature. Methanol and chloroform were added to this reaction solution so as to completely dissolve the precipitate therein. After adding NH silica gel to this solution, the solvent was evaporated. The residue was purified by NH silica gel column chromatography (chloroform:methanol=95:5) and then by silica gel column chromatography (chloroform:methanol=90:10→chloroform:methanol:ammonia=100:10:1) to yield the free form of Compound 70 (761 mg) as a light yellow amorphous.

¹H NMR (300 MHz, CDCl₃) δ ppm:

2.44 (3H, d, J=1.1 Hz), 4.12 (2H, s), 6.73 (1H, br), 7.87 (1H, dd, J=8.5, 1.7 Hz), 8.17 (1H, dd, J=8.5, 0.5 Hz), 8.47 (1H, br), 9.03 (1H, s)

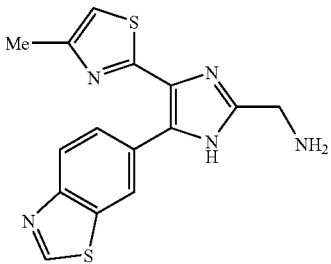

(2) Butyryl chloride (0.21 ml) was dropped in a solution of the free form of Compound 70 (600 mg) and triethylamine (370 mg) in chloroform (15.0 ml) while cooling in ice. After stirring for 30 minute while ice-cooling, this reaction solution was charged with water and extracted twice with chloroform. The organic layer was dried over anhydrous magnesium sulfate and then the solvent was evaporated. After the residue was purified by silica gel column chromatography (ethyl acetate→chloroform:methanol=90:10), the purified material was recrystallized (ethyl acetate-hexane) to yield the title compound (441 mg) as a yellow powder (mp: 190.0-191.0° C.).

¹H NMR (300 MHz, DMSO-d6) δ ppm:

0.89 (3H, t, J=7.4 Hz), 1.47-1.64 (2H, m), 2.14 (2H, t, J=7.5 Hz), 2.34 (3H, s), 4.36 (2H, d, J=5.6 Hz), 7.15 (1H, d, J=0.9 Hz), 8.08 (1H, s), 8.14 (1H, d, J=8.5 Hz), 8.34 (1H, t, J=5.1 Hz), 8.85 (1H, s), 9.43 (1H, s), 12.72 (1H, s)

Example 25

Synthesis of Compound 88

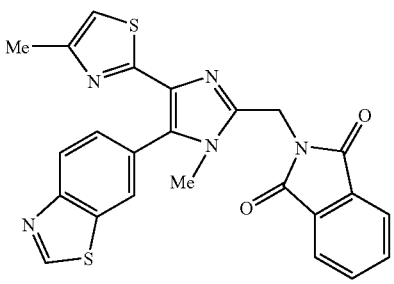

Compound 72 (100 mg) was added to a suspension of sodium hydride (13 mg) in N,N-dimethylformamide (2.0 ml) while ice-cooling, and the mixture was stirred for 10 minutes. This suspension, to which methyl iodide (0.14 ml) was added while ice-cooling, was stirred for 1.5 hours while ice-cooling. The reaction solution to which a brine was added was extracted with chloroform. The organic layer was dried over anhydrous magnesium sulfate and then the solvent was evaporated. After the residue was purified by silica gel column chromatography (ethyl acetate), the purified material was recrystallized (ethyl acetate-hexane) to yield the title compound (35 mg) as a colorless powder (mp: 257.0-259.5° C.)

¹H NMR (300 MHz, CDCl₃) δ ppm:

2.28 (3H, d, J=0.9 Hz), 3.65 (3H, s), 5.06 (2H, s), 6.60 (1H, d, J=0.9 Hz), 7.56 (1H, dd, J=8.4, 1.7 Hz), 7.72-7.93 (4H, m), 8.11 (1H, d, J=1.6 Hz), 8.23 (1H, d, J=8.5 Hz), 9.09 (1H, s)

The filtrate was concentrated to yield 2-(4-benzothiazol-6-yl-1-methyl-5-(4-methylthiazol-2-yl)-1H-imidazol-2-ylmethyl)isoindole-1,3-dione (15 mg) as represented by the following formula as a colorless amorphous.

¹H NMR (300 MHz, CDCl₃) δ ppm:

2.54 (3H, d, J=1.1 Hz), 3.87 (3H, s), 5.05 (2H, s), 6.95 (1H, d, J=0.9 Hz), 7.52 (1H, dd, J=8.5, 1.7 Hz), 7.72-7.93 (4H, m), 7.96 (1H, dd, J=8.5, 0.6 Hz), 8.17 (1H, dd, J=1.7, 0.5 Hz), 8.93 (1H, s)

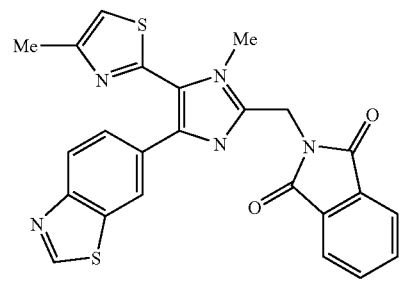

Example 26

Synthesis of Compound 89

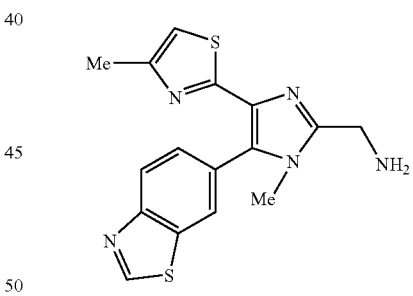

Hydrazine monohydrate (290 mg) was added to a suspension of Compound 88 (328 mg) in methanol (5.0 ml), and the mixture was stirred for 3 hours at room temperature. The reaction solution was diluted with water and extracted twice with chloroform. The organic layer was dried over anhydrous magnesium sulfate and then the solvent was evaporated. The residue was purified by silica gel column chromatography (chloroform:methanol=90:10→chloroform:methanol:ammonia=100:10:1) to yield the title compound (166 mg) as a colorless powder (mp: 183.0-184.5° C.).

¹H NMR (300 MHz, CDCl₃) δ ppm:

2.36 (3H, d, J=0.9 Hz), 3.52 (3H, s), 4.06 (2H, s), 6.61 (1H, d, J=0.9 Hz), 7.56 (1H, dd, J=8.5, 1.6 Hz), 8.10 (1H, dd, J=1.6, 0.5 Hz), 8.26 (1H, dd, J=8.4, 0.5 Hz), 9.10 (1H, s)

Example 27

Synthesis of Compound 90

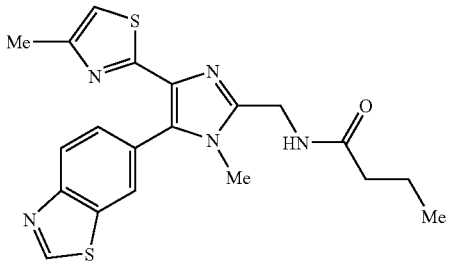

Butyryl chloride (0.06 ml) was dropped in a solution of Compound 89 (159 mg) and triethylamine (101 mg) in chloroform (5.0 ml) while cooling in ice. After stirring for 1 hour while ice-cooling, this reaction solution was charged with water and was extracted twice with chloroform. The organic layer was dried over anhydrous magnesium sulfate and then the solvent was evaporated. After the residue was purified by silica gel column chromatography (chloroform:methanol=9:1) and then by NH silica gel column chromatography (ethyl acetate), the purified material was recrystallized (ethyl acetate-hexane) to yield the title compound (137 mg) as a colorless powder (mp: 212.5-213.5° C.).

$^1$H NMR (300 MHz, DMSO-d6) δ ppm:

0.88 (3H, t, J=7.4 Hz), 1.47-1.63 (2H, m), 2.09-2.18 (5H, m), 3.47 (3H, s), 4.46 (2H, d, J=5.8 Hz), 7.04 (1H, d, J=0.9 Hz), 7.64 (1H, dd, J=8.5, 1.7 Hz), 8.17 (1H, dd, J=8.5, 0.5 Hz), 8.34 (1H, dd, J=1.7, 0.5 Hz), 8.46 (1H, brt, J=5.6 Hz), 9.49 (1H, s)

Example 28

Synthesis of Compound 95

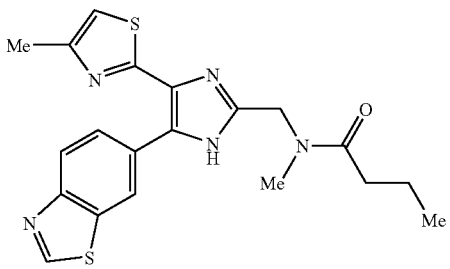

(1) Butyryl chloride (4.6 ml) was dropped into a solution of 2-(methylamino)ethanol (3.0 g) and triethylamine (11.0 ml) in chloroform (30 ml) while ice-cooling. The mixture was stirred for 20 minutes while ice-cooling, and water was then added thereto. The mixture was extracted twice with chloroform. After the organic layer was dried over anhydrous magnesium sulfate, the solvent was evaporated. The residue was purified by silica gel column chromatography (hexane:ethyl acetate=2:3→1:4, and then chloroform:methanol=9:1) to yield N-(hydroxyethyl)-N-methylbutylamide (2.8 g) as a light yellow oil.

$^1$H NMR (300 MHz, CDCl$_3$) δppm:

0.91-1.02 (3H, m), 1.58-1.77 (2H, m), 2.26-2.46 (2H, m), 2.96 and 3.07 (3H, 2s), 3.47 and 3.56 (2H, 2t, J=5.7 Hz), 3.78 (2H, t, J=5.1 Hz)

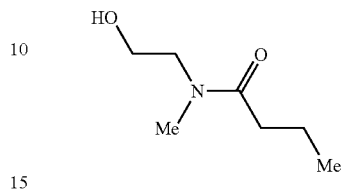

(2) A Dess-Martin reagent (1.9 g) was added to a solution of N-(hydroxyethyl)-N-methyl-butylamide (600 mg) in dichloromethane (6.0 ml), and the mixture was stirred for 1.5 hours at room temperature. The solvent was evaporated off to obtain crude crystals, N-methyl-N-(2-oxoethyl)butylamide without purification. A solution of ammonium acetate (820 mg) in methanol (5.0 ml) was added to a solution of N-methyl-N-(2-oxoethyl)butylamide and Compound 204 (301 mg) in tetrahydrofuran (15 ml), and the mixture was stirred for 14 hours at room temperature. The reaction solution was neutralized with a saturated aqueous solution of sodium hydrogen carbonate and then extracted twice with ethyl acetate. After the organic layer was dried over anhydrous magnesium sulfate, the solvent was evaporated. The residue was purified by NH silica gel column chromatography (hexane:ethyl acetate=35:65→chloroform:methanol=95:5) and then recrystallized (ethyl acetate-hexane) to yield the title compound (233 mg) as a light yellow powder (mp: 175.0-175.5° C.)

$^1$H NMR (300 MHz, DMSO-d6) δ ppm:

0.87-0.98 (3H, m), 1.48-1.67 (2H, m), 2.26-2.44 (5H, m), 2.90 and 3.07 (3H, 2s), 4.63 (2H, s), 7.15 (1H, m), 8.03-8.19 (2H, m), 8.84 (1H, m), 9.44 (1H, d, J=1.2 Hz), 12.67 and 12.84 (1H, 2br)

Example 29

Synthesis of Compound 96

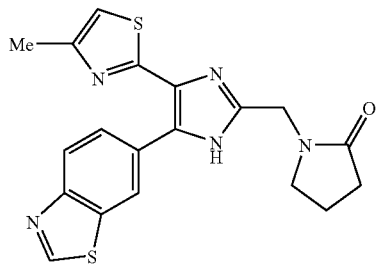

(1) A 1.02M solution of diisobutylalminium hydride in toluene (16 ml) was added dropwise to a solution of methyl (2-oxopyrrolidin-1-yl)acetate (1.01 g) in toluene (10 ml) at −78° C., and the mixture was stirred for 1 hour. The reaction solution was quenched with methanol at −78° C., then diluted with a 1N aqueous solution of hydrochloric acid, and allowed to warm to room temperature with stirring. The reaction solution was filtered through celite and then the filtrate was dried up. The residue was purified by silica gel column chromatography (chloroform:methanol=95:5→90:10) to yield 2-oxopyrrolidin-1-yl-acetaldehyde (120 mg) as a colorless oil.

¹H NMR (300 MHz, CDCl₃) δ ppm:

2.04-2.20 (2H, m), 2.46 (2H, t, J=8.2 Hz), 3.47 (2H, t, J=8.2 Hz), 4.17 (2H, s), 9.61 (1H, s)

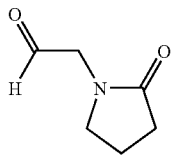

(2) A solution of ammonium acetate (640 ml) in methanol (5.0 ml) was added to a solution of 2-oxopyrrolidin-1-yl-acetaldehyde (120 mg) and Compound 204 (230 mg) in tetrahydrofuran (10 ml), and the mixture was stirred for 1.5 hours at room temperature. The reaction solution was neutralized with a saturated aqueous solution of sodium hydrogen carbonate and then extracted twice with chloroform. After the organic layer was dried over anhydrous magnesium sulfate, the solvent was evaporated. The residue was purified by NH silica gel column chromatography (ethyl acetate→chloroform:methanol=90:10) and then recrystallized (chloroform-ethyl acetate-hexane) to yield the title compound (161 mg) as a colorless powder (mp: 209.5-210.5° C.).

¹H NMR (300 MHz, DMSO-d6) δ ppm:

1.90-2.05 (2H, m), 2.25-2.33 (2H, m), 2.33 (3H, s), 3.43 (2H, t, J=7.2 Hz), 4.50 (2H, s), 7.15 (1H, d, J=1.1 Hz), 8.08 (1H, brs), 8.13 (1H, d, J=8.4 Hz), 8.81 (1H, brs), 9.43 (1H, s), 12.82 (1H, br)

Example 30

Synthesis of Compound 197

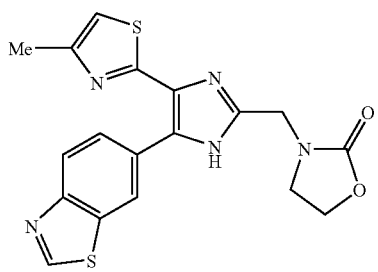

(1) Oxazolidin-2-one (331 mg) was added to a suspension of sodium hydride (181 mg) in N,N-dimethylformamide (5.0 ml) while ice-cooling, and the mixture was stirred for 20 minutes. To this suspension, a solution of 2-bromoethoxymethylbenzene (1.11 g) in N,N-dimethylformamide (3.0 ml) was added dropwise dropped while ice-cooling, and then the mixture was stirred for 1 hour at room temperature. The reaction solution was diluted with ethyl acetate and washed twice with a brine. After the organic layer was dried over anhydrous magnesium sulfate, the solvent was evaporated. The residue was purified by silica gel column chromatogra phy (hexane:ethyl acetate=2:3) to yield 3-(2-benzyloxyethyl) oxazolidin-2-one (281 mg) as a colorless oil.

¹H NMR (300 MHz, CDCl₃) δ ppm:

3.46-3.52 (2H, m), 3.63-3.72 (4H, m), 4.25-4.34 (2H, m), 4.53 (2H, s), 7.27-7.40 (5H, m)

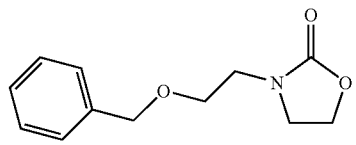

(2) 20% palladium hydroxide (138 mg) was added to a solution of 3-(2-benzyloxyethyl)oxazolidin-2-one (278 mg) in methanol (10 ml), and the mixture was stirred for 2 hours at room temperature under hydrogen atmosphere. The reaction solution was filtered through celite and then the solvent was evaporated. The residue was purified by silica gel column chromatography (chloroform:methanol=90:10) to yield 3-(2-hydroxyethyl)oxazolidin-2-one (144 mg) as a colorless oil.

¹H NMR (200 MHz, CDCl₃) δ ppm:

2.29 (1H, br), 3.39-3.47 (2H, m), 3.64-3.77 (2H, m), 3.78-3.89 (2H, m), 4.30-4.43 (2H, m)

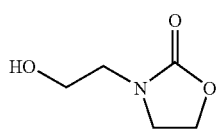

(3) A Dess-Martin reagent (516 mg) was added to a solution of 3-(2-hydroxyethyl)oxazolidin-2-one (144 mg) in dichloromethane (5.0 ml), and the mixture was stirred for 1 hour at room temperature. The solvent was evaporated off to obtain crude crystals, (2-oxooxazolidin-3-yl)acetaldehyde without purification. A solution of ammonium acetate (771 mg) in methanol (5.0 ml) was added to a suspension of (2-oxooxazolidin-3-yl)acetaldehyde and Compound 204 (286 mg) in tetrahydrofuran (10 ml), and the mixture was stirred for 2 weeks at room temperature. The reaction solution was neutralized with a saturated aqueous solution of sodium hydrogen carbonate and then extracted twice with ethyl acetate. After the organic layer was dried over anhydrous magnesium sulfate, the solvent was evaporated. The residue was purified by NH silica gel column chromatography (chloroform→chloroform:methanol=95:5) and then recrystallized (methanol-ethyl acetate-hexane) to yield the title compound (149 mg) as a colorless powder (mp: 232.0-233.0° C.)

¹H NMR (300 MHz, DMSO-d6) δ ppm:

2.34 (3H, s), 3.60-3.68 (2H, m), 4.28-4.36 (2H, m), 4.49 (2H, s), 7.16 (1H, d, J=0.9 Hz), 8.08 (1H, br), 8.14 (1H, d, J=8.4 Hz), 8.83 (1H, br), 9.44 (1H, s), 12.93 (1H, br)

Example 31

Synthesis of Compound 138

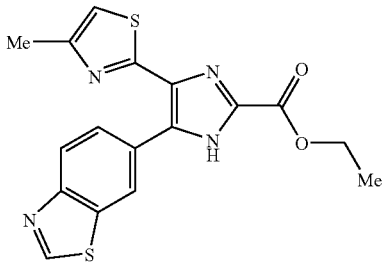

A solution of ammonium acetate (5.35 g) in methanol (40 ml) was added to a solution of ethyl glyoxylate (45% aqueous solution, 2.36 g) and Compound 204 (2.0 g) in tetrahydrofuran (60 ml), and then the mixture was stirred for 12 hours at room temperature. This solution was diluted with ethyl acetate and then washed with a saturated aqueous solution of sodium hydrogen carbonate and a brine successively. The organic layer was dried over anhydrous magnesium sulfate and then the solvent was evaporated. The residue was purified by silica gel column chromatography (hexane:ethyl acetate=5:5→3:7→1:9) and then by NH silica gel column chromatography (chloroform:methanol=50:1), before recrystallization (ethyl acetate-hexane) to yield the title compound (1.01 g) as a colorless powder (mp: 238.5-239.0° C.).

$^1$H NMR (300 MHz, DMSO-d6) δ ppm:
1.37 (3H, t, J=7.1 Hz), 2.31 (3H, s), 4.40 (2H, q, J=6.8 Hz), 7.24 (1H, s), 8.03 (1H, d, J=8.7 Hz), 8.14 (1H, d, J=8.5 Hz), 8.74 (1H, s), 9.48 (1H, s), 14.02 (1H, s)

Example 32

Synthesis of Compound 82

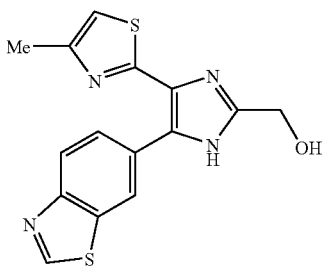

Compound 138 (700 mg) was added to a suspension of lithium aluminum hydride (134 mg) in tetrahydrofuran (30 ml) at −40° C. and the mixture was stirred until the temperature reached 0° C., and further stirred for 30 minutes at 0° C. This solution was charged with a 2N aqueous solution of hydrochloric acid and stirred for 5 minutes. The solution was diluted with ethyl acetate, and washed with a saturated aqueous solution of sodium hydrogen carbonate and a brine successively. The organic layer was dried over anhydrous magnesium sulfate and then the solvent was evaporated. The residue was purified by silica gel column chromatography (chloroform:methanol=20:1→10:1) and recrystalized (chloroform-methanol-hexane) to yield the title compound (309 mg) as a light orange powder (mp: 222.0-223.0° C.).

$^1$H NMR (300 MHz, DMSO-d6) δ ppm:
2.34 (3H, d, J=0.8 Hz), 4.53 (2H, s), 5.50 (1H, brs), 7.15 (1H, d, J=0.9 Hz), 8.05-8.18 (2H, m), 8.87 (1H, brs), 9.43 (1H, s), 12.80 (1H, br)

Example 33

Synthesis of Compound 198

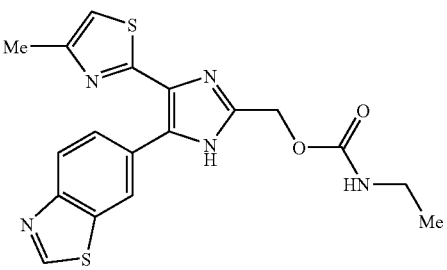

Ethyl isocyanate (57 mg) was added to a suspension of Compound 82 (239 mg), copper (I) chloride (7 mg), and pyridine (1.0 ml) in toluene (2.0 ml), and the mixture was stirred for 2 hours at 50° C. This solution was charged with water and extracted with chloroform. The organic layer was washed with a brine and dried over anhydrous magnesium sulfate, and then the solvent was evaporated. The residue was purified by silica gel column chromatography (chloroform:methanol=30:1) and then recrystallized (ethyl acetate-hexane) to yield the title compound (151 mg) as a colorless powder (mp: 144.0-145.0° C.).

$^1$H NMR (300 MHz, DMSO-d6) δ ppm:
1.04 (3H, t, J=7.2 Hz), 2.34 (3H, s), 2.99-3.12 (2H, m), 5.04 (2H, s), 7.18 (1H, d, J=0.8 Hz), 7.34 (1H, brt, J=5.7 Hz), 8.03-8.20 (2H, m), 8.90 (1H, brs), 9.45 (1H, s), 13.06 (1H, brs)

Example 34

Synthesis of Compound 81

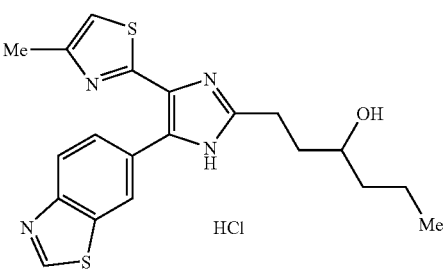

(1) A 1.02M solution of diisobutylalminium hydride in toluene (23.4 ml) was added dropwise to a solution of 5-propyldihydrofuran-2-one (1.50 g) in toluene (30 ml) over 50 minutes at −70° C. under nitrogen atmosphere, and the mixture was stirred for 1 hour at −70° C. The reaction solution was quenched with methanol (3.0 ml) at −70° C., and then left to room temperature. After adding a 10% aqueous solution of citric acid, this reaction solution was stirred for 5 minutes.

Then this solution was extracted with ethyl acetate, and the organic layer was washed with a brine. After the organic layer was dried over anhydrous magnesium sulfate, the solvent was evaporated, and then the residue was purified by silica gel column chromatography (hexane:ethyl acetate=90:10→80:20) to yield 5-propyltetrahydrofuran-2-ol (440 mg) as a colorless oil.

¹H NMR (300 MHz, CDCl₃) δ ppm:

0.9-0.98 (3H, m), 1.29-2.21 (7H, m), 2.45-2.56 (1H, m), 3.94-4.26 (1H, m), 5.41-5.60 (1H, m)

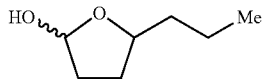

(2) A solution of ammonium acetate (1.98 g) in methanol (18 ml) was added to a solution of Compound 204 (741 mg) and 5-propyltetrahydrofuran-2-ol (435 mg) in tetrahydrofuran (25 ml) and the mixture was stirred for 13 hours at room temperature. After diluting with ethyl acetate, this reaction solution was washed with water and a brine successively. The organic layer was dried over anhydrous sodium sulfate and then the solvent was evaporated. The residue was purified by silica gel column chromatography (ethyl acetate→chloroform:methanol=40:1). The purified material was dissolved in methanol, to which a 4N hydrochloric acid/ethyl acetate solution was added. After the solvent was evaporated, this material was recrystallized (methanol-ethyl acetate) to yield the title compound (165 mg) as a colorless powder.

¹H NMR (300 MHz, DMSO-d6) δ ppm:

0.82-0.96 (3H, m), 1.25-1.49 (4H, m), 1.70-2.09 (2H, m), 2.33-2.48 (3H, m), 2.90-3.29 (2H, m), 3.51 (1H, m), 7.37 (1H, s), 7.84 (1H, dd, J=8.5, 1.8 Hz), 8.29 (1H, d, J=8.5 Hz), 8.61 (1H, d, J=1.7 Hz), 9.58 (1H, s)

Example 35

Synthesis of Compound 201

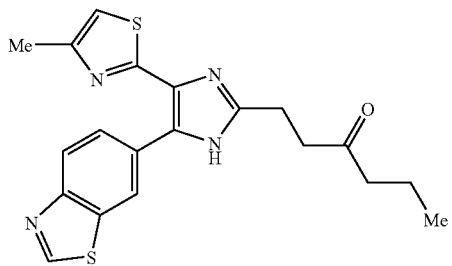

A Dess-Martin reagent (400 mg) was added to a solution of the free form of Compound 81 (342 mg) in dichloromethane (7.0 ml), and the mixture was stirred for 2 hours at room temperature. The reaction solution was charged with water and extracted with chloroform. After the organic layer was washed with a brine this material was dried over anhydrous magnesium sulfate, and then the solvent was evaporated. The residue was purified by silica gel column chromatography (hexane:ethyl acetate=1:1→3:7→1:9) and then recrystal lized (ethyl acetate-hexane) to yield the title compound (225 mg) as a colorless powder (mp: 145.0-146.0° C.)

¹H NMR (300 MHz, CDCl₃) δ ppm:

0.93 (3H, t, J=7.4 Hz), 1.58-1.71 (2H, m), 2.44 (3H, d, J=0.9 Hz), 2.44-2.50 (2H, m), 2.95-3.11 (4H, m), 6.72 (1H, d, J=0.9 Hz), 7.86 (1H, dd, J=8.5, 1.8 Hz), 8.16 (1H, dd, J=8.5, 0.6 Hz), 8.48 (1H, br), 9.03 (1H, s)

Example 36

Synthesis of Compound 73

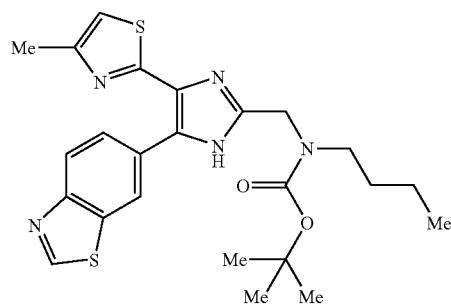

(1) Di-tert-butyl dicarbonate (5.87 g) was added dropwise to a solution of 2-butylaminoethanol (3.00 g) in chloroform (30 ml), and the mixture was stirred for 15 minutes at room temperature. The solvent was evaporated off to yield tert-butyl butyl-(2-hydroxyethyl)carbamate (6.10 g) as a colorless oil.

¹H NMR (300 MHz, CDCl₃) δ ppm:

0.93 (3H, t, J=7.3 Hz), 1.22-1.56 (13H, m), 3.22 (2H, t, J=7.3 Hz), 3.38 (2H, t, J=5.1 Hz), 3.69-3.80 (2H, m)

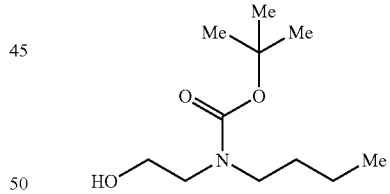

(2) A Dess-Martin reagent (2.15 g) was added to a solution of tert-butyl butyl-(2-hydroxyethyl) carbamate (1.00 g) in dichloromethane (20 ml) at room temperature, and the mixture was stirred for 15 minutes at room temperature. After the solvent was evaporated, the residue was purified by silica gel column chromatography (hexane:ethyl acetate-80:20→75:25) to yield tert-butyl butyl-(2-oxoethyl)carbamate (755 mg) as a colorless oil.

¹H NMR (300 MHz, CDCl₃) δ ppm:

0.93 (3H, t, J=7.2 Hz), 1.20-1.55 (13H, m), 3.19-3.36 (2H, m), 3.82 (1H, s), 3.92 (1H, s), 9.58 (1H, s)

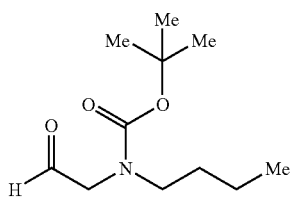

(3) A solution of ammonium acetate (2.00 g) in methanol (20 ml) was added to a solution of Compound 204 (750 mg) and tert-butyl butyl-(2-oxoethyl)carbamate (728 mg) in tetrahydrofuran (30 ml), and the mixture was stirred for 1 hour at room temperature. The reaction solution was diluted with ethyl acetate, and then washed with water and a brine successively. After the organic layer was dried over anhydrous sodium sulfate, the solvent was evaporated. The residue was purified by silica gel column chromatography (hexane:ethyl acetate=80:20→50:50) to yield the title compound (862 mg) as a colorless amorphous.

$^1$H NMR (300 MHz, DMSO-d6) δ ppm:

0.88 (3H, t, J=7.2 Hz), 1.20-1.59 (13H, m), 2.34 (3H, s), 3.29 (2H, brs), 4.46 (2H, brs), 7.14 (1H, s), 8.02-8.18 (2H, m), 8.86 (1H, brs), 9.43 (1H, s), 12.73 (1H, brs)

Example 37

Synthesis of Compound 74

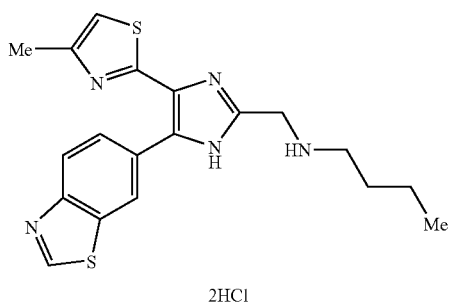

A 10% hydrochloric acid/methanol (10 ml) solution of Compound 73 (875 mg) was stirred for 4 hours at room temperature. The reaction solution was stirred for 30 minutes at room temperature after addition of a 4N hydrochloric acid/dioxane (1.0 ml) solution. After the solvent was evaporated, the residue was recrystallized (methanol-diethylether) to yield the title compound (730 mg) as a colorless powder.

$^1$H NMR (300 MHz, DMSO-d6) δ ppm:

0.91 (3H, t, J=7.4 Hz), 1.31-1.45 (2H, m), 1.62-1.75 (2H, m), 2.38 (3H, d, J=1.1 Hz), 3.00-3.15 (2H, m), 4.32-4.41 (2H, m), 7.25 (1H, d, J=0.9 Hz), 8.12 (1H, dd, J=8.7, 1.8 Hz), 8.19 (1H, dd, J=8.7, 0.6 Hz), 8.94 (1H, d, J=1.2 Hz), 9.49 (1H, s), 9.69 (2H, brs)

Example 38

Synthesis of Compound 78

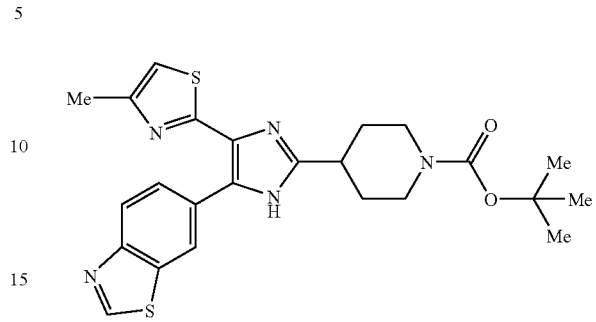

(1) Di-tert-butyldicarbonate (4.17 g) was added to piperidin-4-ylmethanol (2.00 g) in a mixed solvent of ethyl acetate (20 ml) and tetrahydrofuran (10 ml), and the mixture was stirred for 22 hours at room temperature. The solvent was evaporated, and the residue was charged with ethyl acetate and washed with a saturated aqueous solution of ammonium chloride and a brine successively. After the organic layer was dried over anhydrous magnesium sulfate, the solvent was evaporated to yield tert-butyl 4-hydroxymethylpiperidine-1-carboxylate (4.06 g) as a light pink oil.

$^1$H NMR (200 MHz, CDCl$_3$) δ ppm: 1.02-1.82 (5H, m), 1.46 (9H, s), 2.59-2.81 (2H, m), 3.43-3.59 (2H, m), 4.02-4.23 (2H, m)

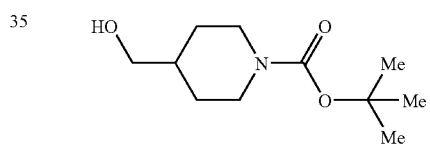

(2) A Dess-Martin reagent (7.89 g) was added to a solution of tert-butyl 4-hydroxymethylpiperidine-1-carboxylate (4.00 g) in dichloromethane (40 ml), and the mixture was stirred for 1.5 hours at room temperature. After diluting with ethyl acetate, the reaction solution was washed with a 1% aqueous solution of sodium hydroxide and a brine successively. The organic layer was dried over anhydrous magnesium sulfate, and then the solvent was evaporated. The residue was purified by silica gel column chromatography (hexane:ethyl acetate=2:1→1:1) to yield tert-butyl 4-formylpiperidine-1-carboxylate (2.43 g) as a colorless oil.

$^1$H NMR (200 MHz, CDCl$_3$) δ ppm:

1.46 (9H, s), 1.38-1.99 (4H, m), 2.41 (1H, m), 2.83-3.03 (2H, m), 3.87-4.08 (2H, m), 9.66 (1H, s)

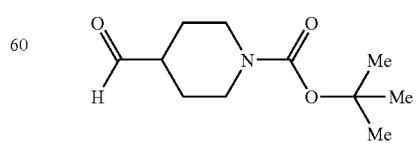

(3) A solution of ammonium acetate (5.35 g) in methanol (35 ml) was added to a solution of Compound 204 (2.00 g)

and tert-butyl 4-formylpiperidine-1-carboxylate (2.22 g) in tetrahydrofuran (70 ml), and the mixture was stirred for 15 hours at room temperature. After diluting with ethyl acetate, the reaction solution was washed with water and a brine successively. The organic layer was dried over anhydrous sodium sulfate, and then the solvent was evaporated. The residue was purified by silica gel column chromatography (chloroform:methanol=50:1→20:1) to yield the title compound (3.27 g) as a light yellow amorphous.

$^1$H NMR (200 MHz, CDCl$_3$) δ ppm:

1.47 (9H, s), 1.67-2.17 (4H, m), 2.43 (3H, d, J=0.9 Hz), 2.76-3.09 (3H, m), 4.13-4.33 (2H, m), 6.68 (1H, s), 7.85 (1H, dd, J=8.6, 1.5 Hz), 8.17 (1H, d, J=8.4 Hz), 8.30 (1H, s), 9.02 (1H, s)

Example 39

Synthesis of Compound 77

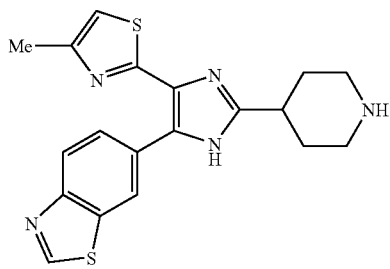

A 4N hydrochloric acid/ethyl acetate solution (10.4 ml) was added to a solution of Compound 78 (2.00 g) in methanol (20 ml), and the mixture was stirred for 1 hour at room temperature and then for 1.5 hours at 50° C. After the reaction solution was diluted with chloroform, the organic layer was washed with a saturated aqueous solution of sodium hydrogen carbonate. The aqueous layer was saturated with sodium chloride, and then extracted with chloroform. The combined organic layer was dried over anhydrous magnesium sulfate, and then the solvent was evaporated. The residue was purified by NH silica gel column chromatography (chloroform:methanol=50:1→20:1) and then recrystallized (ethyl acetate) to yield the title compound (793 mg) as a colorless powder (mp: 199.5-200.5° C.).

$^1$H NMR (300 MHz, CDCl$_3$) δ ppm:

1.76-2.17 (4H, m), 2.45 (3H, d, J=0.9 Hz), 2.72-2.85 (2H, m), 3.02 (1H, m), 3.20-3.32 (2H, m), 6.68 (1H, brs), 7.85 (1H, dd, J=8.5, 1.7 Hz), 8.17 (1H, dd, J=8.5, 0.3 Hz), 8.32 (1H, br), 9.03 (1H, s)

Example 40

Synthesis of Compound 226

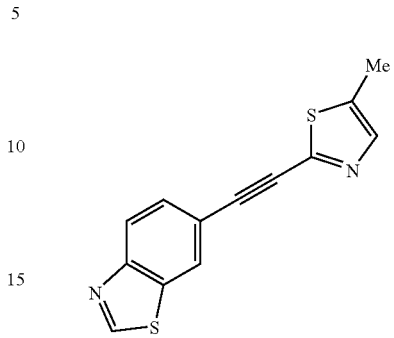

(1) After t-butyl nitrite (1.99 g) was added dropwise to a suspension of 2-amino-5-methyltiazole (2.00 g) in acetonitrile (20 ml) while ice-cooling, copper (II) bromide (4.30 g) was gradually added thereto. This suspension was stirred for 3 hours at 0° C. The reaction solution was charged with 1N hydrochloric acid (100 ml) and then extracted twice with ethyl acetate (200 ml). After the organic layer was dried over anhydrous magnesium sulfate, the solvent was evaporated. The residue was purified by silica gel column chromatography (neutral; hexane:ethyl acetate=80:20) to yield 2-bromo-5-methylthiazole (1.31 g) as a yellow oil.

$^1$H NMR (300 MHz, CDCl$_3$) δ ppm:

2.44 (3H, d, J=1.2 Hz), 7.25 (1H, d, J=1.1 Hz)

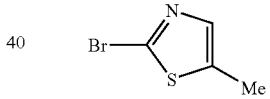

(2) A 2.59M solution of n-butyllithium in hexane (2.40 ml) was added dropwise to a solution of 2-bromo-5-methylthiazole (1.00 g) in tetrahydrofuran (10 ml) at −78° C., and the mixture was stirred for 40 minutes at the same temperature. A solution of iodine (1.55 g) in tetrahydrofuran (5 ml) was added dropwise thereto at −78° C., and the mixture was stirred for 30 minutes at the same temperature. A saturated aqueous solution of ammonium chloride (20 ml) was added to the reaction solution so as to quench the reaction, and this solution was left to room temperature. This solution was charged with water (20 ml) and extracted twice with ethyl acetate (100 ml). The organic layer was washed with a saturated aqueous solution of sodium thiosulfate (50 ml), and then dried over anhydrous magnesium sulfate. After the solvent was evaporated, the residue was purified by silica gel column chromatography (hexane:ethyl acetate=85:15) to yield 2-iodo-5-methylthiazole (764 mg) as a brown oil.

$^1$H NMR (300 MHz, CDCl$_3$) δ ppm:

(300 MHz, CDCl3) 5 ppm: 2.47 (3H, d, J=1.2 Hz), 7.26 (1H, d, J=1.2 Hz)

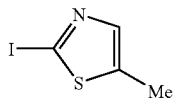

(3) To a solution of 6-ethynylbenzothiazole (483 mg) synthesized in Example 17-(2) and 2-iodo-5-methylthiazole (740 mg) in acetonitrile (10 ml), triethylamine (15 ml) and tetrakis(triphenylphosphine) palladium (179 mg) were added under nitrogen atmosphere. This solution was heated under reflux for 6 hours under nitrogen atmosphere. After the solvent was evaporated, the residue was purified by silica gel column chromatography (hexane:ethyl acetate=85:15→50:50) to yield the title compound (601 mg) as a yellow powder (mp: 137.0-140.0° C.).

$^1$H NMR (200 MHz, CDCl$_3$) δ ppm:
2.53 (3H, d, J=1.1 Hz), 7.53 (1H, d, J=1.1 Hz), 7.71 (1H, dd, J=8.5, 1.6 Hz), 8.13 (1H, dd, J=8.5, 0.6 Hz), 8.20 (1H, dd, J=1.6, 0.5 Hz), 9.07 (1H, s)

Example 41

Synthesis of Compound 227

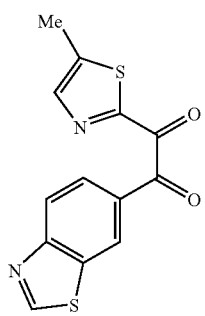

Potassium permanganate (733 mg) was added to Compound 226 (593 mg) in a mixed solution of acetone (45.7 ml)-buffer*(25.5 ml), and the mixture was stirred for 30 minutes at room temperature. The reaction solution was cooled on ice, and after sodium nitrite (297 mg) was added thereto slowly, 10% sulfuric acid (3.0 ml) was added dropwise thereto. After this solution was stirred for 15 minutes while cooling in ice, chloroform (100 ml) and water (30 ml) were added to the reaction solution, and then the resultant solution was filtered through celite. The filtrate was separated, and the aqueous layer was extracted again with chloroform (100 ml). The combined organic layer was dried over anhydrous magnesium sulfate, and then the solvent was evaporated. The residue was purified twice by silica gel column chromatography (neutral; hexane:ethyl acetate=65:35→45:55), (neutral; hexane:ethyl acetate=5:95) to yield the title compound (424 mg) as a yellow powder (mp: 154.0-155.0° C.).

buffer*: Sodium hydrogen carbonate (6.8 g) and anhydrous magnesium sulfate (68.0 g) were dissolved in water (3.0 l).

$^1$H NMR (300 MHz, CDCl$_3$) δ ppm:
2.65 (3H, d, J=1.1 Hz), 7.78 (1H, d, J=1.1 Hz), 8.15 (1H, dd, J=8.5, 1.7 Hz), 8.24 (1H, dd, J=8.5, 0.6 Hz), 8.63 (1H, dd, J=1.7, 0.6 Hz), 9.22 (1H, s)

Example 42

Synthesis of Compound 228

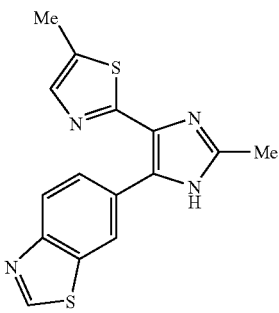

Acetaldehyde (0.15 ml) and a solution of ammonium acetate (900 mg) in methanol (10 ml) was added to a solution of Compound 227 (414 mg) in tetrahydrofuran (10 ml), and the mixture was stirred for 13 hours at room temperature. The reaction solution, to which a saturated aqueous solution of sodium hydrogen carbonate (70 ml) was added to neutralize, was extracted twice with ethyl acetate (150 ml). The organic layer was dried over anhydrous magnesium sulfate, and then the solvent was evaporated. The residue was purified by silica gel column chromatography (ethyl acetate→chloroform:methanol=90:10) and then recrystallized (n-hexane-ethyl acetate) to yield the title compound (230 mg) as a colorless powder (mp: 210.0-211.0° C.).

$^1$H NMR (300 MHz, DMSO-d6) δ ppm:
2.37 (3H, s), 2.42 (3H, s), 7.44 (1H, brs), 8.09-8.15 (2H, m), 8.78 (1H, br), 9.42 (1H, s), 12.53 (1H, br)

Example 43

Synthesis of Compound 239

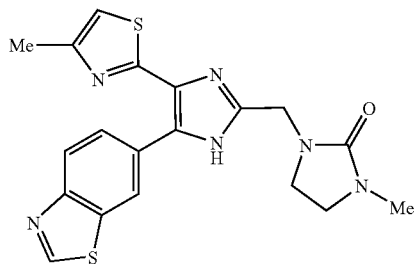

(1) Imidazole (9.63 g) and chloro-tert-butyldimethylsilane (9.77 g) were added to a solution of 1-(2-hydroxyethyl)-2-imidazolidinone (7.67 g) in N,N-dimethylformamide (75 ml), and the mixture was stirred for 2 hours at room temperature. The reaction solution was charged with water and diluted with ethyl acetate, and then the organic layer was washed with a brine. The organic layer was dried over anhydrous magnesium sulfate, and then the solvent was evaporated.

The residue was purified by silica gel column chromatography (hexane:ethyl acetate=35:65→0:100) to yield 1-[2-(tert-butyldimethylsilaniloxy)ethyl]imidazolidin-2-one (8.73 g) as a colorless solid (mp: 53.5-57.0° C.).

$^1$H NMR (200 MHz, CDCl$_3$) δ ppm:
0.06 (6H, s), 0.89 (9H, s), 3.30 (2H, t, J=5.3 Hz), 3.34-3.46 (2H, m), 3.54-3.65 (2H, m), 3.74 (2H, t, J=5.3 Hz)

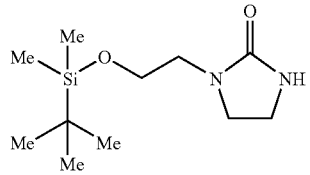

(2) Sodium hydride (393 mg) was washed twice with hexane, and then tetrahydrofuran (10 ml) was added thereto. A vessel was cooled in an ice bath, to which a solution of 1-[2-(tert-butyldimthylsilaniloxy) ethyl]imidazolidin-2-one (2.00 g) in tetrahydrofuran (10 ml) was added dropwise while keeping a temperature inside the vessel at below 10° C. After this solution was stirred for 15 minutes, iodomethane (766 μl) was added dropwise thereto at the same temperature, and the mixture was stirred for 20 minutes at room temperature. Water was added thereto so as to quench the reaction, and this solution was diluted with ethyl acetate. This mixture was washed with 2N hydrochloric acid, a saturated aqueous solution of sodium hydrogen carbonate, and a brine successively. The organic layer was dried over anhydrous magnesium sulfate, and then the solvent was evaporated. The residue was purified by silica gel column chromatography (hexane:ethyl acetate=35:65→0:100, chloroform:methanol=4:1) to yield a mixture of oily substances (*). All of the aqueous layers were combined together and condensed, and the resultant residue was suspended in a mixture of chloroform-methanol, and then this mixture was filtered. After the resultant material was dried over anhydrous magnesium sulfate, the solvent was evaporated. The residue and the previously obtained mixture of oils (*) were purified by silica gel column chromatography (chloroform:methanol=9:1) to yield 1-(2-hydroxyethyl)-3-methylimidazolidin-2-one (907 mg) as a light yellow oil.

$^1$H NMR (300 MHz, CDCl$_3$) δ ppm:
2.80 (3H, s), 3.29-3.45 (6H, m), 3.74-3.79 (2H, m)

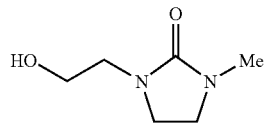

(3) A Dess-Martin reagent (1.094 g) was added to a solution of 1-(2-hydroxyethyl)-3-methylimidazolidin-2-one (372 mg) in chloroform (10 ml), and the mixture was stirred for 1.5 hours at room temperature. This reaction solution, to which methanol (10 ml), Compound 204 (400 mg), and ammonium acetate (856 mg) were added, was stirred for 2.5 hours at room temperature. After the reaction solution was diluted with chloroform, this solution was washed with a saturated aqueous solution of sodium hydrogen carbonate. After the organic layer was dried over anhydrous magnesium sulfate, the solvent was evaporated. The residue was purified three times by silica gel column chromatography (chloroform:methanol=20:1→15:1), (chloroform:acetone=2:1→1:1) and by NH-type of silica gel column chromatography (chloroform), and then recrystallized (ethyl acetate-diethylether) to yield the title compound (27 mg) as a colorless powder (mp: 232.0-233.5° C.).

$^1$H NMR (200 MHz, CDCl$_3$) δ ppm:
2.45 (3H, d, J=0.9 Hz), 2.83 (3H, s), 3.30-3.54 (4H, m), 4.47 (2H, s), 6.75 (1H, s), 7.89 (1H, dd, J=8.6, 1.5 Hz), 8.12-8.21 (1H, m), 9.03 (1H, s)

Example 44

Synthesis of Compound 240

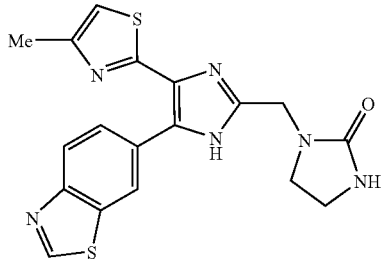

(1) Sodium hydride (393 mg) was washed twice with hexane, and then tetrahydrofuran (10 ml) was added thereto. A vessel was cooled in an ice bath, to which a solution of a compound synthesized in Example 43-(1) (2.00 g) in tetrahydrofuran (10 ml) was added dropwise while keeping a temperature inside the vessel at below 10° C. After this solution was stirred for 5 minutes, a solution of di-tert-butyl dicarbonate (2.31 g) in tetrahydrofuran (10 ml) was added dropwise thereto at the same temperature, and the mixture was stirred for 2 hours at room temperature and then for 18 hours at 50° C. A saturated aqueous solution of ammonium chloride and ethyl acetate were successively added to this reaction mixture, and after the organic layers were washed with a brine and dried over anhydrous magnesium sulfate, the solvent was evaporated. The residue was purified by silica gel column chromatography (hexane:ethyl acetate=2:1) to yield tert-butyl 3-[2-(tert-butyldimethylsilanyloxy)ethyl]-2-oxoimidazolidine-1-carboxylate (1.54 g) as a colorless powder (mp: 35.5-45.5° C.).

$^1$H NMR (300 MHz, CDCl$_3$) δ ppm:
0.05 (6H, s), 0.89 (9H, s), 1.53 (9H, s), 3.35 (2H, t, J=5.2 Hz), 3.48-3.55 (2H, m), 3.71-3.79 (4H, m)

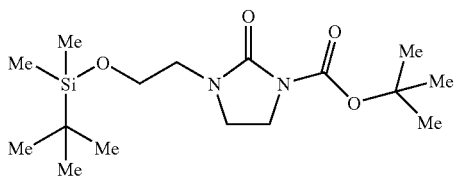

(2) A 1.0M solution of tetra-n-butylammonium fluoride in tetrahydrofuran (4.35 ml) was added to a solution of tert-butyl 3-[2-(tert-butyldimethylsilanyloxy)ethyl]-2-oxoimidazolidine-1-carboxylate (1.50 g) in tetrahydrofuran (15 ml), and the mixture was stirred for 1 hour at room temperature.

Methanol (1 ml) was added to the reaction solution, and the solvent was evaporated. The residue was purified by silica gel column chromatography (chloroform:methanol=20:1→10:1) to yield tert-butyl 3-(2-hydroxyethyl)-2-oxoimidazolidine-1-carboxylate (940 mg) as a colorless oil.

$^1$H NMR (200 MHz, CDCl$_3$) δ ppm:
1.39-1.58 (9H, m), 3.27-3.86 (8H, m)

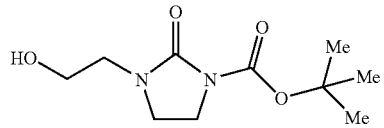

(3) A Dess-Martin reagent (1.47 g) was added to a solution of tert-butyl 3-(2-hydroxyethyl)-2-oxoimidazolidine-1-carboxylate (800 mg) in chloroform (8 ml), and the mixture was stirred for 1 hours at room temperature. This reaction mixture was diluted with ethyl acetate and filtered through celite, and a solvent in the filtrate was evaporated. The residue, to which tetrahydrofuran (30 ml), methanol (15 ml), Compound 204 (1.00 g), and ammonium acetate (2.14 g) were added, was stirred for 16 hours at room temperature. After the reaction solution was diluted with chloroform, this solution was washed with a saturated aqueous solution of sodium hydrogen carbonate. The aqueous layer was extracted with chloroform. After the organic layers were combined together and dried over anhydrous magnesium sulfate, the solvent was evaporated. The residue was purified by silica gel column chromatography (chloroform:methanol=40:1→20:1) to yield tert-butyl 3-[5-benzothiazol-6-yl-4-(4-methylthiazol-2-yl)-1H-imidazol-2-ylmethyl]-2-oxoimidazolidine-1-carboxylate (983 mg) as a light yellow amorphous.

$^1$H NMR (300 MHz, CDCl$_3$) δ ppm:
1.49 (9H, s), 2.44 (3H, d, J=0.9 Hz), 3.50-3.58 (2H, m), 3.76-3.84 (2H, m), 4.58 (2H, s), 6.76 (1H, s), 7.88-7.96 (1H, m), 8.14 (1H, d, J=8.7 Hz), 9.03 (1H, s)

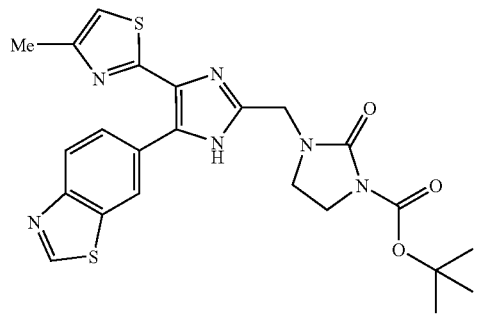

(4) 4N hydrochloric acid/ethyl acetate (4.03 ml) was added to a solution of tert-butyl 3-[5-benzothiazol-6-yl-4-(4-methylthiazol-2-yl)-1H-imidazol-2-ylmethyl]-2-oxoimidazolidine-1-carboxylate (800 mg) in methanol (8 ml), and the mixture was stirred for 18 hours at room temperature. After the reaction solution was diluted with chloroform, this solution was washed with a saturated aqueous solution of sodium hydrogen carbonate. The aqueous layer was extracted with chloroform. After the organic layers were combined together and dried over anhydrous magnesium sulfate, the solvent was evaporated. The residue was purified by silica gel column chromatography (chloroform:methanol=20:1→10:1) and recrystallized (chloroform-ethyl acetate) to yield the title compound (392 mg) as a colorless powder (mp: 236.0-237.0° C.).

$^1$H NMR (300 MHz, DMSO-d6) δ ppm:
2.34 (3H, s), 3.23-3.32 (2H, m), 3.40-3.48 (2H, m), 4.35 (2H, s), 6.53 (1H, s), 7.16 (1H, d, J=0.9 Hz), 8.10-8.17 (2H, m), 8.86 (1H, brs), 9.44 (1H, s), 12.83 (1H, brs)

Example 45

Synthesis of Compound 242

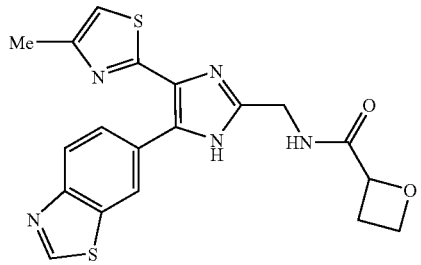

(1) Sulfuric acid (2.86 ml) and water (6 ml) were successively added to a solution of chromium (VI) oxide in water (3 ml) while ice-cooling. This solution was added dropwise to a solution of 2-hydroxymethyloxetane (1.00 g) in acetone (22 ml) while ice-cooling with an inside temperature kept below 20° C., and the mixture was stirred for 2 hours at room temperature. 2-propanol was added thereto so as to quench the reaction, and this solution was diluted with ethyl acetate and filtered through celite. The filtrate was washed with a brine and the aqueous layer was extracted twice with ethyl acetate. After the organic layers were combined together and dried over anhydrous magnesium sulfate, the solvent was evaporated. The residue was purified by silica gel column chromatography (neutral, chloroform:methanol=9:1→4:1) to yield oxetane-2-caboxylic acid (83 mg) as a light yellow oil.

$^1$H NMR (200 MHz, CDCl$_3$) δ ppm:
2.70-2.90 (1H, m), 3.01-3.21 (1H, m), 4.68-4.87 (2H, m), 5.19 (1H, dd, J=9.2, 6.6 Hz)

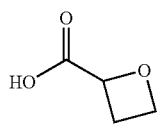

(2) 1-ethyl-3-(3-dimethylaminopropyl)-carbodiimide hydrochloride (167 mg) was added to a solution of Compound 70 (301 mg), oxetane-2-carboxylic acid (74 mg), and 1-hydroxybenzotriazole monohydrate (118 mg) in N,N-dimethylformamide (1.5 ml), and the mixture was stirred for 3 hours at room temperature. After the reaction mixture was diluted with chloroform, this mixture was washed with a saturated aqueous solution of sodium hydrogen carbonate. The aqueous layer was extracted twice with chloroform. After the organic layers were combined together and dried over anhydrous magnesium sulfate, the solvent was evaporated. The residue was purified by silica gel column chromatography (chloroform:methanol=30:1→15:1) and recrystallized (chloroform-ethyl acetate) to yield the title compound (265 mg) as a colorless powder (mp: 224.5-226.5° C.).

$^1$H NMR (300 MHz, DMSO-d6) δ ppm:

2.34 (3H, s), 2.52-2.63 (1H, m), 2.86-3.00 (1H, m), 4.38-4.67 (4H, m), 4.99 (1H, dd, J=9.0, 6.5 Hz), 7.15 (1H, d, J=0.9 Hz), 8.03-8.17 (2H, m), 8.52 (1H, t, J=5.8 Hz), 8.87 (1H, s), 9.44 (1H, s), 12.72 (1H, s)

Compounds listed in Table 1 were obtained by performing the same procedures as Examples 1 to 48, using corresponding materials.

Example 46

Synthesis of Compound 250

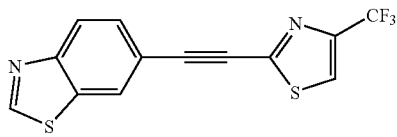

(1) t-Butyl nitrite (679 mg) was added dropwise to a solution of 2-amino-4-trifluoromethylthiazole (1.00 g) in acetonitrile (10 ml) while ice-cooling, and then copper (I) iodide (1.25 g) was gradually added thereto. The reaction mixture was stirred for 2 hours at 0° C., then charged with 1N hydrochloric acid (100 ml) and extracted twice with ethyl acetate (100 ml). The organic layer was added silica gel, then the solvent was evaporated. The residue was purified by silica gel column chromatography (hexane:ethyl acetate=80:20) to yield 2-iodo-4-trifluoromethylthiazole (747 mg) as a brown solid (mp: 35.5-36.0° C.).

$^1$H NMR (300 MHz, CDCl$_3$) δ ppm:

7.75 (1H, q, J=0.9 Hz)

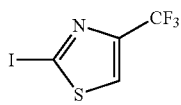

(2) To a solution of 6-ethynylbenzothiazole (402 mg) synthesized in Example 17-(2) and 2-iodo-4-trifluoromethylthiazole (708 mg) in acetonitrile (8 ml), triethylamine (12.5 ml) and tetrakis(triphenylphosphine)palladium (151 mg) were added under nitrogen atmosphere, and then was heated under reflux for 3 hours under nitrogen atmosphere. After the solvent was evaporated, the residue was purified by silica gel column chromatography (hexane:ethyl acetate=85:15→70:30) to yield the title compound (573 mg) as a yellow powder (mp: 153.0-154.0° C.)

$^1$H NMR (300 MHz, CDCl$_3$) δ ppm:

7.74 (1H, dd, J=8.5, 1.6 Hz), 7.81 (1H, q, J=0.9 Hz), 8.16 (1H, dd, J=8.5, 0.6 Hz), 8.24 (1H, dd, J=1.7, 0.6 Hz), 9.11 (1H, s)

Example 47

Synthesis of Compound 251

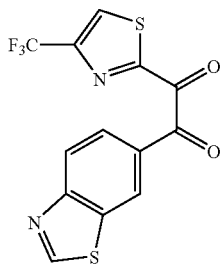

Potassium permanganate (572 mg) was added to Compound 250 (562 mg) in a mixed solution of acetone (35.9 ml)-buffer* (20.0 ml), and the mixture was stirred for 30 minutes at room temperature. The reaction mixture was cooled on ice, and after sodium nitrite (234 mg) was added thereto slowly, 10% sulfuric acid (2.4 ml) was added dropwise thereto. After this solution was stirred for 15 minutes while cooling in ice, chloroform (100 ml) and water (30 ml) were added to the reaction solution, and then the resultant solution was filtered through celite. The filtrate was separated, and the aqueous layer was extracted again with chloroform (100 ml). The combined organic layer was dried over anhydrous magnesium sulfate, and then the solvent was evaporated. The residue was purified by silica gel column chromatography (neutral; hexane:ethyl acetate=50:50) to yield the title compound (113 mg) as a yellow powder (mp: 163.5-164.5° C.).

buffer*: Sodium hydrogen carbonate (6.8 g) and anhydrous magnesium sulfate (68.0 g) were dissolved in water (3.0 l)

$^1$H NMR (300 MHz, CDCl$_3$) δ ppm:

8.14-8.32 (3H, m), 8.69 (1H, m), 9.27 (1H, s)

Example 48

Synthesis of Compound 244

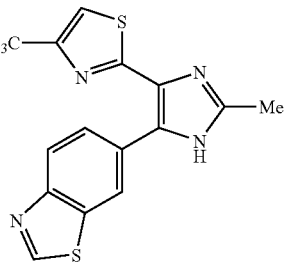

Acetaldehyde (0.15 ml) and a solution of ammonium acetate (194 mg) in methanol (3 ml) were added to a solution of Compound 251 (107 mg) in tetrahydrofuran (5 ml), and the mixture was stirred for 3.5 hours at room temperature. The reaction mixture was neutralized by addition of aqueous sodium hydrogen carbonate solution (50 ml), and was extracted twice with ethyl acetate (100 ml). The organic layer was dried over anhydrous magnesium sulfate, and then the solvent was evaporated. The residue was purified by silica gel column chromatography (hexane:ethyl acetate=30:70→1:99) and then recrystallized (n-hexane-ethyl acetate) to yield the title compound (25 mg) as a colorless powder (mp: 190.5-192.0° C.).

¹H NMR (300 MHz, DMSO-d6) δ ppm:
2.40 (3H, s), 8.03 (1H, dd, J=8.6, 1.5 Hz), 8.15 (1H, d, J=8.6 Hz), 8.34 (1H, s), 8.89 (1H, brs), 9.45 (1H, s), 12.78 (1H, br)

TABLE 1

| Compound No. | Structural Formula of Compound | Salt form if applicable | Mp (° C.) | 1H-NMR |
|---|---|---|---|---|
| Compound 1 | | | | (300 MHz, DMSO-d6) δppm: 6.11 (2H, s), 7.07 (1H, d, J = 7.9 Hz), 7.52 (1H, bd, J = 7.9 Hz), 7.61-7.72 (2H, m), 7.81 (1H, d, J = 3.4 Hz), 7.98 (2H, d, J = 8.4 Hz), 8.27 (2H, d, J = 8.4 Hz), 13.10 (1H, bs) |
| Compound 2 | | | 240.0-249.0 | (300 MHz, DMSO-d6) δppm: 6.11 (2H, s), 7.06 (1H, d, J = 7.8 Hz), 7.43 (1H, bs), 7.53 (1H, bd, J = 7.8 Hz), 7.60-7.70 (2H, m), 7.80 (1H, d, J = 3.3 Hz), 7.93-8.07 (3H, m), 8.16 (2H, d, J = 8.2 Hz), 12.90 (1H, bs) |
| Compound 3 | | | | (300 MHz, DMSO-d6) δppm: 7.65 (1H, m), 7.92 (1H, d, J = 3.3 Hz), 8.02 (2H, d, J = 8.2 Hz), 8.08 (1H, d, J = 3.3 Hz), 8.24 (1H, m), 8.46 (2H, d, J = 8.2 Hz), 8.75-9.00 (2H, m) |
| Compound 4 | | | 255.5-256.0 | (300 MHz, DMSO-d6) δppm: 7.34-7.48 (2H, m), 7.77 (1H, d, J = 3.3 Hz), 7.88-8.10 (5H, m), 8.25-8.40 (2H, m), 8.74 (1H, d, J = 4.0 Hz), 9.05 (1H, m), 13.41 (1H, bs) |
| Compound 5 | | | | (300 MHz, CDCl3) δppm: 1.69 (3H, d, J = 6.5 Hz), 5.19 (1H, q, J = 6.5 Hz), 6.02 (2H, s), 6.89 (1H, d, J = 8.4 Hz), 7.13-7.23 (2H, m), 7.34 (1H, s), 7.72 (2H, d, J = 8.7 Hz), 8.04 (2H, d, J = 8.7 Hz), 10.64 (1H, bs) |

TABLE 1-continued

| Compound No. | Structural Formula of Compound | Salt form if applicable | Mp (° C.) | 1H-NMR |
|---|---|---|---|---|
| Compound 6 | | | 140.0-148.0 | (300 MHz, DMSO-d6) δppm: 1.47 (3H, m), 4.95 (1H, m), 5.95-6.28 (3H, m), 6.93 (1H, m), 7.13-7.45 (3H, m), 7.68 (1H, m), 7.90-8.05 (3H, m), 8.15 (2H, d, J = 8.1 Hz), 12.72 (1H, m) |
| Compound 7 | | | 153.0-159.0 | (300 MHz, DMSO-d6) δppm: 2.57 (3H, s), 6.07 (2H, s), 7.02 (1H, bs), 7.25-7.47 (3H, m), 7.94-8.05 (3H, m), 8.17 (2H, d, J = 8.5 Hz), 8.26 (1H, s), 12.85 (1H, bs) |
| Compound 8 | | | | (300 MHz, DMSO-d6) δppm: 2.36 (3H, s), 6.10 (2H, s), 7.06 (1H, d, J = 7.6 Hz), 7.20 (1H, s), 7.55 (1H, bd, J = 7.6 Hz), 7.73 (1H, bs), 7.97 (2H, d, J = 8.3 Hz), 8.26 (2H, d, J = 8.3 Hz), 13.05 (1H, bs) |
| Compound 9 | | | 276.0-277.0 | (300 MHz, DMSO-d6) δppm: 2.36 (3H, s), 6.10 (2H, s), 7.05 (1H, d, J = 8.1 Hz), 7.18 (1H, s), 7.42 (1H, bs), 7.58 (1H, bd, J = 8.1 Hz), 7.75 (1H, bs), 7.94-8.08 (3H, m), 8.15 (2H, d, J = 8.2 Hz), 12.87 (1H, bs) |
| Compound 10 | | | | (300 MHz, DMSO-d6) δppm: 1.26 (3H, t, J = 7.6 Hz), 2.71 (2H, q, J = 7.6 Hz), 6.10 (2H, s), 7.05 (1H, d, J = 8.1 Hz), 7.21 (1H, s), 7.58 (1H, bd, J = 8.1 Hz), 7.80 (1H, bs), 7.97 (2H, d, J = 8.4 Hz), 8.26 (2H, d, J = 8.4 Hz), 13.05 (1H, bs) |

TABLE 1-continued

| Compound No. | Structural Formula of Compound | Salt form if applicable | Mp (° C.) | 1H-NMR |
|---|---|---|---|---|
| Compound 11 | 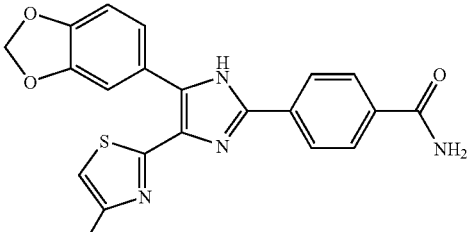 | | 259.5-261.5 | (300 MHz, DMSO-d6) δppm: 1.26 (3H, t, J = 7.5 Hz), 2.71 (2H, q, J = 7.5 Hz), 6.10 (2H, s), 7.05 (1H, d, J = 8.1 Hz), 7.19 (1H, 3), 7.42 (1H, bs), 7.59 (1H, bd, J =8.1 Hz), 7.82 (1H, bs), 7.99 (2H, d, J = 8.2 Hz), 8.04 (1H, bs), 8.15 (2H, d, J = 8.2 Hz), 12.87 (1H, bs) |
| Compound 12 | 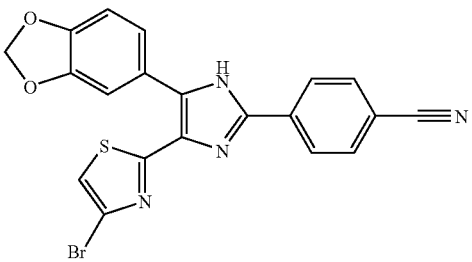 | | | (300 MHz, DMSO-d6) δppm: 6.12 (2H, s), 7.08 (1H, d, J = 8.4 Hz), 7.49 (1H, bd, J = 8.4 Hz), 7.63 (1H, bs), 7.75 (1H, s), 7.97 (2H, d, J = 8.2 Hz), 8.25 (2H, d, J = 8.2 Hz) |
| Compound 13 | 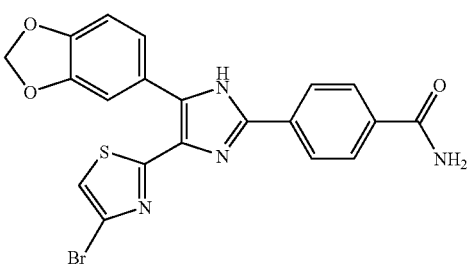 | | 273.0-275.5 | (300 MHz, DMSO-d6) δppm: 6.12 (2H, s), 7.08 (1H, d, J = 8.4 Hz), 7.38-7.53 (2H, m), 7.63 (1H, bs), 7.74 (1H, s), 7.99 (2H, d, J = 8.2 Hz), 8.04 (1H, bs), 8.14 (2H, d, J = 8.2 Hz), 13.03 (1H, bs) |
| Compound 14 | 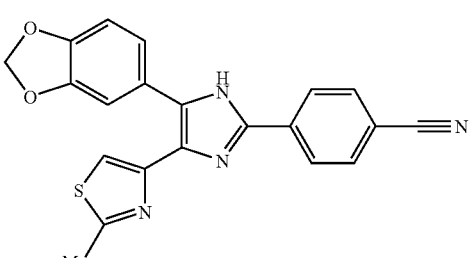 | | | (300 MHz, CDCl3) δppm: 2.74 (3H, s), 6.01 (2H, s), 6.88 (1H, d, J = 7.8 Hz), 7.14-7.24 (3H, m), 7.70 (2H, d, J = 8.7 Hz), 8.05 (2H, d, J = 8.7 Hz) |
| Compound 15 | 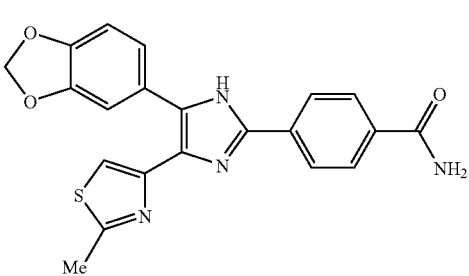 | | | (300 MHz, CDCl3) δppm: 2.76 (3H, s), 6.01 (2H, s), 6.69 (1H, d, J = 8.4 Hz), 7.15-7.25 (3H, m), 7.89 (2H, d, J = 8.7 Hz), 8.04 (2H, d, J = 8.7 Hz) |

TABLE 1-continued

| Compound No. | Structural Formula of Compound | Salt form if applicable | Mp (° C.) | 1H-NMR |
|---|---|---|---|---|
| Compound 16 | | | 295.0-295.5 | (300 MHz, DMSO-d6) δppm: 2.34 (3H, s), 7.24 (1H, s), 8.00 (2H, d, J = 8.5 Hz), 8.10-8.37 (4H, m), 8.86 (1H, brs), 9.48 (1H, s), 13.33 (1H, brs) |
| Compound 17 | | | 283.5-286.0 | (300 MHz, DMSO-d6) δppm: 2.35 (3H, 3), 7.21 (1H, 3), 7.34 (2H, dd, J = 8.9, 8.9 Hz), 7.98 (2H, d, J = 8.3 Hz), 8.08 (2H, m), 8.26 (2H, d, 3 = 8.3 Hz), 13.20 (1H, bs) |
| Compound 18 | | | 281.0-281.5 | (300 MHz, DMSO-d6) δppm: 2.35 (3H, s), 7.19 (1H, 3), 7.34 (2H, dd, J = 8.6, 8.6 Hz), 7.43 (1H, bs), 7.94-8.24 (7H, m), 13.02 (1H, bs) |
| Compound 19 | | | 205.5-208.0 | (300 MHz, CDCl3) δppm: 2.39 (38, d, J = 0.9 Hz), 6.00 (2H, 3). 6.60 (1H, d, J = 0.9 Hz), 6.84 (1H, d, J = 7.9 Hz), 7.15 (1H, dd, J = 7.9, 1.7 Hz), 7.19 (1H, d, J = 1.7 Hz) |
| Compound 20 | | | 169.0-173.0 | (300 MHz, DMSO-d6) δppm: 2.09 (3H, s), 2.34 (3H, d, J = 0.9 Hz), 6.07 (2H, s), 6.98 (1H, d, J = 8.2 Hz), 7.13 (1H, d, J = 0.9 Hz), 7.45 (1H, dd, J = 8.2, 1.7 Hz), 7.78 (1H, d, J = 1.7 Hz), 11.28 (1H, bs). 11.76 (1H, bs) |

TABLE 1-continued

| Compound No. | Structural Formula of Compound | Salt form if applicable | Mp (° C.) | 1H-NMR |
|---|---|---|---|---|
| Compound 21 | | | | (300 MHz, DMSO-d6) δppm: 0.93 (3H, t, J = 7.3 Hz), 1.63 (2H, qt, J = 7.3, 7.3 Hz), 2.28-2.41 (5H, m), 6.07 (2H, s), 6.98 (1H, d, J = 8.1 Hz), 7.12 (1H, s), 7.46 (1H, bd, J = 8.1 Hz), 7.79 (1H, bs), 11.25 (1H, bs), 11.78 (1H, bs) |
| Compound 22 | | | 223.0-225.0 | (300 MHz, DMSO-d6) δppm: 2.36 (3H, s), 6.08 (2H, s), 7.01 (1H, d, J = 8.2 Hz), 7.15 (1H, d, J = 1.1 Hz), 7.48-7.68 (4H, m), 7.83 (1H, bs), 8.09 (2H, J = 8.5 Hz), 11.57 (1H, bs), 12.21 (1H, bs) |
| Compound 23 | | | | (300 MHz, DMSO-d6) δppm: 2.34 (3H, d, J = 0.9 Hz), 3.71 (2H, s), 6.07 (2H, s), 7.00 (1H, d, J = 8.2 Hz), 7.10 (1H, d, J = 0.9 Hz), 7.47 (1H, dd, J = 8.2, 1.7 Hz), 7.75 (1H, bs) |
| Compound 24 | | | 181.0-184.0 | (300 MHz, DMSO-d6) δppm: 0.88 (3H, t, J = 7.4 Hz), 1.54 (2H, qt, J = 7.4, 7.4 Hz), 2.12 (2H, t, J = 7.4 Hz), 2.34 (3H, s), 4.31 (2H, d, J = 5.4 Hz), 6.07 (2H, s), 7.00 (1H, d, J = 8.1 Hz), 7.12 (1H, d, J = 0.8 Hz), 7.47 (1H, bs), 7.77 (1H, bs), 8.30 (1H, t, J = 5.4 Hz), 12.45 (1H, bs) |
| Compound 25 | | | 217.5-219.0 | (300 MHz, DMSO-d6) δppm: 2.34 (3H, s), 4.55 (2H, d, J = 5.4 Hz), 6.07 (2H, s), 7.00 (1H, d, J = 8.1 Hz), 7.11 (1H, s), 7.42-7.59 (4H, m), 7.77 (1H, bs), 7.92 (2H, d, J = 8.4 Hz), 8.32 (1H, t, J = 5.4 Hz), 12.51 (1H, bs) |

TABLE 1-continued

| Compound No. | Structural Formula of Compound | Salt form if applicable | Mp (° C.) | 1H-NMR |
|---|---|---|---|---|
| Compound 26 | | | 165.5-169.5 | (300 MHz, DMSO-d6) δppm: 2.34 (3H, s), 3.42 (2H, s), 3.72 (3H, s), 4.31 (2H, d, J = 5.3 Hz), 6.07 (2H, s), 6.85 (2H, J = 8.6 Hz), 7.01 (1H, d, J = 8.2 Hz), 7.13 (1H, d, J = 0.9 Hz), 7.22 (2H, J = 8.6 Hz), 7.48 (1H, dd, J = 8.2, 1.7 Hz), 7.78 (1H, d, J = 1.7 Hz), 8.53 (1H, t, J = 5.3 Hz), 12.48 (1H, bs) |
| Compound 27 | | | 155.5-157.5 | (300 MHz, CDCl3) δppm: 2.44 (3H, d, J = 0.9 Hz), 2.91 (2H, t, J = 5.9 Hz), 3.18 (2H, t, J = 5.9 Hz), 6.00 (2H, s), 6.70 (1H, d, J = 0.9 Hz), 6.86 (1H, d, J = 8.1 Hz), 7.24 (1H, dd, J = 8.1, 1.7 Hz), 7.36 (1H, d, J = 1.7 Hz) |
| Compound 28 | | | 148.0-150.0 | (300 MHz, DMSO-d6) δppm: 0.83 (3H, t, J = 7.4 Hz), 1.50 (2H, qt, J = 7.4, 7.4 Hz), 2.04 (2H, t, J = 7.4 Hz), 2.34 (3H, s), 2.79 (t, J = 7.3 Hz), 3.42 (2H, td, J = 7.3, 5.4 Hz), 6.07 (2H, s), 7.00 (1H, d, J = 7.9 Hz), 7.10 (1H, s), 7.51 (1H, bd, J = 7.9 Hz), 7.82 (1H, bs), 7.94 (1H, t, J = 5.4 Hz), 12.29 (1H, bs) |
| Compound 29 | | | | (200 MHz, CDCl3) δppm: 1.90 (2H, tt, J = 6.4, 6.4 Hz), 2.43 (3H, d, J = 0.9 Hz), 2.84-3.01 (4H, m), 5.99 (2H, s), 6.69 (1H, d, J = 0.9 Hz), 6.84 (1H, d, J = 8.1 Hz), 7.26 (1H, dd, J = 8.1, 1.7 Hz), 7.38 (1H, d, J = 1.7 Hz) |
| Compound 30 | | | 134.5-138.5 | (300 MHz, CDCl3) δppm: 0.96 (3H, t, J = 7.4 Hz), 1.69 (2H, qt, J = 7.4, 7.4 Hz), 1.80-1.94 (2H, m), 2.22 (2H, t, J = 7.4 Hz), 2.45 (3H, d, J = 0.9 Hz), 2.79 (t, J = 6.2 Hz), 3.40 (2H, td, J = 6.2, 5.9 Hz), 5.99 (2H, s), 6.03 (1H, bs), 6.72 (1H, s), 6.87 (1H, d, J = 8.1 Hz), 7.39 (1H, bd, J = 8.1 Hz), 7.55 (1H, bs) |

TABLE 1-continued

| Compound No. | Structural Formula of Compound | Salt form if applicable | Mp (° C.) | 1H-NMR |
|---|---|---|---|---|
| Compound 31 | | | | (200 MHz, DMSO-d6) δppm: 1.82 (2H, tt, J = 7.7, 6.9 Hz), 2.15 (6H, s), 2.28 (2H, t, J = 6.9 Hz), 2.35 (3H, d, J = 0.9 Hz), 2.66 (2H, t, J = 7.7 Hz), 6.07 (2H, s), 6.99 (1H, d, J = 8.1 Hz), 7.09 (1H, d, J = 0.9 Hz), 7.46 (1H, bd, J = 8.1 Hz), 7.75 (1H, bs), 12.33 (1H, bs) |
| Compound 32 | | | | (300 MHz, CDCl3) δppm: 1.57 (2H, tt, J = 7.4, 7.4 Hz), 1.86 (2H, tt, J = 7.4, 7.4 Hz), 2.42 (3H, d, J = 0.9 Hz), 2.74-2.86 (4H, m), 6.00 (2H, s), 6.68 (1H, d, J = 0.9 Hz), 6.85 (1H, d, J = 8.1 Hz), 7.21 (1H, dd, J = 8.1, 1.7 Hz), 7.28 (1H, bs) |
| Compound 33 | | | 132.0-133.0 | (300 MHz, DMSO-d6) δppm: 0.83 (3H, t, J = 7.4 Hz), 1.38-1.58 (4H, m), 1.69 (2H, tt, J = 7.4, 7.4 Hz), 2.02 (2H, t, J = 7.4 Hz), 2.34 (3H, s), 2.65 (t, J = 7.5 Hz), 3.07 (2H, td, J = 7.5, 5.4 Hz), 6.06 (2H, s), 6.99 (1H, d, J = 8.2 Hz), 7.09 (1H, d, J = 0.9 Hz), 7.50 (1H, bd, J = 8.2 Hz), 7.77 (1H, t, J = 5.4 Hz), 7.82 (1H, bs), 12.20 (1H, bs) |
| Compound 34 | | | | (300 MHz, DMSO-d6) δppm: 2.34 (3H, d, J = 0.9 Hz), 6.08 (2H, s), 6.99 (1H, d, J = 8.2 Hz), 7.21 (1H, d, J = 0.9 Hz), 7.48 (1H, dd, J = 8.2, 1.7 Hz), 7.60 (1H, d, J = 1.7 Hz) |
| Compound 35 | | | 199.6-200.0 | (300 MHz, DMSO-d6) δppm: 0.89 (3H, t J = 7.3 Hz), 1.56 (2H, qt, J = 7.3, 7.3 Hz), 2.34 (3H, s), 3.24 (2H, td, J = 7.3, 5.4 Hz), 6.07 (2H, s), 6.97 (1H, d, J = 8.2 Hz), 7.20 (1H, s), 7.45 (1H, bd, J = 8.2 Hz), 7.58 (1H, bs), 8.42 (1H, t, J = 5.4 Hz), 13.45 (1H, bs) |

TABLE 1-continued

| Compound No. | Structural Formula of Compound | Salt form if applicable | Mp (° C.) | 1H-NMR |
|---|---|---|---|---|
| Compound 36 | | | 222.0-222.5 | (300 MHz, DMSO-d6) δppm; 2.36 (3H, s), 6.08 (2H, s), 6.99 (1H, d, J = 7.9 Hz), 7.12 (1H, 1, J = 7.3 Hz), 7.24 (1H, s), 7.37 (2H, dd, J = 7.5, 7.3 Hz), 7.47 (1H, bd, J = 7.9 Hz), 7.60 (1H, bs), 7.85 (2H, J = 7.5 Hz), 10.26 (1H, bs), 13.68 (1H, bs) |
| Compound 37 | | | | (200 MHz, DMSO-d6) δppm: 2.39 (3H, d, J = 1.0 Hz), 2.81 (2H, t, J = 7.1 Hz), 3.02 (2H, t, J = 7.1 Hz), 6.11 (2H, s), 7.06 (1H, d, J = 8.1 Hz), 7.23 (1H, d, J = 1.0 Hz), 7.33 (1H, dd, J = 8.1, 1.5 Hz), 7.51 (1H, bs) |
| Compound 38 | | | 106.5-108.5 | (200 MHz, CDCl3) δppm: 0.90 (3H, t J = 7.3 Hz), 1.51 (2H, qt, J = 7.3, 7.3 Hz), 2.43 (3H, d, J = 1.1 Hz), 2.66 (2H, m), 3.10 (2H, m), 3.24 (2H, td, J = 7.3, 5.4 Hz), 5.91 (1H, bs), 6.00 (2H, s), 6.71 (1H, d, J = 1.1 Hz), 6.85 (1H, d, J = 8.1 Hz), 7.23 (1H, dd, J = 8.1, 1.8 Hz), 7.39 (1H, bs) |
| Compound 39 | | | | (300 MHz, DMSO-d6) δppm: 1.93 (2H, tt, J = 7.4, 7.4 Hz), 2.26-2.41 (5H, m), 2.68 (2H, t, J = 7.4 Hz), 6.06 (2H, s), 6.99 (1H, d, J = 8.2 Hz), 7.10 (1H, s), 7.51 (1H, bd, J = 8.2 Hz), 7.82 (1H, bs), 12.08 (1H, bs), 12.25 (1H, bs) |
| Compound 40 | | | 75.0-79.0 | (300 MHz, DMSO-d6) δppm: 0.84 (3H, t, J = 7.3 Hz), 1.40 (2H, qt, J = 7.3, 7.3 Hz), 1.92 (2H, tt, J = 7.6, 7.6 Hz), 2.15 (2H, t, J = 7.6 Hz), 2.34 (3H, s), 2.64 (2H, t, J = 7.6 Hz), 3.00 (2H, td, J = 7.3, 5.4 Hz), 6.07 (2H, s), 6.99 (1H, d, J = 8.1 Hz), 7.10 (1H, s), 7.51 (1H, bd, J = 8.1 Hz), 7.81 (1H, t, J = 5.4 Hz), 7.83 (1H, bs), 12.24 (1H, bs) |

TABLE 1-continued

| Compound No. | Structural Formula of Compound | Salt form if applicable | Mp (° C.) | 1H-NMR |
|---|---|---|---|---|
| Compound 41 | | | | (300 MHz, CDCl3) δppm: 1.82 (2H, m), 2.05 (2H, m), 2.42 (3H, s), 2.53 (2H, t, J = 6.8 Hz), 3.28 (2H, t, J = 7.8 Hz), 6.03 (2H, s), 6.89 (1H, d, J = 0.9 Hz), 6.89 (1H, d, J = 8.1 Hz), 7.14 (1H, d, J = 1.7 Hz), 7.20 (1H, dd, J = 8.1, 1.7 Hz) |
| Compound 42 | | | | (300 MHz, CDCl3) δppm: 0.91 (3H, t, J = 7.3 Hz), 1.51 (2H, qt, J = 7.3, 7.3 Hz), 1.69-1.91 (4H, m), 2.27 (2H, t, J = 6.4 Hz), 2.44 (3H, d, J = 0.9 Hz), 2.84 (2H, t, J = 6.7 Hz), 3.21 (2H, td, J = 7.3, 6.1 Hz), 5.76 (1H, bs), 6.00 (2H, s), 6.71 (1H, d, J = 0.9 Hz), 6.86 (1H, d, J = 8.1 Hz), 7.33 (1H, bd, J = 8.1 Hz), 7.43 (1H, bs) |
| Compound 43 | | | | (300 MHz, CDCl3) δppm: 1.77-1.97 (4H, m), 2.43 (3H, d, J = 1.0 Hz), 2.48 (2H, t, J = 6.3 Hz), 2.89 (2H, t, J = 6.1 Hz), 6.00 (2H, 3), 6.71 (1H, d, J = 1.0 Hz), 6.85 (1H, d, J = 7.9 Hz), 7.10 (1H, t, J = 7.5 Hz), 7.24-7.39 (3H, m), 7.51 (2H, d, J = 8.4 Hz), 7.67 (1H, bs) |
| Compound 44 | | | 174.0-175.0 | (300 MHz, DMSO-d6) δppm: 1.52-1.74 (4H, m), 2.17 (2H, t, J = 6.1 Hz), 2.34 (3H, s), 2.65 (2H, t, J = 6.5 Hz), 3.69 (3H, s), 4.18 (2H, d, J = 5.9 Hz), 6.07 (2H, s), 6.84 (2H, d, J = 8.8 Hz), 6.99 (1H, d, J = 8.1 Hz), 7.09 (1H, s), 7.15 (2H, d, J = 8.8 Hz), 7.51 (1H, bd, J = 8.1 Hz), 7.83 (1H, bs), 8.25 (1H, t, J = 5.9 Hz), 12.22 (1H, bs) |
| Compound 45 | | | | (300 MHz, DMSO-d6) δppm: 1.48-1.75 (4H, m), 2.09 (2H, t, J = 7.2 Hz), 2.34 (3H, d, J = 1.0 Hz), 2.64 (2H, t, J = 7.5 Hz), 6.07 (2H, s), 6.72 (1H, bs), 6.99 (1H, d, J = 8.2 Hz), 7.09 (1H, d, J = 1.0 Hz), 7.26 (1H, bs), 7.50 (1H, dd, J = 8.2, 1.7 Hz), 7.82 (1H, d, J = 1.7 Hz), 12.21 (1H, bs) |

TABLE 1-continued

| Compound No. | Structural Formula of Compound | Salt form if applicable | Mp (° C.) | 1H-NMR |
|---|---|---|---|---|
| Compound 46 | 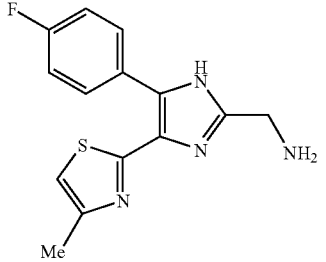 | | | (300 MHz, CDCl3) δppm: 2.42 (3H, d, J = 1.0 Hz), 4.08 (2H, s), 6.71 (1H, d, J = 1.0 Hz), 7.11 (2H, dd, J = 8.8, 8.8 Hz), 7.71 (2H, m) |
| Compound 47 | 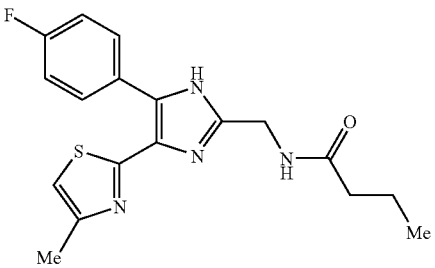 | | | (300 MHz, DMSO-d6) δppm: 0.88 (3H, t, J = 7.4 Hz), 1.54 (2H, qt, J = 7.4, 7.4 Hz), 2.13 (2H, t, J = 7.4 Hz), 2.33 (3H, 3), 4.33 (2H, d, J = 5.4 Hz), 7.13 (1H, s), 7.28 (2H, dd, J = 8.9, 8.9 Hz), 8.04 (2H, m), 8.32 (1H, t, J = 5.4 Hz), 12.58 (1H, bs) |
| Compound 48 | 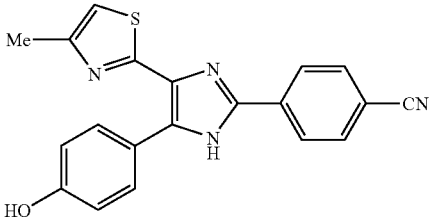 | | | (300 MHz, DMSO-d6) δppm: 2.35 (3H, d, J = 0.8 Hz), 6.85 (2H, d, J = 8.7 Hz), 7.14 (1H, d, J = 0.9 Hz), 7.84 (2H, d, J = 8.5 Hz),7.93 (2H, d, J = 8.5 Hz), 8.24 (2H, d, J = 8.7 Hz), 9.71 (1H, s), 12.95 (1H, s) |
| Compound 49 | 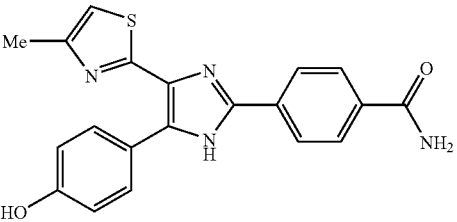 | | >300 | (300 MHz, DMSO-d6) δppm: 2.34 (3H, s), 6.87 (2H, d, J = 8.7 Hz), 7.14 (1H, s), 7.42 (1H, brs), 7.85 (2H, d, J = 8.5 Hz), 8.14 (2H, d, J = 8.4 Hz), 9.73 (1H, s), 7.99 (2H, d, J = 8.4 Hz), 8.04 (1H, brs), 12.82 (1H, brs) |
| Compound 50 | 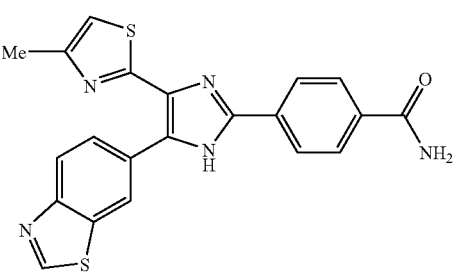 | | >300 | (300 MHz, DMSO-d6) δppm: 2.34 (3H, s), 7.22 (1H, s), 7.44 (1H, brs), 8.00-8.20 (7H, m), 8.87 (1H, brs), 9.47 (1H, s), 13.15 (3H, brs) |

TABLE 1-continued
| Compound No. | Structural Formula of Compound | Salt form if applicable | Mp (° C.) | 1H-NMR |
|---|---|---|---|---|
| Compound 51 | 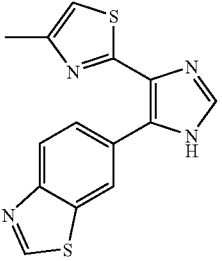 | | 210.0-211.0 | |
| Compound 52 | 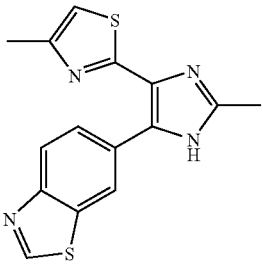 | | 217.5-218.0 | |
| Compound 53 | 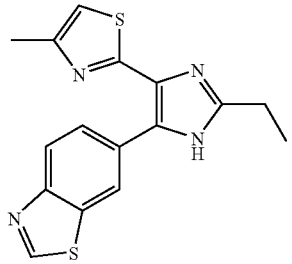 | HCl | | (300 MHz, DMSO-d6) δppm: 1.40 (3H, t, J = 7.6 Hz), 2.44 (3H, d, J = 0.9 Hz), 3.04 (2H, q, J = 7.6 Hz), 7.36 (1H, d, J = 1.1 Hz), 7.84 (1H, m), 8.29 (1H, m), 8.61 (1H, m), 9.58 (1H, s) |
| Compound 54 | 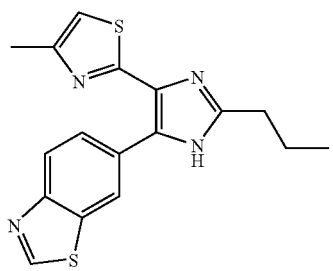 | | 144.5-146.0 | |
| Compound 55 | 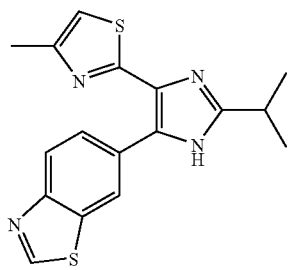 | | 155.0-155.5 | |

TABLE 1-continued

| Compound No. | Structural Formula of Compound | Salt form if applicable | Mp (° C.) | 1H-NMR |
|---|---|---|---|---|
| Compound 56 | | | 190.5-191.0 | |
| Compound 57 | | | | (300 MHz; CDCl3) δppm: 0.96 (3H, t, J = 7.3 Hz), 1.39-1.51 (2H, m), 1.75-1.85 (2H, m), 2.44 (3H, d, J = 1.1 Hz), 2.81 (2H, t, J = 7.7 Hz), 6.69 (1H, s), 7.86 (1H, dd, J = 8.5, 1.7 Hz), 8.17 (1H, dd, J = 8.5, 0.5 Hz), 8.39 (1H, s), 9.03 (1H, s) |
| Compound 58 | | HCl | 212.0-214.5 | |
| Compound 59 | | | 239.5-240.5 | |
| Compound 60 | | | | (300 MHz, CDCl3) δppm: 0.91 (3H, t, J = 7.1 Hz), 1.30-1.46 (4H, m), 1.74-1.87 (2H, m), 2.44 (3H, d, J = 0.8 Hz), 2.79 (2H, t, J = 7.8 Hz), 6.69 (1H, s), 7.86 (1H, dd, J = 8.5, 1.7 Hz), 8.17 (1H, d, J = 8.5 Hz), 8.38 (1H, s), 9.03 (1H, s) |

TABLE 1-continued
| Compound No. | Structural Formula of Compound | Salt form if applicable | Mp (° C.) | 1H-NMR |
|---|---|---|---|---|
| Compound 61 | 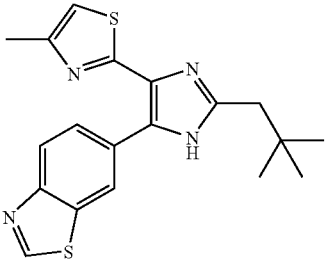 | HCl | | (300 MHz, DMSO-d6) δppm: 1.05 (9H, s), (3H, s), 2.91 (2H, s), 7.36 (1H, s), 7.85 (1H, m), 8.30 (1H, d, J = 8.5 Hz), 8.62 (1H, s), 9.59 (1H, s) |
| Compound 62 | 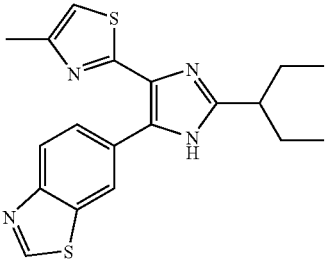 | HCl | 207.0-212.0 | |
| Compound 63 | 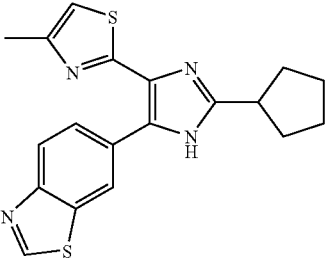 | | 180.5-182.0 | |
| Compound 64 | 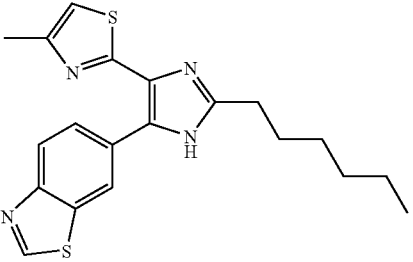 | | 129.0-130.5 | |
| Compound 65 | 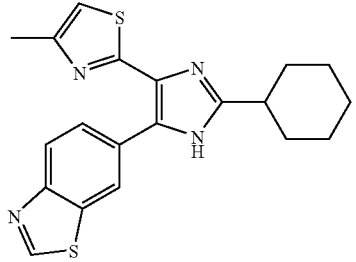 | | 195.0-196.5 | |

TABLE 1-continued

| Compound No. | Structural Formula of Compound | Salt form if applicable | Mp (° C.) | 1H-NMR |
|---|---|---|---|---|
| Compound 66 | | HCl | | (200 MHz, DMSO-d6) δppm: 0.87 (3H, t, J = 7.5 Hz), 2.01 (2H, m), 2.44 (3H, d, J = 0.9 Hz), 2.59 (2H, m), 3.05 (2H, m), (2H, m), 7.35 (1H, d, J = 0.9 Hz), 7.81 (1H, dd, J = 8.6, 1.8 Hz), 8.30 (1H, d, J = 8.6 Hz), 8.59 (1H, d, J = 1.3 Hz), 9.58 (1H, s) |
| Compound 67 | | HCl | | (300 MHz, DMSO-d6) δppm: 0.84 (3H, t, J = 6.8 Hz), 1.23 (1H, m), 1.82 (2H, m), 2.44 (3H, d, J = 0.6 Hz), 2.98 (2H, t, J = 7.6 Hz), 7.35 (1H, d, J = 0.9 Hz), 7.84 (1H, m), 8.29 (1H, d, J = 8.5 Hz), 8.61 (1H, d, J = 1.4 Hz), 9.58 (1H, s) |
| Compound 68 | | | | (300 MHz, DMSO-d6) δppm: 2.40 (3H, d, J = 0.9 Hz), 7.21 (1H, d, J = 0.9 Hz), 7.50 (2H, brs), 7.78 (1H, m), 8.25 (1H, d, J = 8.5 Hz), 8.54 (1H, d, J = 1.4 Hz), 9.54 (1H, s) |
| Compound 69 | | | | (300 MHz, DMSO-d6) δppm: 2.12 (3H, s), 2.33 (3H, s), 7.16 (1H, d, J = 1.1 Hz), 8.10-8.13 (2H, m), 8.83 (1H, brs), 9.43 (1H, s), 11.37 (1H, brs), 12.03 (1H, brs) |
| Compound 70 | | 2HCl | 229.0-233.0 | (300 MHz, DMSO-d6) δppm: 2.37 (3H, d, J = 0.9 Hz), 4.16-4.25 (2H, m), 7.22 (1H, d, J = 0.9 Hz), 8.08 (1H, dd, J = 8.6, 1.8 Hz), 8.18 (1H, d, J = 8.5 Hz), 8.60 (3H, br), 8.90 (1H, d, J = 0.9 Hz), 9.47 (1H, s) |

TABLE 1-continued

| Compound No. | Structural Formula of Compound | Salt form if applicable | Mp (° C.) | 1H-NMR |
|---|---|---|---|---|
| Compound 71 | | | | (300 MHz, COCl3) δppm: 1.49 (9H, s), 2.44 (3H, d, J = 0.9 Hz), 4.43 (2H, d, J = 6.1 Hz), 5.29 (1H, brs), 6.76 (1H, s), 7.86 (1H, dd, J = 8.5, 1.8 Hz), 8.18 (1H, d, J = 8.4 Hz), 8.55 (1H, brs), 9.04 (1H, s) |
| Compound 72 | | | 250.5-255.0 | (300 MHz, CDCl3) δppm: 2.44 (3H, d, J = 0.8 Hz), 5.08 (2H, s), 6.74 (1H, brs), 7.71-7.94 (6H, m), 8.16 (1H, d, J = 8.5 Hz), 9.03 (1H, s) |
| Compound 73 | | | | (300 MHz, DMSO-d6) δppm: 0.88 (3H, t, J = 7.2 Hz), 1.20-1.59 (13H, m), 2.34 (3H, s), 3.29 (2H, brs), 4.46 (2H, brs), 7.14 (1H, s), 8.02-8.18 (2H, m), 8.86 (1H, brs), 9.43 (1H, s), 12.73 (1H, brs) |
| Compound 74 | | 2HCl | | (300 MHz, DMSO-d6) δppm: 0.91 (3H, t, J = 7.4 Hz), 1.31-1.45 (2H, m), 1.62-1.75 (2H, m), 2.38 (3H, d, J = 1.1 Hz), 3.00-3.15 (2H, m), 4.32-4.41 (2H, m), 7.25 (1H, d, J = 0.9 Hz), 8.12 (1H, dd, J = 8.7, 1.8 Hz), 8.19 (1H, dd, J = 8.7, 0.6 Hz), 8.94 (1H, d, J = 1.2 Hz), 9.49 (1H, s), 9.69 (2H, brs) |
| Compound 75 | | | | (300 MHz, DMSO-d6) δppm: 0.86 (3H, t, J = 7.4 Hz), 1.35-1.47 (2H, m), 1.77-1.87 (2H, m), 2.34 (3H, d, J = 0.9 Hz), 2.44-2.71 (6H, m), 6.06 (2H, s), 6.99 (1H, d, J = 8.2 Hz), 7.09 (1H, d, J = 1.1 Hz), 7.46 (1H, dd, J = 8.2, 1.9 Hz), 7.75 (1H, d, J = 1.6 Hz) |

TABLE 1-continued

| Compound No. | Structural Formula of Compound | Salt form if applicable | Mp (° C.) | 1H-NMR |
|---|---|---|---|---|
| Compound 76 | | 2MeSO3H | 118.5-128.5 | |
| Compound 77 | | | 199.5-200.5 | (300 MHz, CDCl3) δppm: 1.76-2.17 (4H, m), 2.45 (3H, d, J = 0.9 Hz), 2.72-2.85 (2H, m), 3.02 (1H, m), 3.20-3.32 (2H, m), 6.68 (1H, brs), 7.85 (1H, dd, J = 8.5, 1.7 Hz), 8.17 (1H, dd, J = 8.5, 0.3 Hz), 8.32 (1H, br), 9.03 (1H, s) |
| Compound 78 | | | | (200 MHz, CDCl3) δppm: 1.47 (9H, s), 1.67-2.17 (4H, m), 2.43 (3H, d, J = 0.9 Hz), 2.76-3.09 (3H, m), 4.13-4.33 (2H, m), 6.68 (1H, s), 7.85 (1H, dd, J = 8.6, 1.5 Hz), 8.17 (1H, d, J = 8.4 Hz), 8.30 (1H, s), 9.02 (1H, s) |
| Compound 79 | | | | (300 MHz, CDCl3) δppm: 1.63-2.23 (8H, m), 2.43 (3H, d, J = 0.9 Hz), 2.94 (1H, m), 3.96-4.00 (4H, m), 6.67 (1H, brs), 7.86 (1H, dd, J = 8.4, 1.7 Hz), 8.17 (1H, d, J = 8.4 Hz), 8.31 (1H, brs), 9.03 (1H, s), 10.01 (1H, brs) |
| Compound 80 | | | 207.5-208.5 | |

TABLE 1-continued

| Compound No. | Structural Formula of Compound | Salt form if applicable | Mp (° C.) | 1H-NMR |
|---|---|---|---|---|
| Compound 81 | | HCl | | (300 MHz, DMSO-d6), δppm: 0.82-0.96 (3H, m), 1.25-1.49 (48, m), 1.70-2.09 (2H, m), 2.33-2.48 (3H, m), 2.90-3.29 (2H, m), 3.51 (1H, m), 7.37 (1H, s), 7.84 (1H, dd, J = 8.5, 1.8 Hz), 8.29 (1H, d, J = 8.5 Hz), 8.61 (1H, d, J = 1.7 Hz), 9.58 (1H, s) |
| Compound 82 | | | 222.0-223.0 | (300 MHz, DMSO-d6) δppm: 2.34 (3H, d, J = 0.8 Hz), 4.53 (2H, s), 5.50 (1H, brs), 7.15 (1H, d, J = 0.9 Hz), 8.05-8.18 (2H, m), 8.87 (1H, brs), 9.43 (1H, s), 12.80 (1H, br) |
| Compound 83 | | | 204.5-205.0 | |
| Compound 84 | | | | (300 MHz, DMSO-d6) δppm: 1.95-2.05 (2H, m), 2.34 (3H, d, J = 0.6 Hz), 2.74-2.81 (2H, m), 3.50 (2H, t, J = 6.3 Hz), 3.72 (3H, s), 4.41 (2H, s), 6.85-6.91 (2H, m), 7.13 (1H, d, J = 1.1 Hz), 7.23-7.29 (2H, m), 8.10-8.15 (2H, m), 8.90 (1H, s), 9.42 (1H, s), 12.51 (1H, s) |
| Compound 85 | | | | (300 MHz, CDCl3) δppm: 2.21 (2H, t, J = 6.0 Hz), 2.38 (3H, s), 2.43 (3H, d, J = 0.9 Hz), 2.95 (2H, t, J = 7.1 Hz), 4.12-4.17 (2H, m), 6.75 (1H, d, J = 1.1 Hz), 7.27-7.31 (2H, m), 7.74-7.79 (2H, m), 7.84 (1H, dd, J = 8.5, 1.7 Hz), 8.13 (1H, dd, J = 8.5, 0.8 Hz), 8.43 (1H, d, J = 1.4 Hz), 9.03 (1H, s) |

TABLE 1-continued

| Compound No. | Structural Formula of Compound | Salt form if applicable | Mp (° C.) | 1H-NMR |
|---|---|---|---|---|
| Compound 86 | | | | (300 MHz, DMSO-d6) δppm: 1.86-1.97 (2H, m), 2.37 (38, d, J = 0.9 Hz), 2.84 (2H, t, J = 7.6 Hz), 3.51 (2H, m, J = 6.2 Hz), 7.20 (1H, d, J = 0.9 Hz), 8.00 (1H, m), 8.18 (1H, dd, J = 8.5, 0.3 Hz), 8.77 (1H, s), 9.47 (1H, s) |
| Compound 87 | | HCl | | (300 MHz, DMSO-d6) δppm: 1.58 (2H, m), 1.88 (2H, m), 2.44 (3H, d, J = 0.9 Hz), 3.03 (2H, t, J = 7.6 Hz), 3.24 (3H, s), 3.37 (2H, t, J = 6.2 Hz), 7.36 (1H, d, J = 1.1 Hz), 7.84 (1H, dd, J = 8.5, 1.7 Hz), 8.29 (1H, d, J = 8.5 Hz), 8.61 (1H, d, J = 1.2 Hz), 9.58 (1H, s) |
| Compound 88 | | | 257.0-259.5 | (300 MHz, CDCl3) δppm: 2.28 (38, d, J = 0.9 Hz), 3.65 (3H, s), 5.06 (2H, s), 6.60 (1H, d, J = 0.9 Hz), 7.56 (1H, dd, J = 8.4, 1.7 Hz), 7.72-7.93 (4H, m), 8.11 (1H, d, J = 1.6 Hz), 8.23 (1H, d, J = 8.5 Hz), 9.09 (1H, s) |
| Compound 89 | | | 183.0-184.5 | (300 MHz, CDCl3) δppm: 2.36 (38, d, J = 0.9 Hz), 3.52 (3H, s), 4.06 (2H, s), 6.61 (1H, d, J = 0.9 Hz), 7.56 (1H, dd, J = 8.5, 1.6 Hz), 8.10 (1H, dd, J = 1.6, 0.5 Hz), 8.26 (1H, dd, J = 8.4, 0.5 Hz), 9.10 (1H, s) |
| Compound 90 | | | 212.5-213.5 | (300 MHz, DMSO-d6) δppm: 0.88 (3H, t, J = 7.4 Hz), 1.47-1.63 (2H, m), 2.09-2.18 (5H, m), 3.47 (3H, s), 4.46 (2H, d, J = 5.8 Hz), 7.04 (1H, d, J = 0.9 Hz), 7.64 (1H, dd, J = 8.5, 1.7 Hz), 8.17 (1H, dd, J = 8.5, 0.5 Hz), 8.34 (1H, dd, J = 1.7, 0.5 Hz), 8.46 (1H, brt, J = 5.6 Hz), 9.49 (1H, s) |

TABLE 1-continued

| Compound No. | Structural Formula of Compound | Salt form if applicable | Mp (° C.) | 1H-NMR |
| --- | --- | --- | --- | --- |
| Compound 91 | | | | (300 MHz, CDCl3) δppm: 2.31 and 2.46 (3H, 2d, J = 0.9 Hz), 4.96, 4.97, 5.27 and 5.61 (4H, 4s), 6.61-8.29 (13H, m), 8.94 and 9.04 (1H, 2s) |
| Compound 92 | | | | (300 MHz, CDCl3) δppm: 2.37 and 2.50 (3H, 2d, J = 0.9 Hz), 3.90 and 3.93 (2H, 2s), 5.12 and 5.50 (2H, 2s), 6.60-8.27 (9H, m), 8.97 and 9.07 (1H, 2s) |
| Compound 93 | | | | (300 MHz, CDCl3) δppm: 0.88-0.98 (3H, m), 1.54-1.73 (2H, m), 2.08-2.20 (2H, m), 2.39 and 2.50 (3H, 2d, J = 0.9 Hz), 4.49-4.57 (2H, m), 5.15 and 5.51 (2H, 2s), 6.29-8.26 (10H, m), 8.98 and 9.07 (1H, 2s) |
| Compound 94 | | | | (300 MHz, CDCl3) δppm: 0.71-0.94 (3H, m), 1.34-1.98 (4H, m), 2.38 and 2.46 (3H, 2d, J = 1.1 Hz), 2.90-2.98 (3H, m), 4.83 (2H, s), 5.22 and 5.55 (2H, 2s), 6.60-8.29 (9H, m), 8.97 and 9.05 (1H, 2s) |
| Compound 95 | | | 175.0-175.5 | (300 MHz, DMSO-d6) δppm: 0.87-0.98 (3H, m), 1.48-1.67 (2H, m), 2.26-2.44 (5H, m), 2.90 and 3.07 (3H, 2s), 4.63 (2H, s), 7.15 (1H, m), 8.03-8.19 (2H, m), 8.84 (1H, m), 9.44 (1H, d, J = 1.2 Hz), 12.67 and 12.84 (1H, 2br) |

TABLE 1-continued

| Compound No. | Structural Formula of Compound | Salt form if applicable | Mp (° C.) | 1H-NMR |
|---|---|---|---|---|
| Compound 96 | | | 209.5-210.5 | (300 MHz, DMSO-d6) δppm: 1.90-2.05 (2H, 2.25-2.33 (2H, m), 2.33 (3H, s), 3.43 (2H, t, J = 7.2 Hz), 4.50 (2H, s), 7.15 (1H, d, J = 1.1 Hz), 8.08 (1H, brs), 8.13 (1H, d, J = 8.4 Hz), 8.81 (1H, brs), 9.43 (1H, s), 12.82 (1H, br) |
| Compound 97 | | | | (200 MHz, CDCl3) δppm: 2.43 (3H, d, J = 0.9 Hz), 5.03 (2H, s), 6.00 (2H, s), 6.71 (1H, brs), 6.85 (1H, d, J = 8.1 Hz), 7.16-7.40 (2H, m), 7.72-7.91 (4H, m) |
| Compound 98 | | | | (200 MHz, DMSO-d6) δppm: 2.32 (3H, s), 4.88 (2H, s), 7.11 (1H, s), 7.25 (2H, t, J = 8.9 Hz), 7.83-7.97 (6H, m) |
| Compound 99 | | | | (300 MHz, DMSO-d6) δppm: 2.30 (3H, d, J = 0.8 Hz), 4.86 (2H, s), 6.79 (2H, d, J = 8.7 Hz), 7.05 (1H, d, J = 0.8 Hz), 7.71 (2H, d, J = 8.5 Hz), 7.83-7.97 (4H, m), 9.64 (1H, s), 12.43 (1H, s) |
| Compound 100 | | | | (300 MHz, DMSO-d6) δppm: 2.33 (3H, d, J = 0.8 Hz), 3.84 (2H, s), 6.82 (2H, d, J = 8.9 Hz), 7.08 (1H, d, J = 1.1 Hz), 7.75-7.91 (2H, m) |

TABLE 1-continued

| Compound No. | Structural Formula of Compound | Salt form if applicable | Mp (° C.) | 1H-NMR |
|---|---|---|---|---|
| Compound 101 | | | 135.5-136.5 | |
| Compound 102 | | | | (200 MHz, CDCl3) δppm: 2.38 (3H, s), 3.91 (3H, s), 5.03 (2H, s), 5.19 (2H, s), 6.71 (1H, br), 6.91 (1H, d, J = 8.0 Hz), 7.15-7.50 (7H, m), 7.68-7.80 (2H, m), 7.81-7.93 (2H, m) |
| Compound 103 | | | | (200 MHz, CDCl3) δppm: 2.42 (3H, d, J = 0.9 Hz), 3.90 (3H, s), 4.03 (2H, 3), 5.18 (2H, s), 6.69 (1H, d, J = 0.9 Hz), 6.91 (1H, d, J = 8.4 Hz), 7.15-7.48 (6H, m), 7.71 (1H, s) |
| Compound 104 | | | 176.0-177.0 | (300 MHz, CDCl3) δppm: 0.93 (3H, t, J = 7.4 Hz), 1.66 (2H, qt, J = 7.5 Hz), 2.21 (2H, t, J = 7.5 Hz), 2.43 (3H, d, J = 1.1 Hz), 3.91 (3H, s), 4.47 (2H, d, J = 5.9 Hz), 5.19 (2H, s), 6.67 (1H, t, J = 6.1 Hz), 6.73 (1H, d, J = 1.1 Hz), 6.92 (1H, d, J = 8.4 Hz), 7.13-7.48 (6H, m), 7.85 (1H, s) |

TABLE 1-continued

| Compound No. | Structural Formula of Compound | Salt form if applicable | Mp (° C.) | 1H-NMR |
|---|---|---|---|---|
| Compound 105 | | | 190.0-191.0 | (300 MHz, DMSO-d6) δppm: 0.89 (3H, t, J = 7.4 Hz), 1.47-1.64 (2H, m), 2.14 (2H, t, J = 7.5 Hz), 2.34 (3H, s), 4.36 (2H, d, J = 5.6 Hz), 7.15 (1H, d, J = 0.9 Hz), 8.08 (1H, s), 8.14 (1H, d, J = 8.5 Hz), 8.34 (1H, t, J = 5.1 Hz), 8.85 (1H, s), 9.43 (1H, s), 12.72 (1H, s) |
| Compound 106 | | | | (300 MHz, CDCl3) δppm: 0.79 (2H, m), 1.01 (2H, m), 1.44 (1H, m), 2.43 (3H, d, J = 0.8 Hz), 4.55 (2H, d, J = 5.9 Hz), 6.75 (1H, d, J = 0.8 Hz), 6.99 (1H, m), 7.84 (1H, dd, J = 8.5, 1.7 Hz), 8.15 (1H, d, J = 8.4 Hz), 8.49 (1H, brs), 9.03 (1H, s) |
| Compound 107 | | | 160.0-160.5 | |
| Compound 108 | | | 199.0-200.0 | |
| Compound 109 | | | 229.0-229.5 | |

TABLE 1-continued

| Compound No. | Structural Formula of Compound | Salt form if applicable | Mp (° C.) | 1H-NMR |
|---|---|---|---|---|
| Compound 110 | | | 172.5-173.5 | |
| Compound 111 | | | 212.5-213.5 | |
| Compound 112 | | | 156.5-161.0 | |
| Compound 113 | | | | (300 MHz, CDCl3) δppm: 1.21-1.90 (10H, m), 2.17 (1H, m), 2.44 (3H, d, J = 0.9 Hz), 4.53 (2H, d, J = 5.9 Hz), 6.54 (1H, t, J = 5.6 Hz), 6.76 (1H, d, J = 0.9 Hz), 7.86 (1H, dd, J = 8.5, 1.7 Hz), 8.16 (1H, d, J = 8.4 Hz), 8.52 (1H, brs), 9.03 (1H, s) |
| Compound 114 | | | 211.5-212.5 | |

TABLE 1-continued

| Compound No. | Structural Formula of Compound | Salt form if applicable | Mp (° C.) | 1H-NMR |
|---|---|---|---|---|
| Compound 115 | | | 150.0-150.5 | |
| Compound 116 | | | 200.5-205.5 | |
| Compound 117 | | | 204.0-205.5 | |
| Compound 118 | | | 200.5-203.5 | |
| Compound 119 | | | | (200 MHz, CDCl3) δppm: 1.36 (9H, s), 2.43 (3H, d, J = 0.9 Hz), 2.88 (3H, s), 3.90 (2H, s), 4.60 (2H, d, J = 6.2 Hz), 6.75 (1H, d, J = 0.9 Hz), 7.10 (1H, t, J = 5.7 Hz), 7.87 (1H, dd, J = 8.6, 1.5 Hz), 8.14 (1H, d, J = 8.4 Hz), 8.51 (1H, s), 9.02 (1H, s) |

TABLE 1-continued

| Compound No. | Structural Formula of Compound | Salt form if applicable | Mp (° C.) | 1H-NMR |
|---|---|---|---|---|
| Compound 120 | | | 214.5-215.0 | |
| Compound 121 | | | | (200 MHz, CDCl3) δppm 1.36 (9H, s), 2.42 (3H, d, J = 0.9 Hz), 3.85 (2H, d, J = 5.7 Hz), 4.59 (2H, d, J = 5.7 Hz), 5.55 (1H, s), 6.74 (1H, d, J = 0.9 Hz), 7.57 (1H, s), 7.81 (1H, dd, J = 8.4, 1.8 Hz), 8.12 (1H, d, J = 8.8 Hz), 8.41 (1H, d, J = 1.3 Hz), 9.02 (1H, s) |
| Compound 122 | | | 215.0-218.5 | |
| Compound 123 | | | 134.0-135.5 | |
| Compound 124 | | | 223.5-224.0 | |

TABLE 1-continued

| Compound No. | Structural Formula of Compound | Salt form if applicable | Mp (° C.) | 1H-NMR |
|---|---|---|---|---|
| Compound 125 | | | 186.5-190.0 | |
| Compound 126 | | | 193.0-194.0 | |
| Compound 127 | | | 154.5-155.5 | |
| Compound 128 | | | 174.0-175.0 | |
| Compound 129 | | | 197.0-197.5 | |

TABLE 1-continued

| Compound No. | Structural Formula of Compound | Salt form if applicable | Mp (° C.) | 1H-NMR |
|---|---|---|---|---|
| Compound 130 | | | 185.0-185.5 | |
| Compound 131 | | | 185.0-185.5 | |
| Compound 132 | | | | (200 MHz. CDCl3) δppm: 2.42 (3H, d, J = 0.7 Hz), 3.22 (2H, t, J = 8.8 Hz), 4.15 (2H, t, J = 6.8 Hz), 6.00 (2H, s), 6.69 (1H, s), 6.85 (1H, d, J = 8.1 Hz), 7.19-7.25 (2H, m), 7.69-7.87 (4H, m) |
| Compound 133 | | | | (200 MHz, CDCl3) δppm: 1.16 (3H, t, J = 7.5 Hz), 2.26 (2H, q, J = 7.5 Hz), 2.45 (3H, d, J = 0.9 Hz), 3.03-3.14 (2H, m), (1H, d, J = 1.3 Hz), 7.94 (1H, dd, J = 8.4, 1.8 Hz), 8.18 (1H, d, J = 8.4 Hz), 8.60 (1H, br), 9.03 (1H, s) |
| Compound 134 | | | | (200 MHz, CDCl3) δppm: 1.80-2.01 (2H, m), 2.10 (3H, s), 2.46 (3H, d, J = 1.3 Hz), 2.80-2.93 (2H, m), 3.35-3.51 (2H, m), 5.96 (114, brs), 6.76 (1H, s), 8.02 (1H, d, J = 8.8 Hz), 8.17 (1H, d, J = 8.8 Hz), 9.01 (1H, s) |

TABLE 1-continued

| Compound No. | Structural Formula of Compound | Salt form if applicable | Mp (° C.) | 1H-NMR |
|---|---|---|---|---|
| Compound 135 | | | | (300 MHz, DMSO-d6) δppm: 2.05-2.10 (2H, m), 2.32 (3H, d, J = 0.8 Hz), 2.70 (2H, t, J = 7.7 Hz), 3.70 (2H, t, J = 6.8 Hz), 6.06 (2H, s), 6.98 (1H, d, J = 8.2 Hz), 7.07 (1H, d, J = 1.1 Hz), 7.46 (1H, dd, J = 8.2, 1.9 Hz), 7.77-7.84 (5H, m), 12.19 (1H, s) |
| Compound 136 | | | | (300 MHz, CDCl3) δppm: 1.81-1.83 (4H, m), 2.43 (3H, d, J = 0.9 Hz), 2.87 (2H, m), 3.78 (2H, t, J = 6.8 Hz), 6.01 (2H, s), 6.69 (1H, s), 6.87 (1H, d, J = 8.1 Hz), 7.21-7.24 (2H, m), 7.69-7.86 (4H, m) |
| Compound 137 | | | | (300 MHz, DMSO-d6) δppm: 1.35 (3H, t, J = 7.1 Hz), 2.34 (3H, s), 4.37 (2H, q, J = 7.1 Hz), 6.09 (2H, s), 7.00 (1H, d, J = 8.1 Hz), 7.22 (1H, s), 7.47 (1H, d, J = 8.4 Hz), 7.58 (1H, m), 13.73 (1H, brs) |
| Compound 138 | | | 238.5-239.0 | (300 MHz, DMSO-d6) δppm: 1.37 (3H, t, J = 7.1 Hz), 2.31 (3H, s), 4.40 (2H, q, J = 6.8 Hz), 7.24 (1H, s), 8.03 (1H, d, J = 8.7 Hz), 8.14 (1H, d, J = 8.5 Hz), 8.74 (1H, s), 9.48 (1H, s), 14.02 (1H, s) |
| Compound 139 | | | | (200 MHz, DMSO-d6) δppm: 2.32 (3H, s), 7.13 (1H, d, J = 0.9 Hz), 8.00-8.18 (2H, m), 8.82 (1H, d, J = 1.3 Hz), 9.40 (1H, s) |

TABLE 1-continued

| Compound No. | Structural Formula of Compound | Salt form if applicable | Mp (° C.) | 1H-NMR |
|---|---|---|---|---|
| Compound 140 | | | 209.5-212.5 | |
| Compound 141 | | | | (300 MHz, CDCl3) δppm: 2.43 (3H, d, J = 0.9 Hz), 2.79-2.86 (2H, m), 3.05-3.11 (2H, m), 3.74 (3H, s), 6.00 (2H, s), 6.70 (1H, brs), 6.86 (1H, d, J = 8.1 Hz), 7.17-7.40 (2H, m) |
| Compound 142 | | | 168.5-170.5 | |
| Compound 143 | | | | (300 MHz, DMSO-d6) δppm: 2.38 (3H, s), 2.83 (2H, t, J = 7.3 Hz), 3.04 (2H, t, J = 7.3 Hz), 7.22 (1H, s), 7.97 (1H, m), 8.21 (1H, d, J = 8.7 Hz), 8.75 (1H, s), 9.49 (1H, s) |
| Compound 144 | | | 208.0-209.0 | |

TABLE 1-continued

| Compound No. | Structural Formula of Compound | Salt form if applicable | Mp (° C.) | 1H-NMR |
|---|---|---|---|---|
| Compound 145 | | | 217.5-218.0 | |
| Compound 146 | | | 196.5-197.0 | |
| Compound 147 | | | 201.5-202.0 | |
| Compound 148 | | | 179.0-180.0 | |
| Compound 149 | | | 163.5-164.0 | |

TABLE 1-continued

| Compound No. | Structural Formula of Compound | Salt form if applicable | Mp (° C.) | 1H-NMR |
|---|---|---|---|---|
| Compound 150 | | | 78.5-82.5 | |
| Compound 151 | | | 114.0-119.0 | |
| Compound 152 | | | 171.0-173.0 | |
| Compound 153 | | | 188.0-189.0 | |
| Compound 154 | | | | (300 MHz, DMSO-d6) δppm: 1.32-2.08 (6H, m), 2.14 (3H, s), 2.34 (3H, s), 2.69-2.99 (8H, m), 3.66 (1H, m), 4.25 (1H, m), 7.13 (1H, s), 8.06-8.17 (2H, m), 8.91 (1H, s), 9.43 (1H, s), 12.51 (1H, s) |

TABLE 1-continued

| Compound No. | Structural Formula of Compound | Salt form if applicable | Mp (° C.) | 1H-NMR |
|---|---|---|---|---|
| Compound 155 | | | 201.0-201.5 | |
| Compound 156 | | | | (300 MHz, CDCl3) δppm: 2.23 and 2.25 (6H, 2s), 2.44 (5H, m), 2.80 and 2.86 (2H, m), 3.00 and 3.03 (3H, 2s), 3.18 (2H, m), 3.39 and 3.55 (2H, m), 6.70 (1H, m), 7.90 (1H, m), 8.15 (1H, d, J = 8.5 Hz), 8.33 and 8.75 (1H, m), 9.01 (1H, s), 10.95 (1H, m) |
| Compound 157 | | | 164.5-166.0 | |
| Compound 158 | | | 169.5-172.0 | |
| Compound 159 | | | | (300 MHz, DMSO-d6) δppm: 2.34 (9H, m), 2.59 (2H, m), 2.93 (2H, m), 3.19 (2H, m), brs), 3.53 (4H, m), 7.14 (1H, d, J = 1.1 Hz), 7.89 (1H, m), 8.13 (2H, m), 8.92 (1H, s), 9.43 (1H, s), 12.54 (1H, s) |

TABLE 1-continued

| Compound No. | Structural Formula of Compound | Salt form if applicable | Mp (° C.) | 1H-NMR |
|---|---|---|---|---|
| Compound 160 | | | | (200 MHz, CDCl3) δppm: 2.44 (3H, s), 2.84 (2H, s), 3.01 and 3.07 (3H, 2s), 3.17 (2H, m), 3.30 and 3.32 (3H, 2s), 3.50-3.65 (4H, m), 6.74 (1H, s), 7.90 (1H, m), 8.14 (1H, d, J = 8.6 Hz), 8.61 (1H, brs), 9.01 (1H, s) |
| Compound 161 | | | 216.5-218.0 | |
| Compound 162 | | | | (300 MHz, DMSO-d6) δppm: 2.34 (3H, s), 2.83 (2H, m), 2.95 (2H, m), 3.46-3.58 (8H, m), 7.13 (1H, d, J = 0.9 Hz), 8.10 (1H, m), 8.12 (1H, m), 8.88 (1H, brs), 9.43 (1H, s), 12.55 (1H, s) |
| Compound 163 | | | 199.0-198.5 | |
| Compound 164 | | | 144.5-145.0 | |

TABLE 1-continued

| Compound No. | Structural Formula of Compound | Salt form if applicable | Mp (° C.) | 1H-NMR |
|---|---|---|---|---|
| Compound 165 | | | | (300 MHz, CDCl3) δppm: 2.09-2.14 (2H, m), 2.43 (3H, d, J = 0.9 Hz), 2.43-2.49 (2H, m), 2.84 (2H, t, J = 7.5 Hz), 3.09 (3H, s), 6.01 (2H, s), 6.69 (1H, s), 6.87 (1H, d, J = 8.1 Hz), 7.19 (1H, d, J = 8.1 Hz), 7.26 (1H, m) |
| Compound 166 | | HCl | | (200 MHz, CDCl3) δppm: 1.99-2.18 (2H, m), 2.31 (2H, t, J = 6.8 Hz), 2.43 (3H, d, J = 0.9 Hz), 2.77-2.97 (5H, m), 6.22 (1H, m), 6.74 (1H, d, J = 0.9 Hz), 7.91 (1H, dd, J = 8.8, 1.8 Hz), 8.13 (1H, d, J = 8.8 Hz), 8.56 (1H, brs), 9.01 (1H, s) |
| Compound 167 | | | 158.0-159.0 | |
| Compound 168 | | | | (300 MHz, CDCl3) δppm: 1.70-1.91 (4H, m), 2.40 (2H, m), 2.43 (3H, d, J = 0.9 Hz), 2.84 (2H, t, J = 7.1 Hz), 6.72 (1H, brs), 7.90 (1H, m), 8.16 (1H, d, J = 8.5 Hz), 9.02 (1H, s) |
| Compound 169 | | | | (300 MHz, DMSO-d6) δppm: 1.52-1.65 (2H, m), 1.76-1.89 (2H, m), 2.30 (2H, t, J = 7.3 Hz), 2.43 (3H, d, J = 0.9 Hz), 2.95 (2H, t, J = 7.1 Hz), 7.31 (1H, d, J = 0.9 Hz), 7.88 (1H, dd, J = 8.6, 1.5 Hz), 8.27 (1H, d, J = 8.4 Hz), 8.33 (1H, s), 8.65 (1H, s), 9.56 (1H, s) |

TABLE 1-continued

| Compound No. | Structural Formula of Compound | Salt form if applicable | Mp (° C.) | 1H-NMR |
|---|---|---|---|---|
| Compound 170 | | | | (300 MHz, DMSO-d6) δppm: 1.52-1.79 (4H, m), 2.11 (2H, t, J = 7.3 Hz), 2.34 (3H, d, J = 0.9 Hz), 2.69 (2H, t, J = 7.5 Hz), 6.72 (1H, brs), 7.13 (1H, d, J = 1.1 Hz), 7.27 (1H, brs), 8.12 (2H, brs), 8.90 (1H, brs), 9.42 (1H, s), 12.51 (1H, brs) |
| Compound 171 | | | | (300 MHz, DMSO-d6) δppm: 0.82 (3H, t, J = 7.4 Hz), 1.39 (2H, m), 1.55-1.73 (4H, m), 2.12 (2H, t, J = 7.2 Hz), 2.33 (3H, s), 2.69 (2H, t, J = 7.5 Hz), 2.99 (2H, m), 7.13 (1H, s), 7.77 (1H, brt, J = 5.6 Hz), 8.13 (2H, m), 8.90 (1H, brs), 9.43 (1H, s), 12.49 (1H, brs) |
| Compound 172 | | HCl | 105.0-117.5 | |
| Compound 173 | | | 140.0-140.5 | |
| Compound 174 | | | | (300 MHz, DMSO-d6) δppm: 2.35 (3H, d, J = 0.9 Hz), 4.30 (2H, d, J = 5.6 Hz), 5.69 (2H, s), 6.47 (1H, t, J = 5.4 Hz), 7.16 (1H, d, J = 1.1 Hz), 8.05 (1H, m), 8.15 (1H, m), 8.82 (1H, s), 9.44 (1H, s) |

TABLE 1-continued

| Compound No. | Structural Formula of Compound | Salt form if applicable | Mp (°C.) | 1H-NMR |
|---|---|---|---|---|
| Compound 175 | | | 189.0-191.0 | |
| Compound 176 | | | | (200 MHz, CDCl3) δppm: 2.43 (3H, d, J = 0.9 Hz), 2.94 (6H, s), 4.51 (2H, d, J = 5.9 Hz), 5.39 (1H, m), 6.75 (1H, d, J = 1.1 Hz), 7.88 (1H, dd, J = 8.6, 1.8 Hz), 8.15 (1H, d, J = 8.6 Hz), 8.54 (1H, d, J = 1.5 Hz), 9.02 (1H, s) |
| Compound 177 | | | 179.5-182.0 | |
| Compound 178 | | | 178.5-180.0 | |
| Compound 179 | | | 190.5-191.5 | |

TABLE 1-continued

| Compound No. | Structural Formula of Compound | Salt form if applicable | Mp (° C.) | 1H-NMR |
|---|---|---|---|---|
| Compound 180 | | | | (300 MHz, CDCl3) δppm: 1.31 (9H, s), 2.41 (3H, d, J = 0.8 Hz), 4.43 (2H, brs), 4.93 (1H, brs), 6.01 (1H, m), 6.74 (1H, d, J = 0.9 Hz), 7.80 (1H, dd, J = 8.5, 1.9 Hz), 8.11 (1H, d, J = 8.4 Hz), 8.46 (1H, d, J = 1.5 Hz), 9.02 (1H, s) |
| Compound 181 | | | 222.5-223.0 | |
| Compound 182 | | | 199.0-201.0 | |
| Compound 183 | | | 185.5-188.0 | |
| Compound 184 | | | | (300 MHz, CDCl3) δppm: 1.05-1.84 (10H, m), 2.39 (3H, d, J = 0.8 Hz), 3.47 (1H, m), 4.60 (2H, brs), 5.39 (1H, m), 6.75 (1H, d, J = 0.9 Hz), 6.84 (1H, m), 7.77 (1H, m), 8.13 (1H, d, J = 8.5 Hz), 8.37 (1H, d, J = 1.7 Hz), 9.05 (1H, s) |

TABLE 1-continued

| Compound No. | Structural Formula of Compound | Salt form if applicable | Mp (° C.) | 1H-NMR |
|---|---|---|---|---|
| Compound 185 | | | 205.5-206.0 | |
| Compound 186 | | | 207.0-209.0 | |
| Compound 187 | | | 183.0-184.0 | |
| Compound 188 | | | 202.0-204.0 (dec.) | |
| Compound 189 | | | 200.5-201.0 | |

TABLE 1-continued

| Compound No. | Structural Formula of Compound | Salt form if applicable | Mp (° C.) | 1H-NMR |
|---|---|---|---|---|
| Compound 190 | | | 180.0-181.0 | |
| Compound 191 | | | | (300 MHz, CDCl3) δppm: 2.44 (3H, d, J = 0.9 Hz), 2.50 (1H, t, J = 2.5 Hz), 4.50 (2H, d, J = 6.1 Hz), 4.74 (2H, d, J = 2.5 Hz), 5.79 (1H, t, J = 6.1 Hz), 6.75 (1H, s), 7.85 (1H, dd, J = 8.5, 1.7 Hz), 8.16 (1H, d, J = 8.5 Hz), 9.04 (1H, s) |
| Compound 192 | | HCl | 174.0-175.0 | |
| Compound 193 | | | 161.0-162.0 | |
| Compound 194 | | | 142.5-144.0 | |

TABLE 1-continued

| Compound No. | Structural Formula of Compound | Salt form if applicable | Mp (° C.) | 1H-NMR |
| --- | --- | --- | --- | --- |
| Compound 195 | | | 177.5-178.5 | |
| Compound 196 | | | 170.5-171.5 | |
| Compound 197 | | | 232.0-233.0 | (300 MHz, DMSO-d6) δppm: 2.34 (3H, s), 3.60-3.68 (2H, m), 4.28-4.36 (2H, m), (2H, s), 7.16 (1H, d, J =0.9 Hz), 8.08 (1H, br), 8.14 (1H, d, J = 8.4 Hz), 8.83 (1H, br), 9.44 (1H, s), 12.93 (1H, br) |
| Compound 198 | | | 144.0-145.0 | (300 MHz, DMSO-d6) δppm: 1.04 (3H, t, J = 7.2 Hz), 2.34 (3H, s), 2.99-3.12 (2H, m), 5.04 (2H, s), 7.18 (1H, d, J = 0.8 Hz), 7.34 (1H, brt, J = 5.7 Hz), 8.03-8.20 (2H, m), 8.90 (1H, brs), 9.45 (1H, s), 13.06 (1H, brs) |
| Compound 199 | | | 181.5-182.0 | |

TABLE 1-continued

| Compound No. | Structural Formula of Compound | Salt form if applicable | Mp (° C.) | 1H-NMR |
|---|---|---|---|---|
| Compound 200 | | | | (300 MHz, CDCl3) δppm: 1.07 (3H, t, J = 7.5 Hz), 1.89 (2H, m), 2.44 (3H, d, J = 0.9 Hz), 3.08 (2H, m), 4.44 (2H, d, J = 6.2 Hz), 5.47 (1H, m), 6.76 (1H, s), 7.83 (1H, m), 8.16 (1H, d, J = 8.5 Hz), 8.45 (1H, brs), 9.04 (1H, s) |
| Compound 201 | | | 145.0-146.0 | (300 MHz, CDCl3) δppm: 0.93 (3H, t, J = 7.4 Hz), 1.58-1.71 (2H, m), 2.44 (3H, d, J = 0.9 Hz), 2.44-2.50 (2H, m), 2.95-3.11 (4H, m), 6.72 (1H, d, J = 0.9 Hz), 7.86 (1H, dd, J = 8.5, 1.8 Hz), 8.16 (1H, dd, J = 8.5, 0.6 Hz), 8.48 (1H, br), 9.03 (1H, s) |
| Compound 202 | | | 248.0-251.0 (dec.) | |
| Compound 203 | | | 131.5-132.5 | |
| Compound 204 | | | 134.5-135.5 | (300 MHz, CDCl3) δppm: 2.51 (3H, d, J = 0.8 Hz), 7.45 (1H, d, J = 0.8 Hz), 8.16 (1H, dd, J = 8.5, 1.7 Hz), 8.26 (1H, dd, J = 8.5, 0.6 Hz), 8.64 (1H, dd, J = 1.7, 0.6 Hz), 9.23 (1H, s) |
| Compound 205 | | | | (300 MHz, CDCl3) δppm: 2.53 (3H, d, J = 0.8 Hz), 6.77-6.84 (2H, m), 7.43 (1H, d, J = 0.8 Hz), 7.80-7.87 (2H, m) |

TABLE 1-continued

| Compound No. | Structural Formula of Compound | Salt form if applicable | Mp (° C.) | 1H-NMR |
|---|---|---|---|---|
| Compound 206 | | | 75.0-77.0 | |
| Compound 207 | | | | (300 MHz, CDCl3) δppm; 6.09 (2H, s), 6.89 (1H, d, J = 8.5 Hz), 7.51 (1H, d, J = 1.7 Hz), 7.51 (1H, dd, J = 8.5, 1.7 Hz), 7.83 (1H, d, J = 3.0 Hz), 8.11 (1H, d, J = 3.0 Hz) |
| Compound 208 | | | | (300 MHz, CDCl3) δppm: 6.11 (2H, s), 6.90 (1H, d, J = 8.7 Hz), 7.47-7.54 (2H, m), 7.72 (1H, s) |
| Compound 209 | | | | (300 MHz, CDCl3) δppm: 1.28 (3H, t, J = 7.6 Hz), 2.87 (2H, qd, J = 7.6, 0.8 Hz), 6.09 (2H, s), 6.88 (1H, d, J = 8.7 Hz), 7.41 (1H, t, J = 0.8 Hz), 7.49-7.53 (2H, m) |
| Compound 210 | | | | (200 MHz, CDCl3) δppm: 2.76 (3H, s), 6.08 (2H, s), 6.88 (1H, d, J = 8.1 Hz), 7.50-7.57 (2H, m), 8.23 (1H, s) |

TABLE 1-continued

| Compound No. | Structural Formula of Compound | Salt form if applicable | Mp (° C.) | 1H-NMR |
|---|---|---|---|---|
| Compound 211 | | | | (300 MHz, CDCl3) δppm: 2.69 (3H, s) 6.11 (2H, s) 6.90 (1H, dd, J = 8.1, 0.5 Hz), 7.50-7.58 (2H, m), 8.65 (1H, s) |
| Compound 212 | | | | (300 MHz, CDCl3) δppm: 1.65 (3H, d, J = 6.5 Hz), 2.71 (1H, d, J = 4.8 Hz), 5.19 (1H, m), 6.09 (2H, s), 6.88 (1H, d, J = 8.1 Hz), 7.50 (1H, d, J = 1.7 Hz), 7.54 dd, J = 8.2, Hz), 8.33 (1H, s) |
| Compound 213 | | | | (300 MHz, CDCl3) δppm 2.54 (3H, d, J = 0.9 Hz), 5.95-5.99 (2H, m), 6.75 (1H, d, J = 8.1 Hz), 6.78 (1H, s), 7.09 (1H, dd, J = 7.9, 1.9 Hz), 7.21 (1H, d, J = 1.9 Hz), 7.32 (1H, d, J = 0.9 Hz) |
| Compound 214 | | | | (300 MHz, CDCl3) δppm: 2.54 (3H, d, J = 0.9 Hz), 3.80 (3H, s), 6.82 (1H, s), 6.88 (2H, dd, J = 8.9, 2.2 Hz), 7.30 (1H, d, J = 0.9 Hz), 7.59 (2H, dd, J = 8.7, 2.2 Hz) |
| Compound 215 | | | | (300 MHz, CDCl3) δppm: 2.55 (3H, d, J = 0.9 Hz), 6.99 (1H, s), 7.34 (1H, q, J = 0.8 Hz), 7.81 (1H, dd, J = 8.7, 2.0 Hz), 8.12 (1H, d, J = 8.5 Hz), 8.30 (1H, d, J = 1.7 Hz), 9.04 (1H, s) |
| Compound 216 | | | 116.0-117.0 | (200 MHz, CDCl3) δppm: 2.51 (3H, d, J = 0.9 Hz), 6.96 (1H, d, J = 0.9 Hz), 7.71 (1H, dd, J = 8.4, 1.8 Hz), 8.12 (1H, d, J = 7.9 Hz), 8.20 (1H, d, J = 1.8 Hz), 9.07 (1H, s) |

TABLE 1-continued

| Compound No. | Structural Formula of Compound | Salt form if applicable | Mp (° C.) | 1H-NMR |
|---|---|---|---|---|
| Compound 217 | | | 111.5-112.0 | |
| Compound 218 | | | | (200 MHz, CDCl3) δppm: 2.49 (3H, d, J = 0.9 Hz), 5.72 (1H, br), 6.73-6.88 (2H, m), 6.90 (1H, d, J = 0.9 Hz), 7.39-7.48 (2H, m) |
| Compound 219 | | | 82.0-83.0 | |
| Compound 220 | | | | (300 MHz, CDCl3) δppm: 6.02 (2H, s), 6.82 (1H, d, J = 8.1 Hz), 7.03 (1H, d, J = 1.7 Hz), 7.14 (1H, dd, J = 8.1, 1.7 Hz), 7.36 (1H, d, J = 3.4 Hz), 7.84 (1H, d, J = 3.4 Hz). |
| Compound 221 | | | | (300 MHz, CDCl3) δppm: 6.02 (2H, s), 6.82 (1H, d, J = 8.1 Hz), 7.00 (1H, d, J = 1.6 Hz), 7.13 (1H, dd, J = 8.1. 1.6 Hz), 7.23 (1H, s) |
| Compound 222 | | | | (300 MHz, CDCl3) δppm: 1.32 (3H, t, J = 7.5 Hz), 2.84 (2H, qd, J = 7.5, 0.9 Hz), 6.01 (2H, s), 6.81 (1H, dd, J = 8.1, 0.3 Hz), 6.91 (1H, t, J = 0.9 Hz), 7.01 (1H, dd J = 1.7, 0.3 Hz), 7.13 (1H, dd, J = 8.1, 1.7 Hz) |
| Compound 223 | | | | (300 MHz, CDCl3) δppm: 2.73 (3H, s), 5.99 (2H, s), 6.78 (1H, d, J = 8.1 Hz), 6.99 (1H, d, J = 1.7 Hz), 7.09 (1H, dd, J = 8.1, 1.7 Hz), 7.32 (1H, s) |
| Compound 224 | | | | (300 MHz, CDCl3) δppm: 2.75 (3H, s), 6.01 (2H, s), 6.81 (1H, d, J = 8.1 Hz), 7.02 (1H, d, J = 1.7 Hz), 7.13 (1H, dd, J = 8.1, 1.6 Hz), 7.76 (1H, s) |
| Compound 225 | | | | (300 MHz, CDCl3) δppm: 1.67 (3H, d, J = 6.5 Hz), 2.86 (1H, m), 5.16 (1H, m), 5.99 (2H, s), 6.79 (1H, d, J = 8.1 Hz), 7.00 (1H, d, J = 1.7 Hz), 7.10 (1H, dd, J = 8.1, 1.6 Hz), 7.44 (1H, s) |

TABLE 1-continued

| Compound No. | Structural Formula of Compound | Salt form if applicable | Mp (° C.) | 1H-NMR |
|---|---|---|---|---|
| Compound 226 | | | 137.0-140.0 | (300 MHz, CDCl3) δppm: 2.53 (3H, d, J = 1.1 Hz), 7.53 (1H, d, J = 1.1 Hz), 7.71 (1H, dd, J = 8.5, 1.6 Hz), 8.13 (1H, dd, J = 8.5, 0.6 Hz), 8.20 (1H, dd, J = 1.6, 0.5 Hz), 9.07 (1H, s) |
| Compound 227 | | | 154.0-155.0 | (300 MHz, CDCl3) δppm: 2.65 (3H, d, J = 1.1 Hz), 7.78 (1H, d, J = 1.1 Hz), 8.15 (1H, dd, J = 8.5, 1.7 Hz), 8.24 (1H, dd, J = 8.5, 0.6 Hz), 8.63 (1H, dd, J = 1.7, 0.6 Hz), 9.22 (1H, s) |
| Compound 228 | | | 210.0-211.0 | (300 MHz, DMSO-d6) δppm: 2.37 (3H, s), 2.42 (3H, s), 7.44 (1H, brs), 8.09-8.15 (2H, m), 8.78 (1H, br), 9.42 (1H, s), 12.53 (1H, br) |
| Compound 229 | | | 273.0-275.0 (dec.) | |
| Compound 230 | | | 263.0-268.0 (dec.) | |

TABLE 1-continued
| Compound No. | Structural Formula of Compound | Salt form if applicable | Mp (° C.) | 1H-NMR |
|---|---|---|---|---|
| Compound 231 | 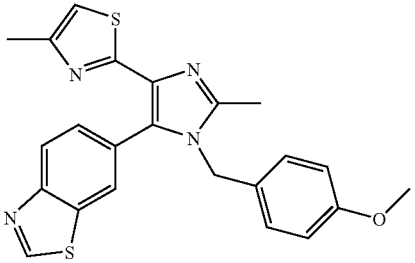 | | 144.0-145.0 | |
| Compound 232 | 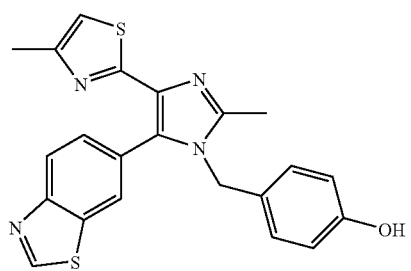 | | 215.5-218.5 | |
| Compound 233 | 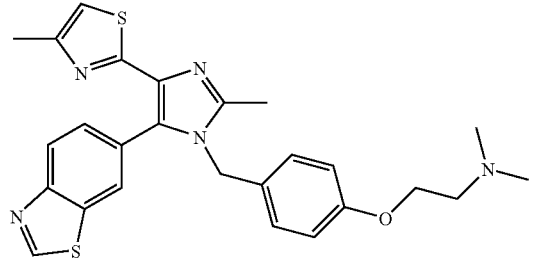 | | 146.5-148.0 | |
| Compound 234 | 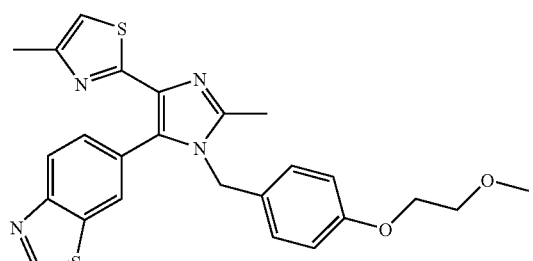 | | 129.5-131.0 | |
| Compound 235 | 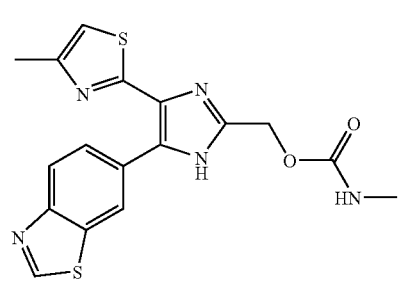 | | 158.0-159.5 | |

TABLE 1-continued

| Compound No. | Structural Formula of Compound | Salt form if applicable | Mp (° C.) | 1H-NMR |
|---|---|---|---|---|
| Compound 236 | | HCl | | (300 MHz, DMSO-d6) δppm: 2.39 (3H, d, J = 1.1 Hz), 3.34-3.49 (4H, m), 3.54-3.63 (4H, m), 5.27 (2H, s), 7.29 (1H, d, J = 1.1 Hz), 7.95 (1H, dd, J = 8.5, 1.9 Hz), 8.23 (1H, dd, J = 8.5, 0.5 Hz), 8.73 (1H, d, J = 1.9 Hz), 9.52 (1H, s) |
| Compound 237 | | HCl | 119.0-124.0 | |
| Compound 238 | | | 239.0-239.5 | |
| Compound 239 | | | 232.0-233.5 | |
| Compound 240 | | | 236.0-237.0 | |

TABLE 1-continued

| Compound No. | Structural Formula of Compound | Salt form if applicable | Mp (° C.) | 1H-NMR |
|---|---|---|---|---|
| Compound 241 | | | 220.5-222.0 | |
| Compound 242 | | | 224.5-226.5 | |
| Compound 243 | | | 253.0-255.0 (dec.) | |
| Compound 244 | | | 190.5-192.0 | (300 MHz, DMSO-d6) δppm: 2.40 (3H, m), 8.03 (1H, dd, J = 8.6, 1.5 Hz), 8.15 (1H, d, J = 8.6 Hz), 8.34 (1H, s), 8.89 (1H, brs), 9.45 (1H, s), 12.78 (1H, br) |
| Compound 245 | | | | (200 MHz, CDCl3) δppm: 1.49 (9H, m), 4.40 (2H, d, J = 6.2 Hz), 5.32 (1H, t, J = 5.7 Hz), 7.65 (1H, m), 7.84 (1H, dd, J = 8.4, 1.3 Hz), 8.19 (1H, d, J = 8.8 Hz), 8.90 (1H, d, J = 1.3 Hz), 9.06 (1H, m) |

TABLE 1-continued

| Compound No. | Structural Formula of Compound | Salt form if applicable | Mp (° C.) | 1H-NMR |
|---|---|---|---|---|
| Compound 246 | | 2HCl | | (300 MHz, DMSO-d6) δppm: 4.17-4.28 (2H, m), 8.06 (1H, dd, J = 8.5, 1.8 Hz), 8.20 (1H, d, J = 8.5 Hz), 8.43 (1H, d, J = 0.9 Hz), 8.67 (2H, brs), 8.93 (1H, d, J = 1.7 Hz), 9.49 (1H, s) |
| Compound 247 | | | | (300 MHz, DMSO-d6) δppm: 3.37 (3H, s), 3.90 (2H, m), 4.46 (2H, d, J = 5.8 Hz), 8.00 (1H, dd, J = 8.6, 1.6 Hz), 8.16 (1H, d, J = 8.5 Hz), 8.34-8.39 (2H, m), 8.83 (1H, d, J = 1.4 Hz), 9.46 (1H, m), 12.92 (1H, brs) |
| Compound 248 | | | | (300 MHz, DMSO-d6) δppm: 1.01 (3H, t, J = 7.1 Hz), 3.00-3.11 (2H, m), 4.33 (2H, d, J = 5.8 Hz), 6.08 (1H, t, J = 5.5 Hz), 6.37 (1H, t, J = 5.6 Hz), 8.01 (1H, dd, J = 8.6, 1.6 Hz), 8.16 (1H, d, J = 8.5 Hz), 8.37 (1H, m), 8.84 (1H, d, J = 1.2 Hz), 9.46 (1H, m), 12.93 (1H, brs) |
| Compound 249 | | | | (300 MHz, CDCl3) δppm: 1.72-1.89 (4H, m), 3.96-4.06 (2H, m), 4.58 (2H, d, J = 5.8 Hz), 6.74 (1H, brt, J = 5.1 Hz), 7.61 (1H, s), 7.81 (1H, dd, J = 8.5, 1.7 Hz), 8.16 (1H, d, J = 8.5 Hz), 8.65 (1H, brs), 9.06 (1H, s) |
| Compound 250 | | | 153.0-154.0 | (300 MHz, CDCl3) δppm: 7.74 (1H, dd, J = 8.5, 1.6 Hz), 7.81 (1H, q, J = 0.9 Hz), 8.16 (1H, dd, J = 8.5, 0.6 Hz), 8.24 (1H, dd, J = 1.7, 0.6 Hz), 9.11 (1H, s) |
| Compound 251 | | | 163.5-164.5 | (300 MHz, CDCl3) δppm: 8.14-8.32 (3H, m), 8.69 (1H, m), 9.27 (1H, s) |

Test Example 1

Smad2/3 Phosphorylation Inhibitory Activity Test

A549 cells were seeded to a plate, and cultured overnight in a Ham's F-12 medium supplemented with 10% FBS. This medium was replaced with the same medium containing the compounds or not containing the compounds, and after incubated another 2 hours, TGF-01 was added thereto so as to make its final concentration 1 ng/ml, and further incubated another 1 hour. After completion of incubation, the medium was removed, and the cells were washed with PBS and then lysed by a RIPA solution. The cell lysate solution was subjected to immunoprecipitation using anti-Smad2/3 antibody, and then Western blotting was performed. Using a rabbit anti-phosphorylated serine antibody as a primary antibody, a HRP-labeled anti-rabbit IgG antibody as a secondary antibody, and ECL Western blotting detection reagents as detection reagents, light emitting amounts were measured using Limi-Imager F1 (Roche Diagnostics) etc.

Following the above described methods, the inhibitory activities of the respective compounds against Smad2/3 phosphorylation caused by TGF-β1 stimulation were measured, and IC50 values were calculated.

The results are shown in Table 2.

TABLE 2

| Compound No. | IC50 (nM) |
|---|---|
| Compound 50 | 80 |
| Compound 52 | 24 |
| Compound 57 | 45 |
| Compound 68 | 31 |
| Compound 80 | 89 |
| Compound 81 | 52 |
| Compound 83 | 99 |
| Compound 87 | 38 |
| Compound 105 | 32 |
| Compound 124 | 67 |
| Compound 129 | 107 |
| Compound 171 | 89 |
| Compound 175 | 126 |
| Compound 176 | 77 |
| Compound 186 | 38 |
| Compound 191 | 31 |
| Compound 197 | 92 |
| Compound 198 | 93 |
| Compound 199 | 70 |
| Compound 201 | 42 |

Test Example 2

Hair Follicle Cell Proliferation Test

According to the method of by Arase et al.(Arase et al., J Dermatol sci 2, 66-70 (1991)), hair follicle cells were isolated from human hair and cultured by using KGM-1 (Clonetics).

After the follicle cells were seeded to a 24-well plate and cultured overnight, this medium was replaced with another medium containing the compounds or not containing the compounds, and after incubated culture another 2 hours, TGF-β1 was added thereto so as to make its final concentration 0.1 ng/ml, and further cultured another 72 hours. At 2 hours before the completion of culture, an Alamar blue reagent whose amount equals to ¹/₁₀ of the medium was added to the medium, and the fluorescence intensity of the medium (Ex: 544 nm, Em: 590 nm) was measured to determine the number of living cells. FIG. 1 shows the numbers of living cells when TGF-β1 was solely administered thereto and when TGF-β1 and the compound were simultaneously administered thereto, provided that the number of living cells determined when these cells were cultured for 72 hours without adding TGF-β1 is assumed to be 100%.

INDUSTRIAL APPLICABILITY

Compounds according to the present invention have inhibitory actions on ALK5 which is a TGF-β type I receptor, and useful as pharmaceutical products for treatment or prevention of various diseases such as alopecia or diabetic nephropathy associated with ALK5, a TGF-β type I receptor.

The invention claimed is:
1. A thiazole derivative represented by the formula (I)

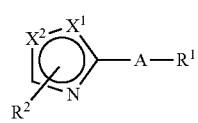

(I)

or a pharmaceutically acceptable salt thereof,
wherein:
$X^1$ and $X^2$ are different from each other and represent a sulfur atom or a carbon atom;
$R^1$ is selected from the group consisting of benzothiazolyl, benzoxazolyl or benzo(1,3)dioxoly;
$R^2$ represents a hydrogen atom, a halogen atom, an alkyl group having 1 to 6 carbon atoms, an alkyl group having 1 to 6 carbon atoms substituted with 1 to 5 halogen atoms, an alkoxy group having 1 to 6 carbon atoms, an alkanoyl group having 1 to 6 carbon atoms, or a hydroxyalkyl group having 1 to 5 carbon atoms;
and A represents a group which is represented by the formula

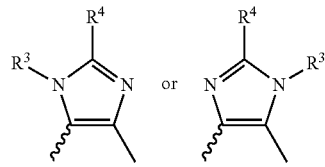

wherein:
 represents the bond to the thiazole group of formula (I);
$R^3$ represents a hydrogen atom;
a hydroxy group;
an alkyl group having 1 to 6 carbon atoms;
a phenylalkyl group having 7 to 12 carbon atoms; or
a phenylalkyl group having 7 to 12 carbon atoms, substituted with a hydroxy group, an alkoxy group having 1 to 6 carbon atoms, an alkoxy group having 1 to 6 carbon atoms substituted with an alkoxy group having 1 to 6 carbon atoms, or an alkoxy group having 1 to 6 carbon atoms substituted with an alkylamino group having 1 to 6 carbon atoms,
$R^4$ represents a phenyl group;
a phenyl group substituted with 1 to 5 members selected from the group consisting of halogen atoms, alkyl groups having 1 to 6 carbon atoms, alkoxy groups having 1 to 6 carbon atoms, a carbamoyl group, and a cyano group;
a hydrogen atom;
an alkyl group having 1 to 12 carbon atoms;

an alkenyl group having 2 to 12 carbon atoms;
a cycloalkyl group having 3 to 7 carbon atoms;
an alkyl group having 1 to 12 carbon atoms substituted with an alkoxy group having 1 to 6 carbon atoms, a hydroxy group, an alkoxyphenylalkoxy group having 8 to 12 carbon atoms, a phthalimidoyl group, a toluenesulfonyloxy group, or a morpholino group;
an alkyl group having 1 to 6 carbon atoms substituted with 1 to 5 halogen atoms;
a cycloalkyl group having 3 to 9 carbon atoms substituted with an oxo group;
a tetrahydropyranyl group;
a 4-piperidinyl group;
a piperidinyl group substituted with an alkyl group having 1 to 6 carbon atoms or a t-butoxycarbonyl group;
a cyclohexanespiro-2'-(1,3-dioxoranyl) group;
a pyrrolidin-2-one-5-yl group;
a group represented by the formula —$Y^1$—$Z^1$—$NR^5$—$Z^2$—$Y^2$—$R^6$,
wherein:
$Y^1$ and $Y^2$ are the same or different from each other and represent a single bond or an alkylene group having 1 to 12 carbon atoms;
$R^5$ represents a hydrogen atom or an alkyl group having 1 to 12 carbon atoms;
$Z^1$ and $Z^2$ are the same or different from each other and represent a single bond;
an alkylene group having 1 to 7 carbon atoms;
—CO—;
—$CO_2$—
—$SO_2$—; or
—OCO—, and
$R^6$ represents
a cycloalkyl group having 3 to 7 carbon atoms;
an alkyl group having 1 to 6 carbon atoms substituted with 1 to 3 halogen atoms;
an alkenyl group having 2 to 6 carbon atoms;
an alkynyl group having 2 to 6 carbon atoms;
an amino group;
an amino group substituted with 1 to 2 groups selected from the group consisting of an alkyl group having 1 to 6 carbon atoms, a cycloalkyl group having 3 to 7 carbon atoms, and a t-butoxycarbonyl group;
a piperidino group;
a piperidinyl group;
a piperidinyl group substituted with an alkyl group having 1 to 6 carbon atoms;
a pyrrolidinyl group;
a piperazinyl group;
a piperazinyl group substituted with an alkyl group having 1 to 6 carbon atoms;
a morpholino group;
a hydroxy group;
an alkoxy group having 1 to 6 carbon atoms;
an alkoxy group having 1 to 6 carbon atoms substituted by a hydroxy group or an alkoxy group having 1 to 6 carbon atoms;
an oxetan-2-yl group;
a tetrahydrofuranyl group;
a tetrahydropyranyl group;
a hydrogen atom;
a phenyl group;
a phenyl group substituted with an alkoxy group having 1 to 4 carbon atoms; or
a group that forms a ring when linked to the nitrogen atom of the above formula; or
a group represented by the formula —$Y^3$—CO—$R^{41}$,
wherein:
$Y^3$ represents a single bond or an alkylene group having 1 to 7 carbon atoms,
$R^{41}$ represents
a hydroxy group;
an alkoxy group having 1 to 6 carbon atoms;
a piperidino group;
a piperazin-1-yl group substituted by an alkyl group having 1 to 6 carbon atoms, a morpholinoalkyl group having 5 to 10 carbon atoms, or an alkylaminoalkyl group having 2 to 14 carbon atoms; or
a morpholino group.

2. The thiazole derivative or a pharmaceutically acceptable salt thereof according to claim 1, wherein $R^2$ is a hydrogen atom, a halogen atom, an alkyl group having 1 to 6 carbon atoms or an alkyl group having 1 to 6 carbon atoms substituted with 1 to 5 halogen atoms.

3. The thiazole derivative or a pharmaceutically acceptable salt thereof according to claim 1, wherein $R^2$ is an alkyl group having 1 to 6 carbon atoms or a trifluoromethyl group.

4. The thiazole derivative or a pharmaceutically acceptable salt thereof according to claim 1, wherein $R^2$ is a methyl group or a trifluoromethyl group.

5. The thiazole derivative or a pharmaceutically acceptable salt thereof according to claim 1, wherein $X^1$ is a sulfur atom and $X^2$ is a carbon atom.

6. The thiazole derivative or a pharmaceutically acceptable salt thereof according to claim 1, wherein $X^1$ is a sulfur atom and $X^2$ is a carbon atom;
$R^1$ is selected from the group consisting of benzothiazolyl, benzoxazolyl, and benzo(1,3)dioxolyl,
$R^2$ is a methyl group;
and A represents a group which is represented by the formula A:

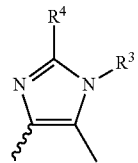

wherein $R^3$ a hydrogen atom and
$R^4$ is represented by the formula:
—$Y^1$—$Z^1$—$NR^5$—$Z^2$—$Y^2$—$R^6$, wherein —$Y^1$—$Z^1$ is —$CH_2$—; $R^5$ is a hydrogen atom; $Z^2$ is —$CO_2$—; $Y^2$ is 2-methylpropan-1,3-diyl, and $R^6$ is a hydrogen atom.

7. A method for treating glomerulonephritis, diabetic nephropathy, hepatic fibrosis, liver cirrhosis, pulmonary fibrosis, or alopeciarosis in a subject in need thereof, the method comprising administering to the subject a composition comprising a therapeutically effective amount of the thiazole derivative or a pharmaceutically acceptable salt thereof according to claim 1.

8. The method of claim 7, wherein the administration is carried out by external application.

* * * * *